United States Patent
Denzinger et al.

(10) Patent No.: US 11,413,114 B2
(45) Date of Patent: Aug. 16, 2022

(54) ULTRASONIC SURGICAL INSTRUMENT WITH BLADE CLEANING FEATURE

(71) Applicant: Ethicon LLC, Guaynabo, PR (US)

(72) Inventors: Kristen G. Denzinger, Cincinnati, OH (US); Ashvani K. Madan, Mason, OH (US); Cory G. Kimball, Hamilton, OH (US); Robert A. Kemerling, Mason, OH (US); John A. Hibner, Mason, OH (US); Rafael J. Ruiz Ortiz, Mason, OH (US); Catherine A. Corbett, Cincinnati, OH (US); Michael R. Lamping, Cincinnati, OH (US); Thomas B. Remm, Milford, OH (US)

(73) Assignee: Cilag GmbH International, Zug (CH)

( * ) Notice: Subject to any disclaimer, the term of this patent is extended or adjusted under 35 U.S.C. 154(b) by 241 days.

(21) Appl. No.: 16/388,912

(22) Filed: Apr. 19, 2019

(65) Prior Publication Data

US 2019/0307528 A1 Oct. 10, 2019

Related U.S. Application Data

(63) Continuation of application No. 14/976,483, filed on Dec. 21, 2015, now Pat. No. 10,368,957.

(51) Int. Cl.
*A61B 90/70* (2016.01)
*A61B 17/32* (2006.01)
(Continued)

(52) U.S. Cl.
CPC ...... *A61B 90/70* (2016.02); *A61B 17/320068* (2013.01); *A61B 17/320092* (2013.01);
(Continued)

(58) Field of Classification Search
CPC ............ A61B 90/70; A61B 17/320068; A61B 17/320092; A61B 2017/320074; A61B 2017/320093; A61B 2017/320094
See application file for complete search history.

(56) References Cited

U.S. PATENT DOCUMENTS 5,168,593 A 12/1992 Poje et al.
5,322,055 A 6/1994 Davison et al.
(Continued)

FOREIGN PATENT DOCUMENTS

WO WO 2015/073428 A1 5/2015

OTHER PUBLICATIONS

International Search Report and Written Opinion dated Apr. 21, 2017 for International Application No. PCT/US2016/066470, 11 pages.
(Continued)

*Primary Examiner* — Melanie R Tyson
(74) *Attorney, Agent, or Firm* — Frost Brown Todd LLC

(57) ABSTRACT

A surgical instrument includes a shaft assembly, an ultrasonic blade, and a cleaning device. The shaft assembly includes a first tube and an acoustic waveguide. The first tube has a first inner diameter and a distal end. The waveguide has a first outer diameter. The waveguide extends within the first tube. The first outer diameter of the acoustic waveguide and the first inner diameter of the first tube together define a gap. The ultrasonic blade extends distally from the distal end of the first tube. The acoustic waveguide is configured to communicate ultrasonic energy to the ultrasonic blade. The cleaning device is configured to actuate within the gap to thereby clean at least a portion of the shaft assembly and/or at least a portion of the ultrasonic blade.

17 Claims, 37 Drawing Sheets

(51) Int. Cl.
*A61N 7/02* (2006.01)
*A61B 18/00* (2006.01)
*A61N 7/00* (2006.01)

(52) U.S. Cl.
CPC .... *A61N 7/02* (2013.01); *A61B 2017/320088* (2013.01); *A61B 2017/320094* (2017.08); *A61B 2018/0063* (2013.01); *A61B 2018/00595* (2013.01); *A61B 2018/00619* (2013.01); *A61N 2007/0056* (2013.01)

(56) References Cited

U.S. PATENT DOCUMENTS

| | | |
|---|---|---|
| 5,873,873 A | 2/1999 | Smith et al. |
| 5,980,510 A | 11/1999 | Tsonton et al. |
| 6,283,981 B1 | 9/2001 | Beaupre |
| 6,309,400 B2 | 10/2001 | Beaupre |
| 6,325,811 B1 | 12/2001 | Messerly |
| 6,423,082 B1 | 7/2002 | Houser et al. |
| 6,773,444 B2 | 8/2004 | Messerly |
| 6,783,524 B2 | 8/2004 | Anderson et al. |
| 8,057,498 B2 | 11/2011 | Robertson |
| 8,461,744 B2 | 6/2013 | Wiener et al. |
| 8,591,536 B2 | 11/2013 | Robertson |
| 8,623,027 B2 | 1/2014 | Price et al. |
| 8,911,460 B2 | 12/2014 | Neurohr et al. |
| 9,023,071 B2 | 5/2015 | Miller et al. |
| 9,095,367 B2 | 8/2015 | Olson et al. |
| 9,381,058 B2 | 7/2016 | Houser et al. |
| 9,393,037 B2 | 7/2016 | Olson et al. |
| 9,629,684 B2 | 4/2017 | Jenkins et al. |
| 9,901,358 B2 | 2/2018 | Faller et al. |
| 10,368,957 B2 * | 8/2019 | Denzinger ............... A61N 7/02 |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2012/0116265 A1 | 5/2012 | Houser et al. |
| 2015/0142031 A1 * | 5/2015 | Faller ................. A61B 90/70 606/169 |
| 2015/0245850 A1 | 9/2015 | Hibner et al. |
| 2016/0015419 A1 | 1/2016 | Hibner et al. |

OTHER PUBLICATIONS

U.S. Appl. No. 61/410,603, filed Nov. 5, 2010.
Brazilian Office Action, Search Report, dated Jun. 18, 2020 for Application No. BR 112018012541-5, 4 pgs.
Chinses Office Action, The First Office Action, and First Search, dated Jul. 3, 2020 for Application No. CN 201680074914.X, 12 pgs.
Japanese Office Action, Notice of Reasons for Refusal, and First Search Report by Registered Search Organization, dated Jan. 19, 2021 for Application No. JP 2018-550659, 29 pgs.
Japanese Office Action, Decision to Grant a Patent, dated May 11, 2021 for Application No. JP 2018-550659, 2 pgs.

\* cited by examiner

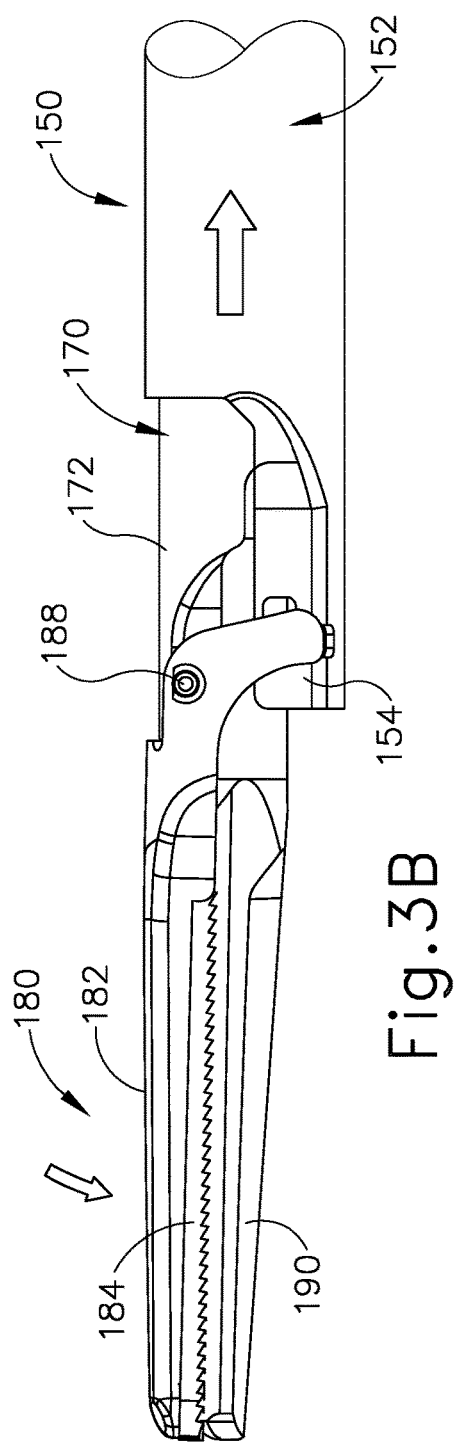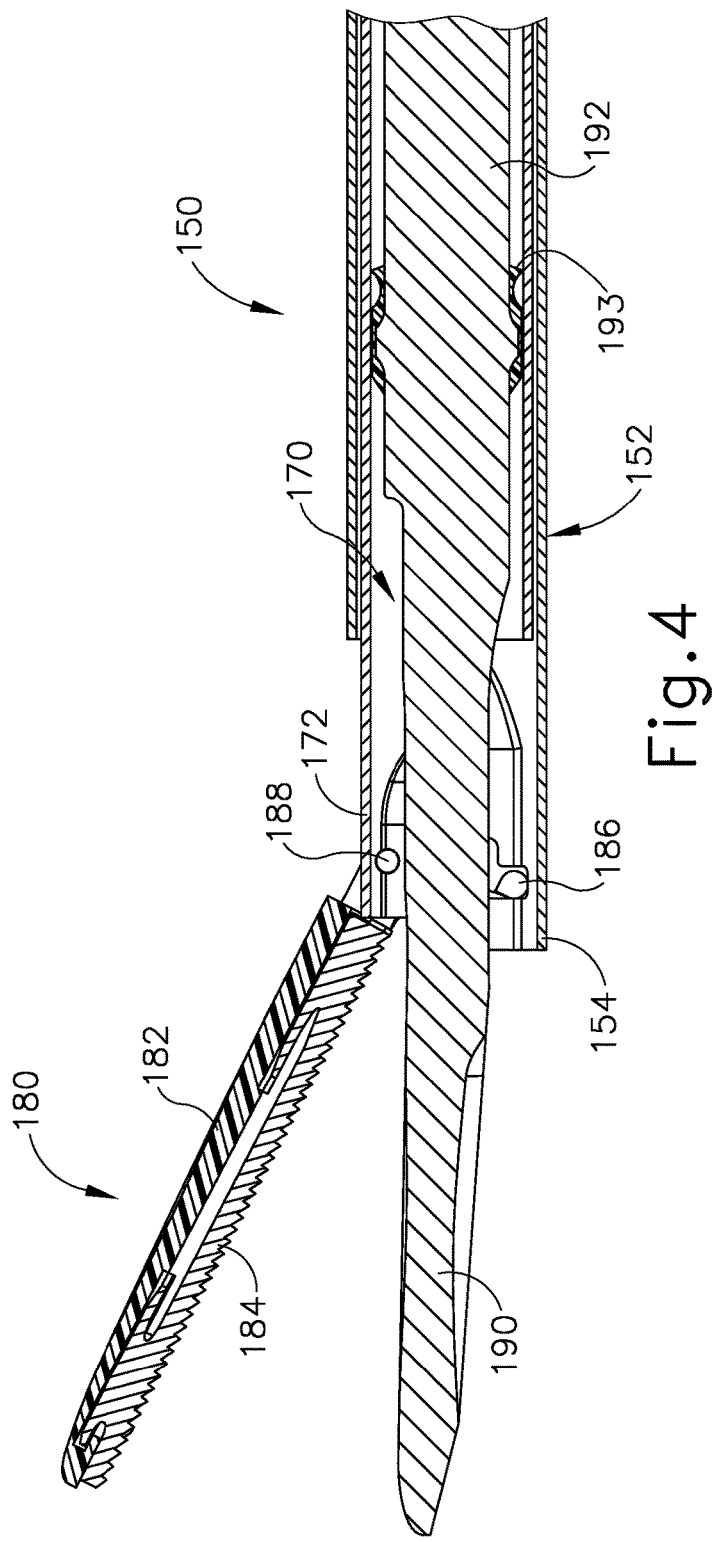

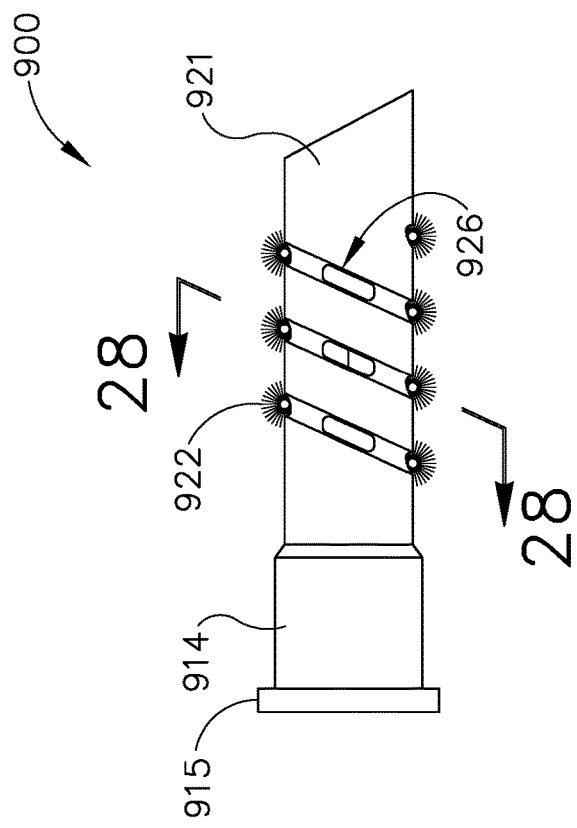
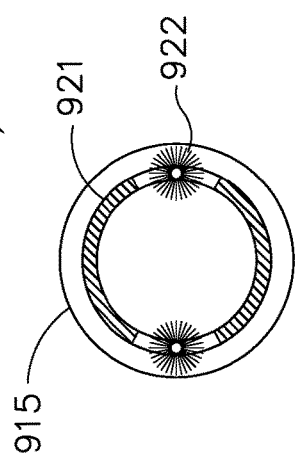
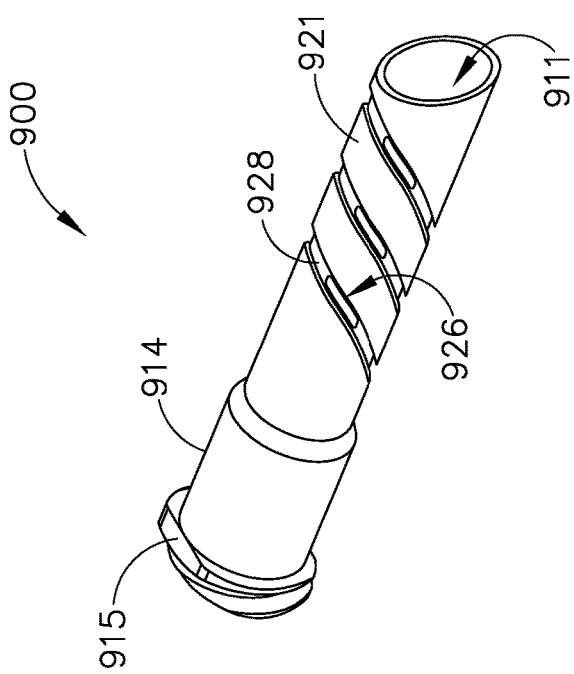
Fig. 27
Fig. 28
Fig. 26

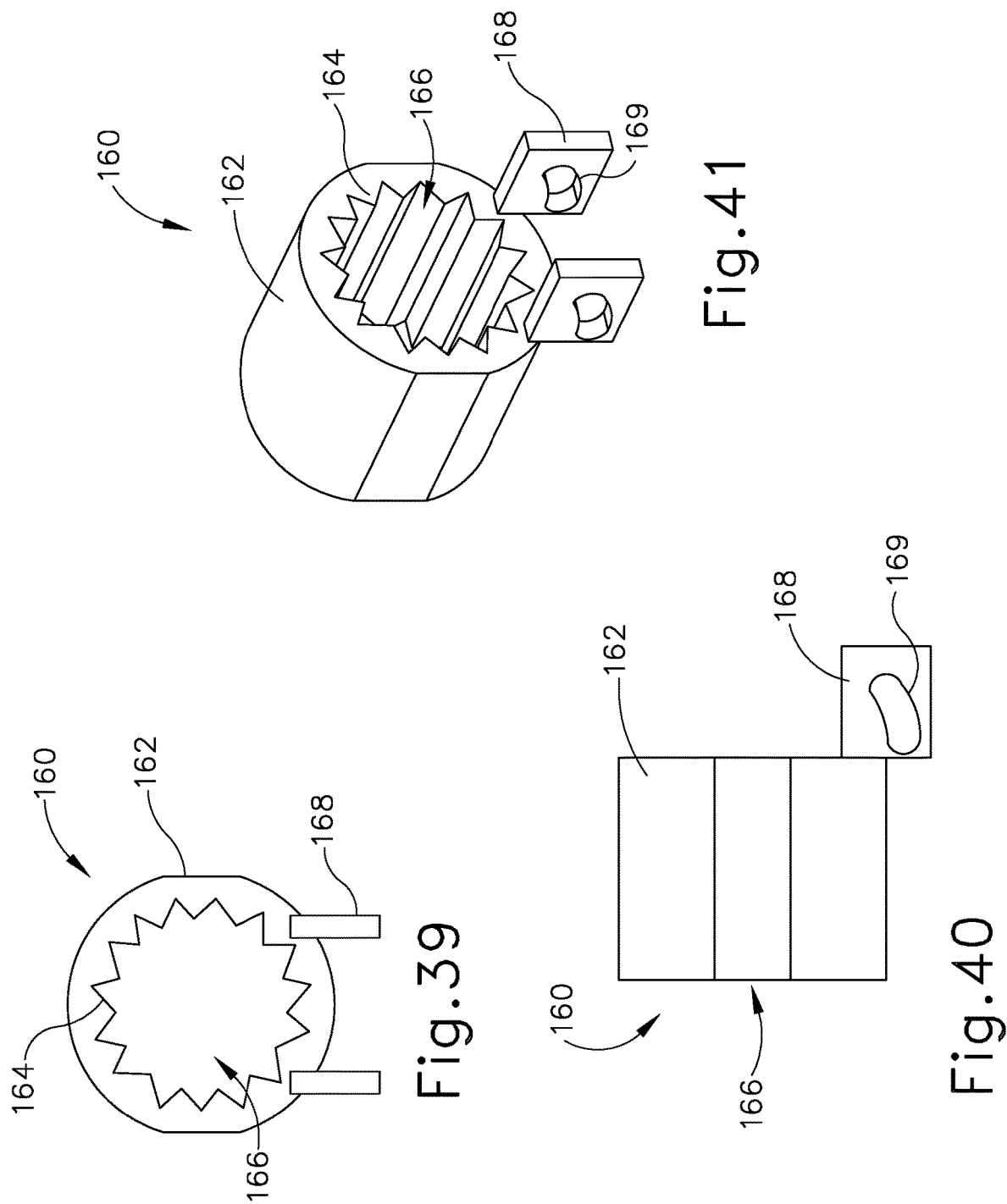

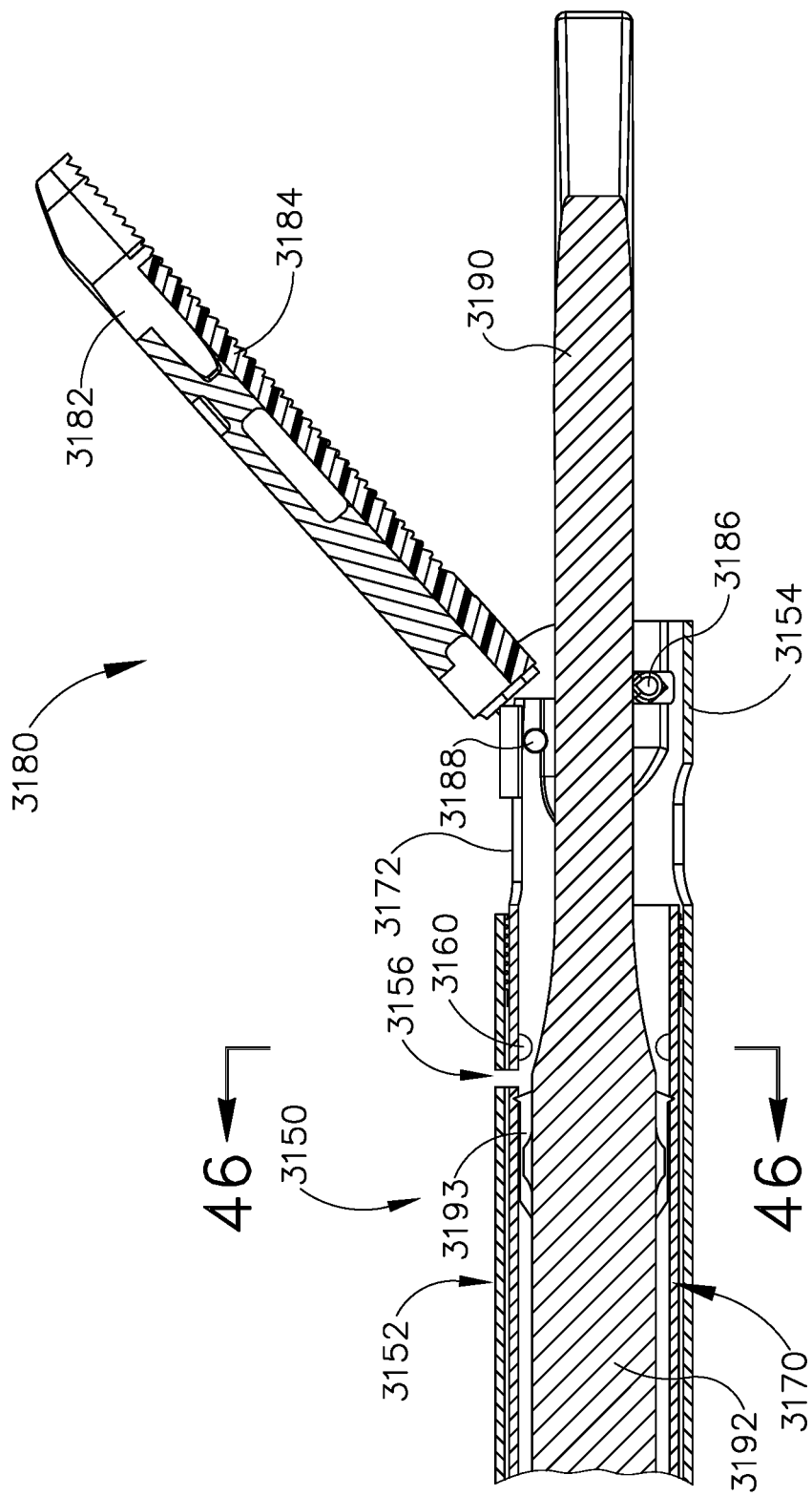

11,413,114 B2

ULTRASONIC SURGICAL INSTRUMENT WITH BLADE CLEANING FEATURE

This application is a continuation of U.S. patent application Ser. No. 14/976,483, entitled "Ultrasonic Surgical Instrument with Blade Cleaning Feature," filed Dec. 21, 2015, and published as U.S. Publication No. 2017/0172700 on Jun. 22, 2017, issued as U.S. Pat. No. 10,368,957 on Aug. 6, 2019.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. Some instruments have a clamp arm and clamp pad for grasping tissue with the blade element.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Clamp pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2008/0234710, entitled "Ultrasonic Surgical Instruments," published Sep. 25, 2008, issued as U.S. Pat. No. 8,911,460 on Dec. 16, 2014, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, entitled "Surgical Instruments with Articulating Shafts," issued as U.S. Pat. No. 9,393,037 on Jul. 19, 2016, the disclosure of which is incorporated by reference herein; and U.S. Pub. No. 2014/0114334, published Apr. 24, 2014, entitled "Flexible Harmonic Waveguides/Blades for Surgical Instruments," issued as U.S. Pat. No. 9,095,367 on Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 3B depicts a side elevational view of the end effector and shaft assembly of FIG. 2, in a closed configuration;

FIG. 4 depicts a side cross-sectional view of the end effector and shaft assembly of FIG. 2, in the open configuration;

FIG. 26 depicts a perspective view of another alternative cleaning device that may be used to clean the end effector and shaft assembly of FIG. 2, with a bristle section omitted;

FIG. 27 depicts a side elevational view of the cleaning device of FIG. 26, with the bristle section included;

FIG. 28 depicts a cross-sectional view of the cleaning device of FIG. 26, with the bristle section included, taken along line 28-28 of FIG. 27;

FIG. 39 depicts a front elevational view of a slidable cleaning device that may be attached to the end effector and the shaft assembly of FIG. 2;

FIG. 40 depicts a side elevational view of the slidable cleaning device of FIG. 39;

FIG. 41 depicts a perspective view of the slidable cleaning device of FIG. 39;

FIG. 45A depicts cross-sectional side view of an alternative shaft assembly and end effector that may be incorporated into the instrument of FIG. 1, where a waveguide of the shaft assembly is in a first, proximal position;

Figure 1:
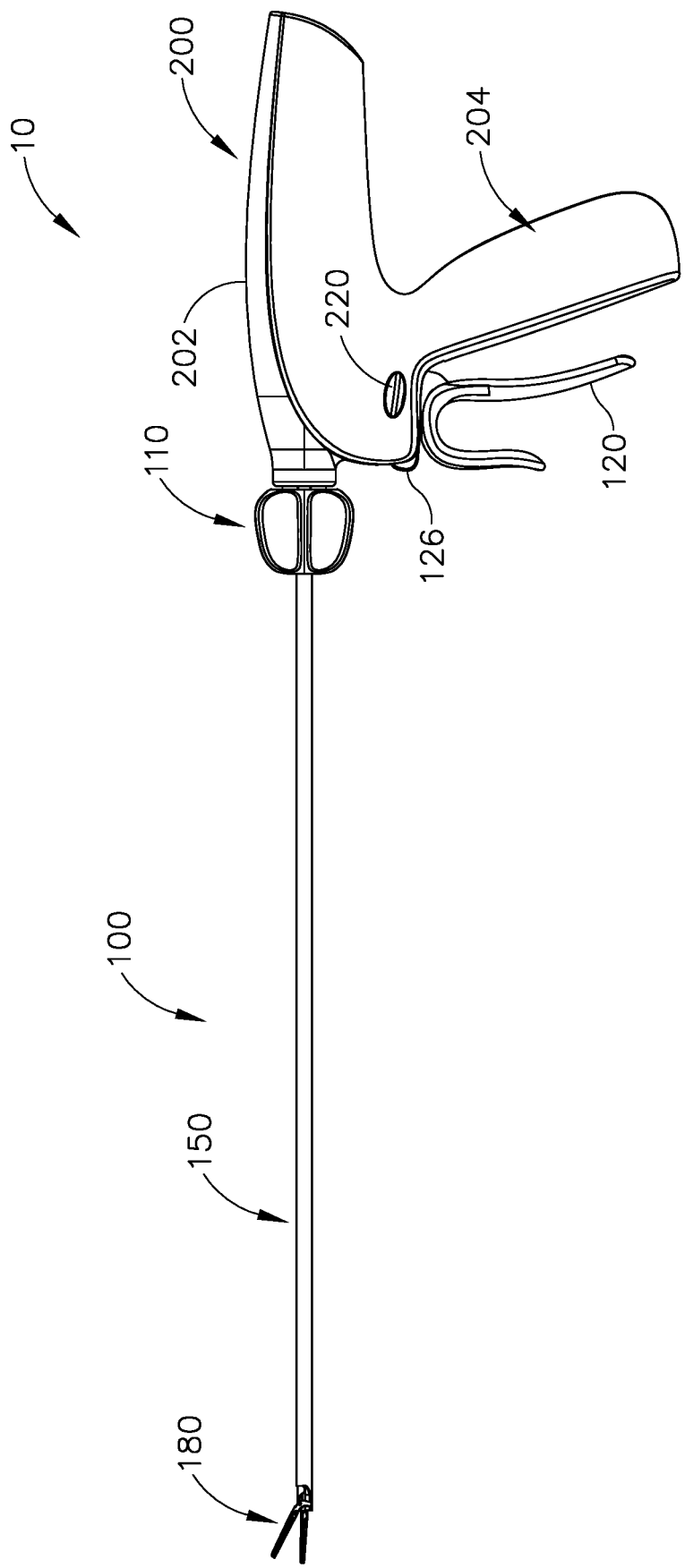
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Overview of Exemplary Ultrasonic Surgical Instrument

Figure 2:
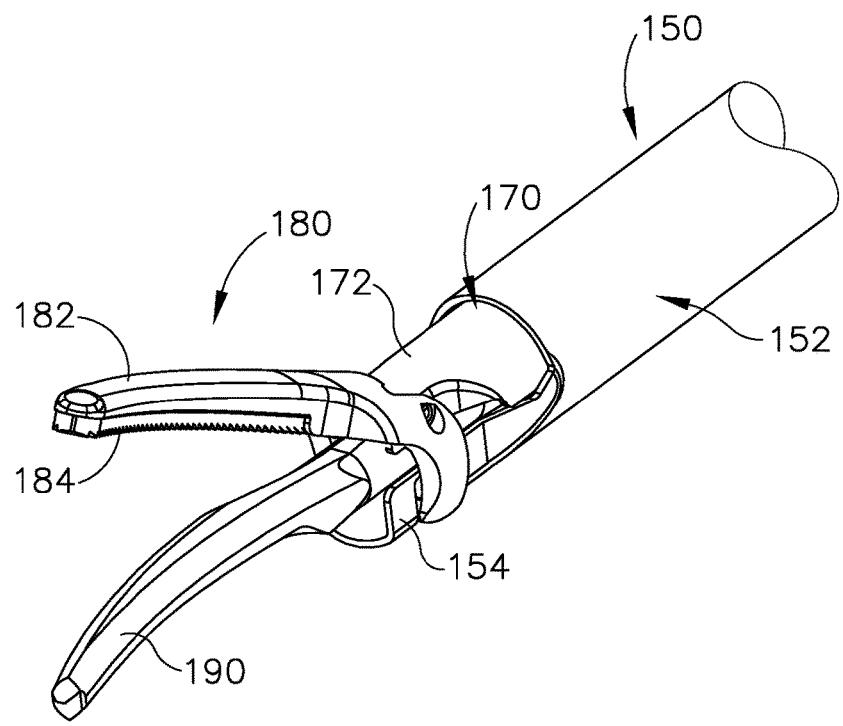
FIG. 2 depicts a perspective view of an end effector and shaft assembly of the instrument of FIG. 1, in an open configuration.

FIGS. 1-3 show an exemplary ultrasonic surgical instrument (10) that is configured to be used in minimally invasive surgical procedures (e.g., via a trocar or other small diameter access port, etc.). As will be described in greater detail below, instrument (10) is operable to cut tissue and seal or weld tissue (e.g., a blood vessel, etc.) substantially simultaneously. Instrument (10) of this example comprises a disposable assembly (100) and a reusable assembly (200). The distal portion of reusable assembly (200) is configured to removably receive the proximal portion of disposable assembly (100) to form instrument (10).

In an exemplary use, assemblies (100, 200) are coupled together to form instrument (10) before a surgical procedure, the assembled instrument (10) is used to perform the surgical procedure, and then assemblies (100, 200) are decoupled from each other for further processing. In some instances, after the surgical procedure is complete, disposable assembly (100) is immediately disposed of while reusable assembly (200) is sterilized and otherwise processed for re-use. By way of example only, reusable assembly (200) may be sterilized in a conventional relatively low temperature, relatively low pressure, hydrogen peroxide sterilization process. Alternatively, reusable assembly (200) may be sterilized using any other suitable systems and techniques (e.g., autoclave, etc.). In some versions, reusable assembly (200) may be sterilized and reused approximately 100 times. Alternatively, reusable assembly (200) may be subject to any other suitable life cycle. For instance, reusable assembly (200) may be disposed of after a single use, if desired. While disposable assembly (100) is referred to herein as being "disposable," it should be understood that, in some instances, disposable assembly (100) may also be sterilized and otherwise processed for re-use. By way of example only, disposable assembly (100) may be sterilized and reused approximately 2-30 times, using any suitable systems and techniques. Alternatively, disposable assembly (100) may be subject to any other suitable life cycle.

In some versions, disposable assembly (100) and/or reusable assembly (200) includes one or more features that are operable to track usage of the corresponding assembly (100, 200), and selectively restrict operability of the corresponding assembly (100, 200) based on use. For instance, disposable assembly (100) and/or reusable assembly (200) may include one or more counting sensors and a control logic (e.g., microprocessor, etc.) that is in communication with the counting sensor(s). The counting sensor(s) may be able to detect the number of times the ultrasonic transducer of instrument (10) is activated, the number of surgical procedures the corresponding assembly (100, 200) is used in, the number of trigger closures, and/or any other suitable conditions associated with use. The control logic may track data from the counting sensor(s) and compare the data to one or more threshold values. When the control logic determines that one or more threshold values have been exceeded, the control logic may execute a control algorithm to disable operability of one or more components in the corresponding assembly (100, 200). In instances where the control logic stores two or more threshold values (e.g., a first threshold for number of activations and a second threshold for number of surgical procedures, etc.), the control logic may disable operability of one or more components in the corresponding assembly (100, 200) the first time one of those thresholds is exceeded, or on some other basis.

In versions where a control logic is operable to disable instrument (10) based on the amount of use, the control logic may also determine whether instrument (10) is currently being used in a surgical procedure, and refrain from disabling instrument (10) until that particular surgical procedure is complete. In other words, the control logic may allow the operator to complete the current surgical procedure but prevent instrument (10) from being used in a subsequent surgical procedure. Various suitable forms that counters or other sensors may take will be apparent to those of ordinary skill in the art in view of the teachings herein. Various suitable forms that a control logic may take will also be apparent to those of ordinary skill in the art in view of the teachings herein. Similarly, various suitable control algorithms that may be used to restrict usage of instrument (10) will be apparent to those of ordinary skill in the art in view of the teachings herein. Of course, some versions of instrument (10) may simply omit features that track and/or restrict the amount of usage of instrument (10).

Figure 3A:
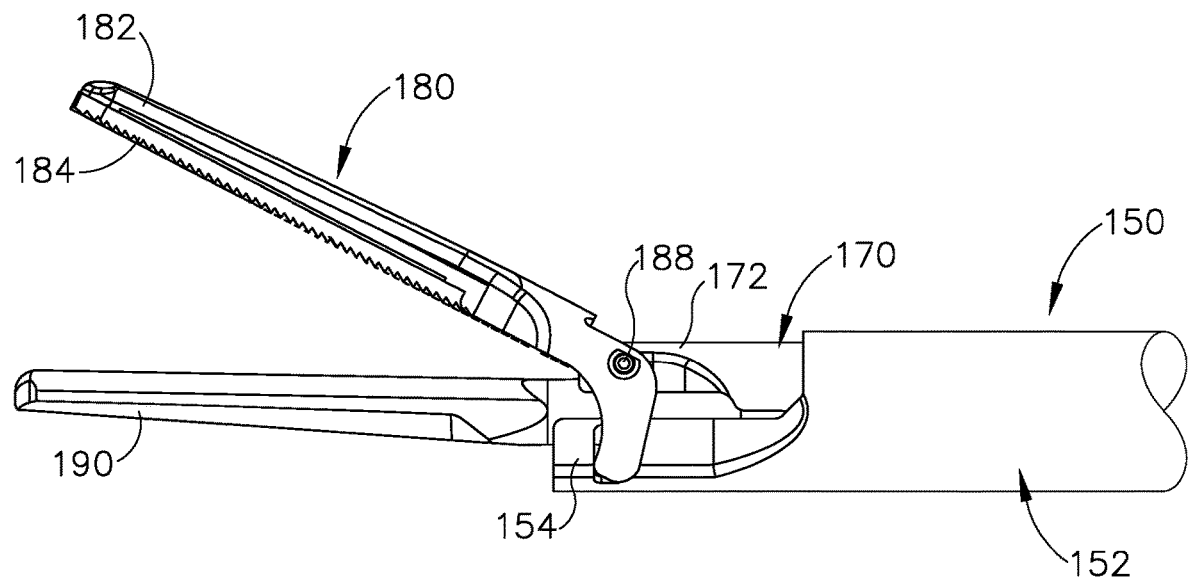
FIG. 3A depicts a side elevational view of the end effector and shaft assembly of FIG. 2, in the open configuration.

Disposable assembly (100) of the present example comprises a body portion (110), a shaft assembly (150) extending distally from body portion (110), and an end effector (180) located at the distal end of shaft assembly (150). As best seen in FIGS. 2-4, end effector (180) of this example comprises a clamp arm (182) and an ultrasonic blade (190). Clamp arm (182) includes a clamp pad (184), which faces blade (190). As shown in FIGS. 3A-3B and as will be described in greater detail below, clamp arm (182) is pivotable toward and away from blade (190) to selectively compress tissue between clamp pad (184) and blade (190). As seen in FIG. 4, blade (190) is an integral feature of the distal end of an acoustic waveguide (192), which extends coaxially through tubes (152, 170), and which is configured to communicate ultrasonic vibrations to blade (190) as will be described in greater detail below.

Shaft assembly (150) comprises an outer tube (152) and an inner tube (170) and a rotation knob (112). Rotation knob (112) is operable to rotate the entire shaft assembly (150) and end effector (180) relative to reusable assembly (200) about a longitudinal axis of shaft assembly (150). In some versions, rotation knob (112) is operable to selectively lock the angular position of shaft assembly (150) and end effector (180) relative to reusable assembly (200) about the longitudinal axis of shaft assembly (150).

Outer tube (152) is operable to translate longitudinally relative to inner tube (170) to selectively pivot clamp arm (182) toward and away from blade (190). To accomplish this, and as best seen in FIG. 4, integral pin features (186) of clamp arm (182) pivotally secure a first portion of clamp arm (182) to a distally projecting tongue (154) of outer tube (152); while an inserted pin (188) pivotally secures a second portion of clamp arm (182) to a distally projecting tongue (172) of inner tube (170). Thus, as can be seen in the transition from FIG. 3A to FIG. 3B, tubes (152, 170) cooperate to pivot clamp arm (182) toward blade (190) when outer tube (152) is retracted proximally relative to inner tube (170). It should be understood that clamp arm (182) may be pivoted back away from blade (190) (e.g., from the position shown in FIG. 6B to the position shown in FIG. 6A) by translating outer tube (152) distally relative to inner tube (170), in reverse of the operation shown in FIGS. 6A-6B. In an exemplary use, clamp arm (182) may be pivoted toward blade (190) to grasp, compress, seal, and sever tissue captured between clamp pad (184) and blade (190). Clamp arm (182) may be pivoted away from blade (190) to release tissue from between clamp pad (184) and blade (190); and/or to perform blunt dissection of tissue engaging opposing outer surfaces of clamp arm (182) and blade (190).

Shaft assembly (150) includes a distal seal (193), which is coaxially interposed between the outer diameter of waveguide (192) and the inner diameter of inner tube (170). In the present example, distal seal (193) comprises an elastomeric material (e.g., rubber, silicone, etc.). Distal seal (193) is located at a position corresponding to a node associated with ultrasonic vibrations that are communicated through waveguide (192).

As seen in FIG. 1, reusable assembly (200) comprises a handle housing (202). Housing (202) defines a pistol grip (204) while disposable assembly (100) includes a trigger (120) pivotally coupled to housing when assemblies (100, 200) are sufficiently coupled. Clamp arm (182) is coupled with trigger (120) such that clamp arm (182) is pivotable toward ultrasonic blade (190) in response to pivoting of trigger (120) toward pistol grip (204); and such that clamp arm (182) is pivotable away from ultrasonic blade (190) in response to pivoting of trigger (120) away from pistol grip (204). While reusable assembly (200) includes a pistol grip (204) in this example, it should be understood that any other suitable kind of grip may be used. Reusable assembly (200) includes a battery (not shown), a generator (not shown), and an ultrasonic transducer assembly (not shown). Disposable assembly (100) also includes an activation button (126) electrically coupled to reusable assembly (200) when assemblies (100, 200) are sufficiently coupled. Battery (not shown) is operable to provide electrical power to generator (not shown); generator (not shown) is operable to provide electrical power to ultrasonic transducer assembly (not shown); and ultrasonic transducer assembly is operable to convert electrical power into ultrasonic vibrations. Activation button (126) may activate ultrasonic transducer assembly to convert electrical power into ultrasonic vibrations.

When waveguide (192) is sufficiently coupled with transducer assembly (not shown), ultrasonic vibrations that are generated by transducer assembly (not shown) are communicated along waveguide (192) to reach blade (190). In the present example, the distal end of blade (190) is located at a position corresponding to an anti-node associated with resonant ultrasonic vibrations communicated through waveguide (192), in order to tune the acoustic assembly to a preferred resonant frequency $f_o$ when the acoustic assembly is not loaded by tissue. When transducer assembly (not shown) is energized, the distal end of blade (190) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (not shown) of the present example is activated, these mechanical oscillations are transmitted through waveguide (192) to reach blade (190), thereby providing oscillation of blade (190) at the resonant ultrasonic frequency. Thus, when tissue is secured between blade (190) and clamp pad (184), the ultrasonic oscillation of blade (190) may simultaneously sever the tissue and denature the proteins in adjacent tissue cells, thereby providing a coagulative effect with relatively little thermal spread. In some versions, an electrical current may also be provided through blade (190) and/or clamp pad (184) to also seal the tissue.

By way of example only, instrument (10) may be further constructed and operable in accordance with at least some of the teachings of U.S. patent application Ser. No. 14/868,574, entitled "Ultrasonic Surgical Instrument with Removable Handle Assembly," filed Sep. 29, 2015, published as U.S. Pub. No. 2016/0015419 on Jan. 21, 2016, issued as U.S. Pat. No. 10,349,967 on Jul. 16, 2019, the disclosure of which is incorporated by reference herein; and/or U.S. patent application Ser. No. 14/623,812, entitled "Ultrasonic Surgical Instrument with Removable Handle Assembly," filed Feb. 17, 2015, issued as U.S. Pat. No. 10,010,340 on Jul. 3, 2018, the disclosure of which is incorporated by reference herein. Further exemplary features and operabilities for disposable assembly (100) and reusable assembly (200) will be described in greater detail below, while other variations will be apparent to those of ordinary skill in the art in view of the teachings herein.

II. Exemplary Cleaning Devices

In some instances during a surgical procedure, tissue debris, coagulated blood, and/or other substances may tend to collect on the outer diameters of ultrasonic blade (190) and acoustic waveguide (192), the inner diameters of distally projecting tongues (154, 172) and inner tube (170), as well as the distal portion of seal (193) itself. Due to the mechanical vibrations of acoustic waveguide (192) and ultrasonic blade (190), this collected debris, etc., may cake onto and stick to the above motioned areas excessively. If debris, etc. does collect onto the above mentioned areas excessively, performance of instrument (10) may be negatively affected. For instance, collected debris, etc. may interfere with mechanical oscillations transmitted through waveguide (192) and blade (190).

In view of the foregoing, it may be beneficial to have a cleaning device that is capable of easily removing such debris, etc. during a surgical procedure. Additionally or alternatively, it may be beneficial to have a cleaning that is device capable of removing such debris, etc. in between surgical procedures. Several merely illustrative examples of such cleaning devices are described in greater detail below. While the following examples are provided in the context of cleaning instrument (10), it should be understood that the below described cleaning devices may also be used with various other kinds of instruments, including but not limited to the various instruments described in the various references that are cited herein.

A. Exemplary Detachable Cleaning Devices

In some instances, it may be desirable to provide an end effector and/or shaft assembly cleaning device that is separate from (or separable from) instrument (10). This may allow the cleaning device to be used with conventional instruments without requiring modification to the conventional instruments. This may also enable more than one cleaning device to be used on a single instrument (10), such as during a long surgical procedure where a first cleaning device may become unusable due to repeated cleaning. The following discussion provides several merely illustrative examples of end effector and/or shaft assembly cleaning devices that are separate from (or separable from) instrument (10).

1. Exemplary Cleaning Device with Helical Brush and Fluid Port

Figure 5:
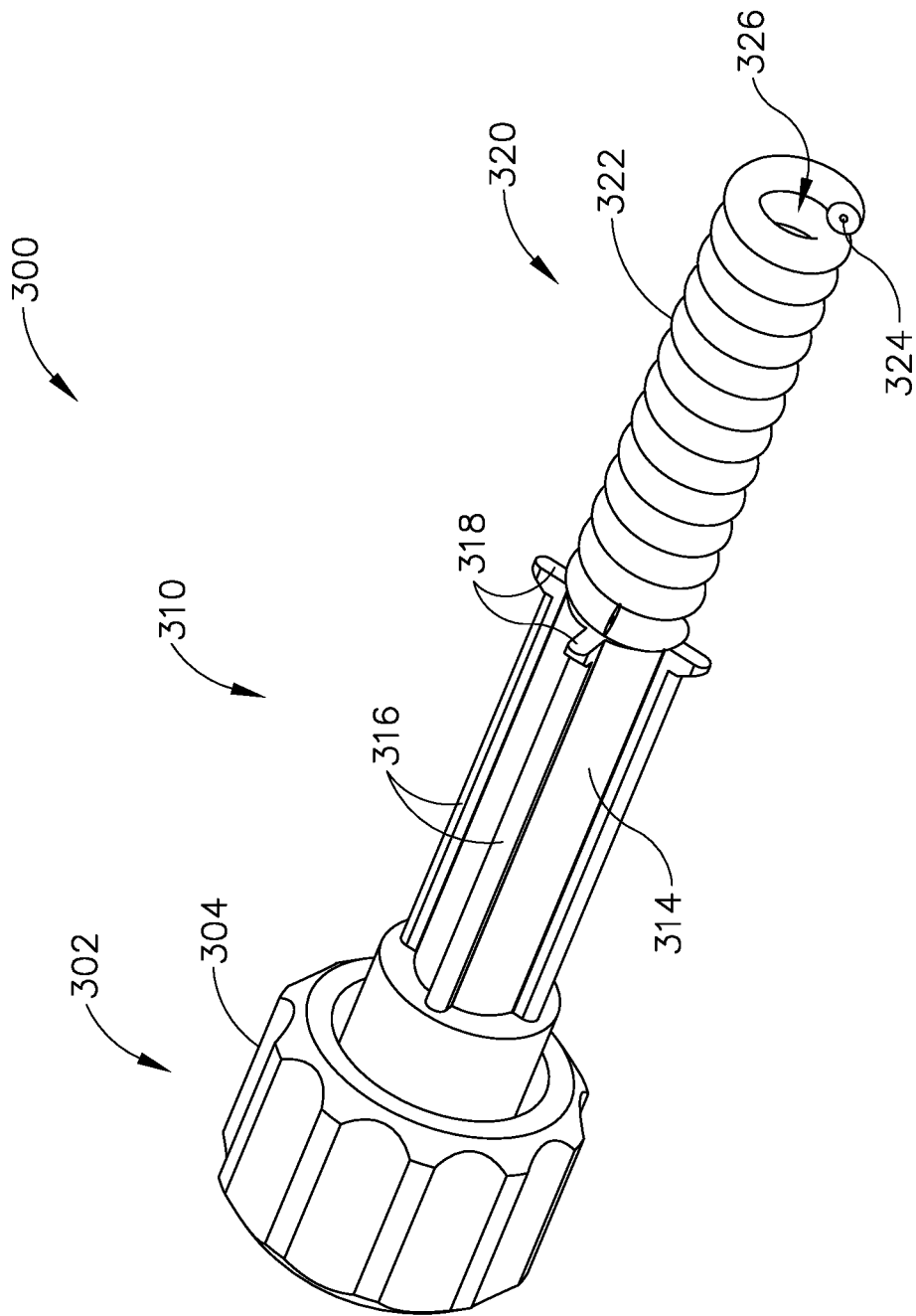
FIG. 5 depicts a perspective view of an exemplary cleaning device that may be used to clean the end effector and shaft assembly of FIG. 2.
Figure 6:
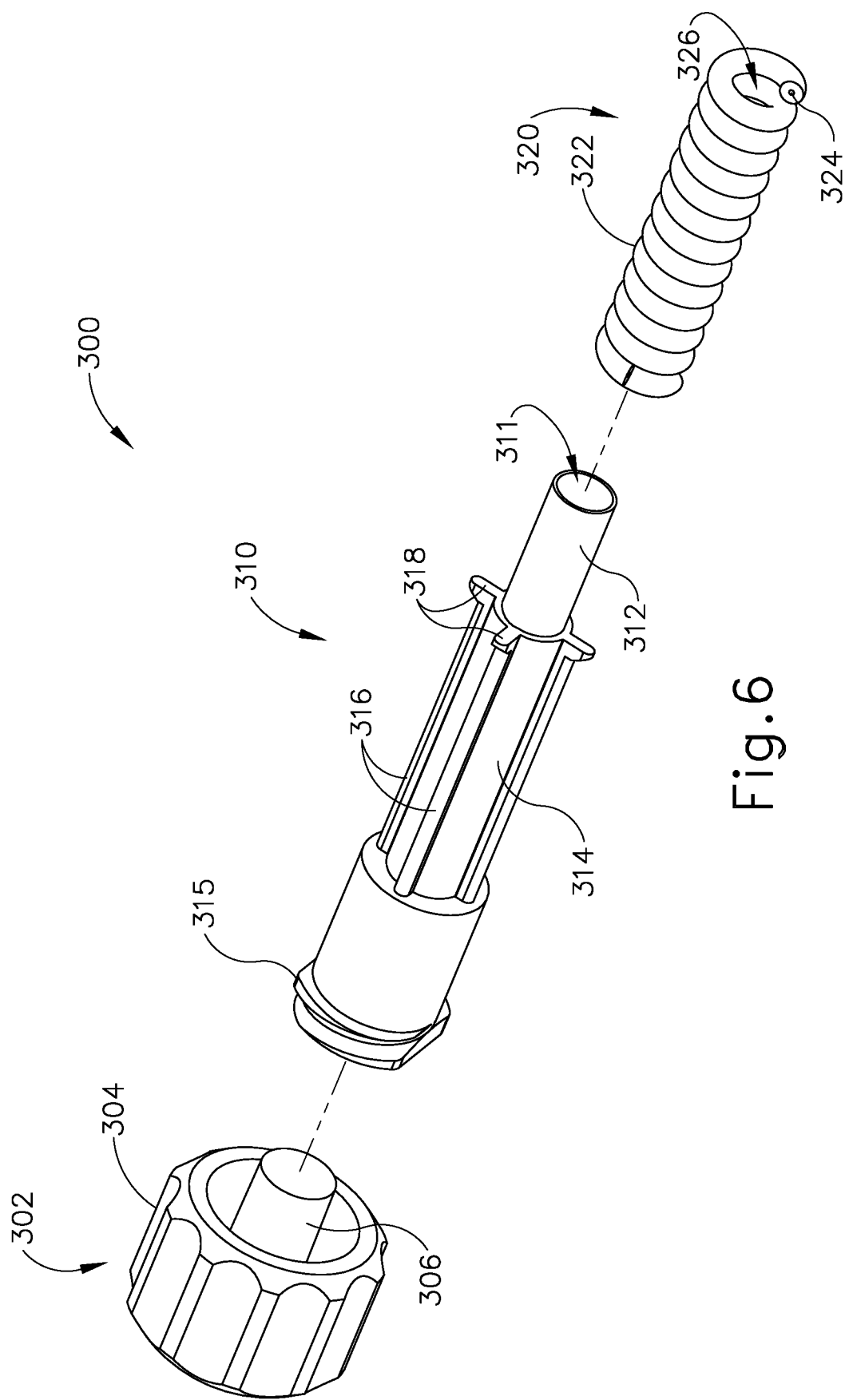
FIG. 6 depicts an exploded perspective view of the cleaning device of FIG. 5.

FIGS. 5-10B show an exemplary detachable cleaning device (300) that may be used to clean portions of end effector (180) and shaft assembly (150) of instrument (10). As best seen in FIGS. 5-6, cleaning device (300) includes a handle assembly (310), a brush assembly (320), and a removable cap (302).

Handle assembly (310) includes a luer fitting (315), a flexible handle (314), and a flexible shaft (312). Flexible handle (314) extends from luer fitting (315) while flexible shaft (312) extends from flexible handle (314). Luer fitting (315), flexible handle (314), and flexible shaft (312) may be unitarily connected. Alternatively, luer fitting (315), flexible handle (314), and flexible shaft (312) may be connected by an interference fit or any suitable manner apparent to one having ordinary skill in the art in view of the teachings herein. Flexible shaft (312) is dimensioned to receive the outer diameters of ultrasonic blade (190) and waveguide (192). However, flexible shaft (312) is also dimensioned to fit within the inner diameters of distally projecting tongues (154, 172) and inner tube (170).

A plurality of protrusions (316) extend along the length of flexible handle (314) and terminate into a plurality of stops (318). Protrusions (316) may be grasped by an operator in order to manipulate handle assembly (310) in various ways, such as rotating handle assembly (310) about its own longitudinal axis. Stops (318) may contact brush assembly (320) to prevent brush assembly (320) from moving proximally along the length of flexible handle (314).

Luer fitting (315), flexible handle (314) and flexible shaft (312) together define a lumen (311). Lumen (311) is dimensioned to receive ultrasonic blade (190). Flexible handle (314) and flexible shaft (312) have sufficient resilient flexibility in order to conform to the contours of ultrasonic blade (190) in versions where blade (190) has a curved longitudinal profile. Lumen (311) may have a varying diameter along the length of handle assembly (310). Alternatively, lumen (311) may have a uniform diameter along the length of handle assembly (310). As will be described in greater detail below, lumen (311) may provide fluid communication from a fluid source to selected portions of end effector (180) and shaft assembly (150). Luer fitting (315) is thus configured to attach a fluid source with lumen (311) of handle assembly (310).

Figure 7:
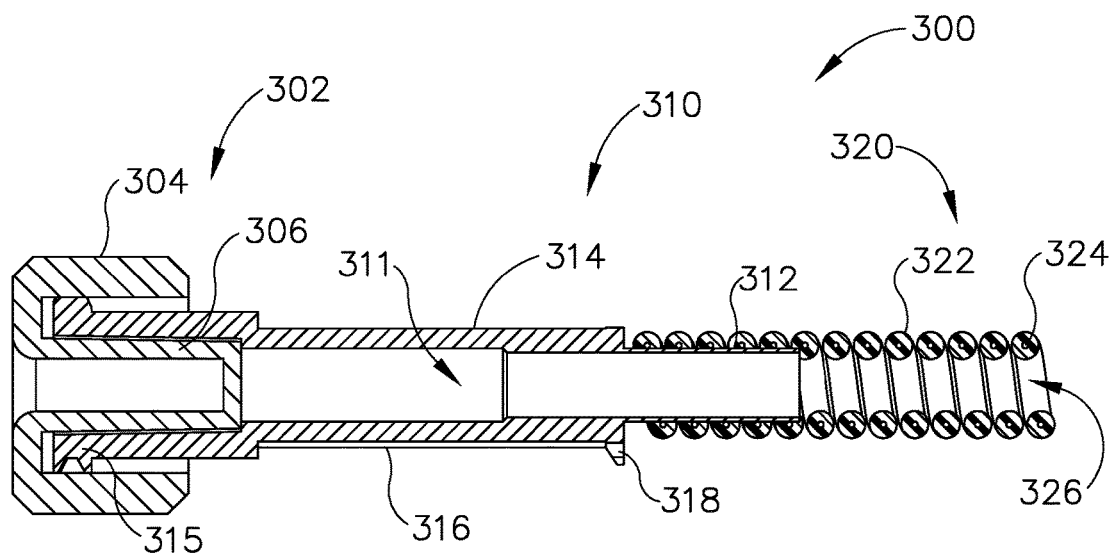
FIG. 7 depicts a side cross-sectional view of the cleaning device of FIG. 5.
Figure 8:
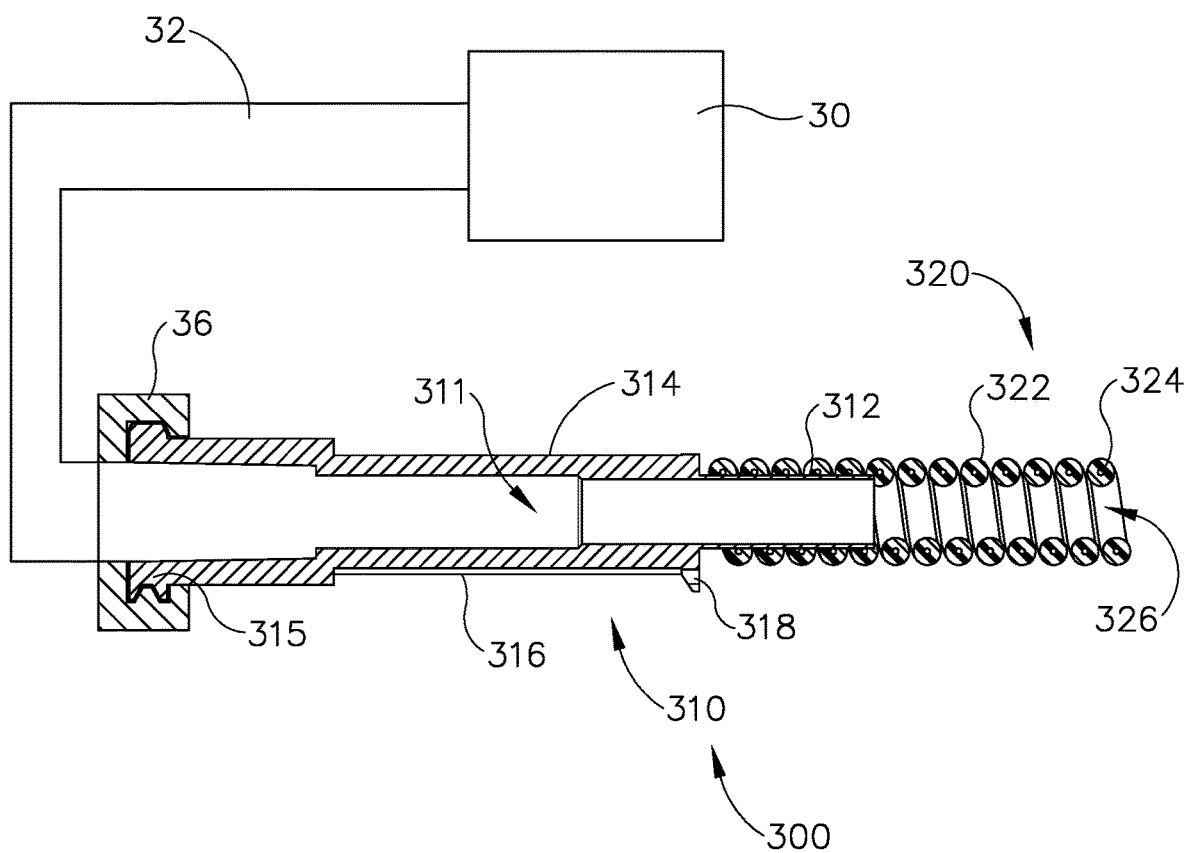
FIG. 8 depicts a side cross-sectional view of the cleaning device of FIG. 5, where the cleaning device is connected to a simple luer fitting and a fluid source.
Figure 10A:
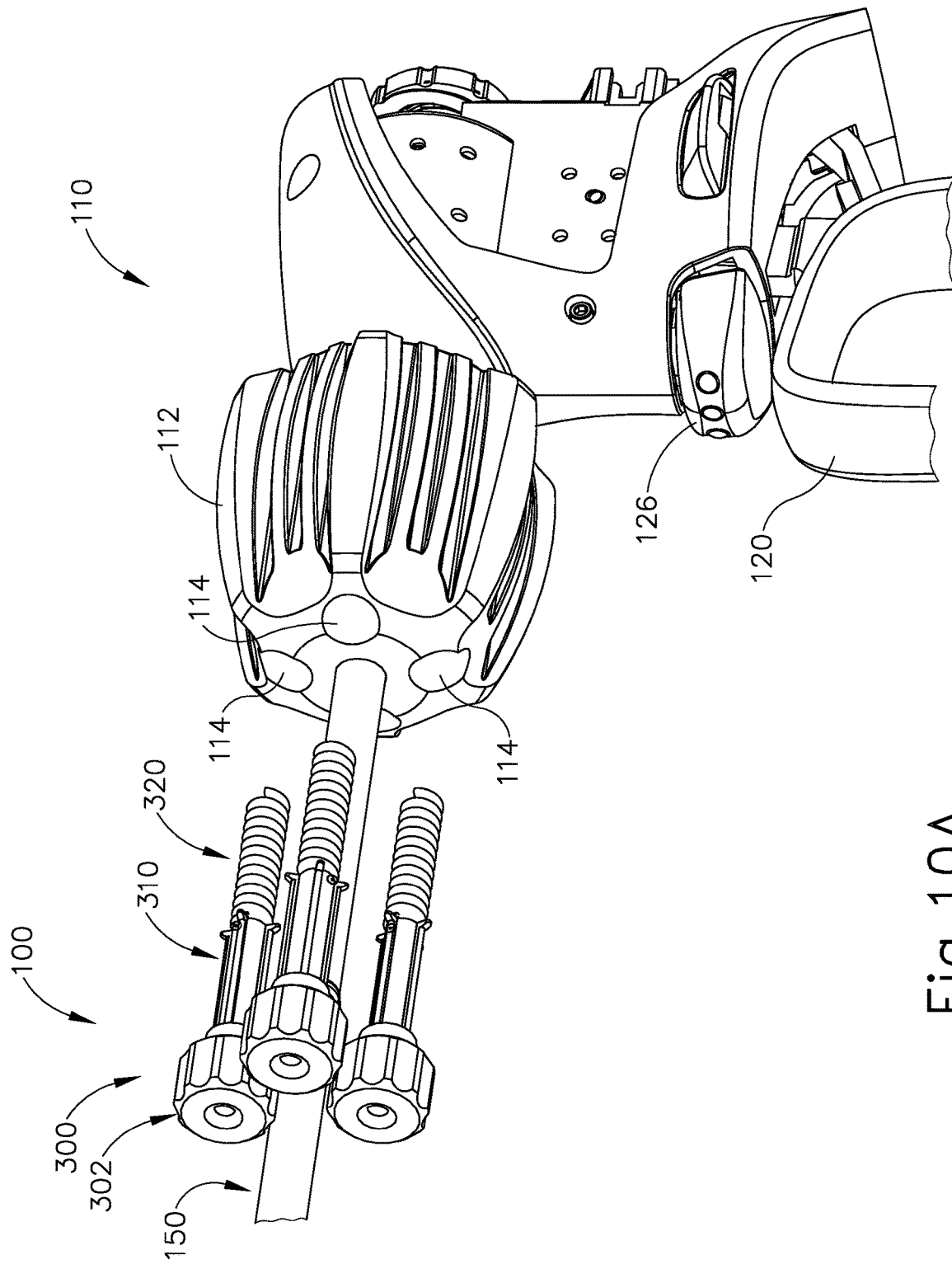
FIG. 10A depicts a perspective view of an exemplary disposable assembly that may be incorporated into the ultrasonic instrument of FIG. 1, with three cleaning brushes of FIG. 5 removed from the disposable assembly.
Figure 10B:
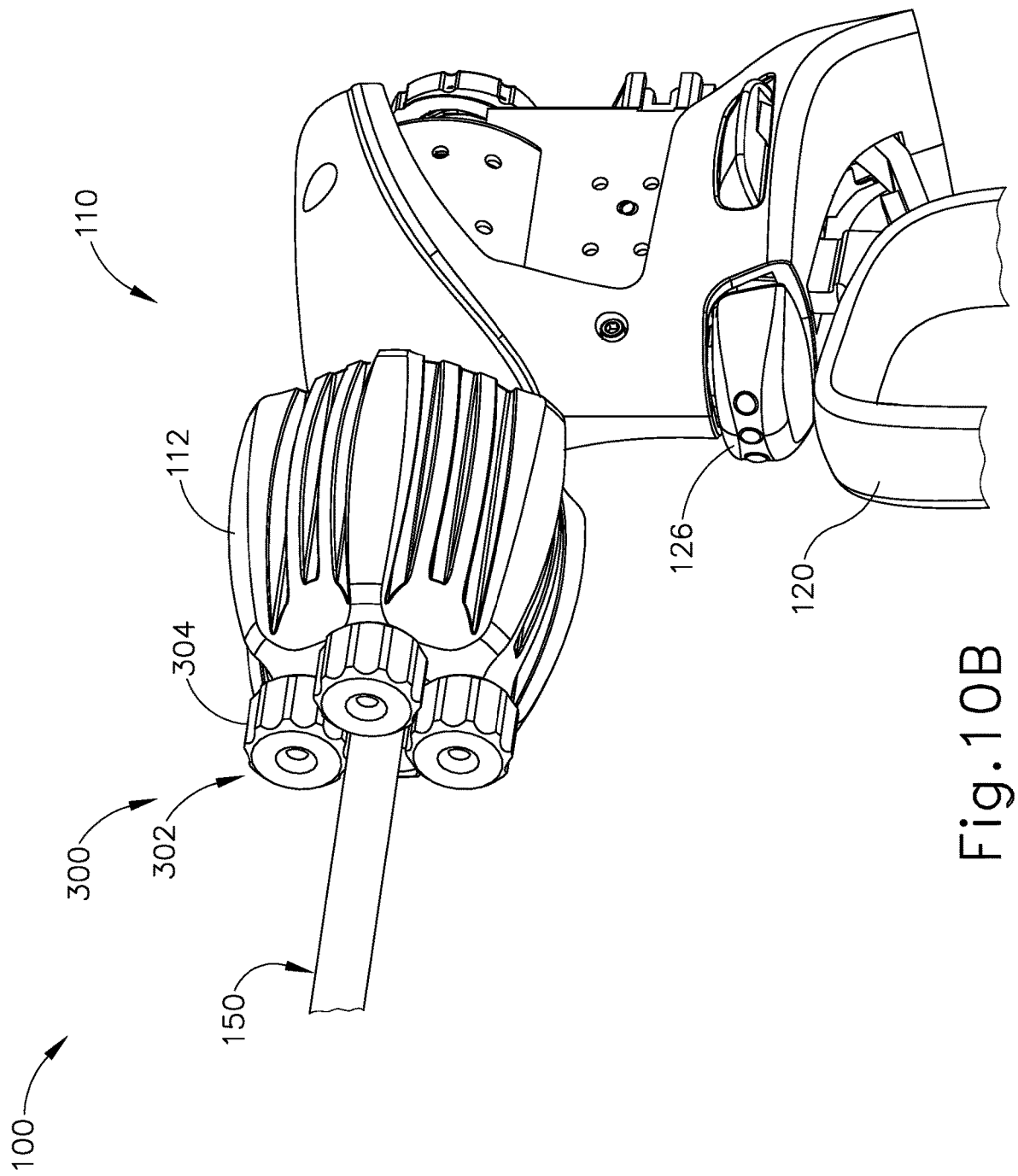
FIG. 10B depicts a perspective view of the disposable assembly of FIG. 10A, with the three cleaning brushes housed within the disposable assembly.

Removable cap (302) includes a grip (304) and a plug (306). Plug (306) is dimensioned for an interference fit with the portion of lumen (311) defined by luer fitting (315). As best seen in FIGS. 7-8, removable cap (302) may be removed from the rest of handle assembly (310). The interference fit between cap (302) and flexible handle (314) enables an operator to remove assembled cleaning device (300) from rotation knob (112) of instrument (10) by pulling grip (304) of cap (302), without removing cap (302) from the rest of cleaning device (300), as shown in FIG. 10A-10B; but weak enough to allow an operator to later remove cap (302) from the rest of cleaning device (300) after cleaning device (300) has been pulled from rotation knob (112). Attentively, plug (306) may comprise external threading while the portion of lumen (311) defined by luer fitting (315) may comprise complementary internal threading. Therefore, an operator may be able to remove assembled cleaning device (300) from rotation knob (112) by pulling cap (302); and then remove cap (302) form the rest of cleaning device (300) by rotating cap (302) relative to handle assembly (310). Removable cap (302) may be selectively connected to handle assembly (320) in any other suitable manner as would be apparent to one having ordinary skill in the art in view of the teachings herein.

Brush assembly (320) includes a brush body (322) wrapped around a wire (324). Wire (324) and brush body (322) form a helical shape in order to define a tunnel (326). As seen in FIGS. 7-9B, wire (324) is dimensioned to fit over the outer diameter of flexible shaft (312). A portion of brush assembly (320) is connected to handle assembly (310) via an interference fit between wire (324) and flexible shaft (312). Therefore, a portion of brush body (322) is also connected to handle assembly (310). However, brush assembly (320) may be connected to handle assembly (310) by any other suitable manner that would be apparent to one having ordinary skill in the art.

As will be described in greater detail below, brush assembly (320) is dimensioned to receive blade (190) and portions of waveguide (192) within tunnel (326) while fitting within the inner diameter of inner tube (170) and distally projecting tongues (154, 172). Wire (324) may have sufficient resilient flexibility in order to conform to the contours of ultrasonic blade (190) in versions where blade (190) has a curved longitudinal profile. Brush body (322) is sufficiently resilient to compress within tight spaces and later return to its original shape when exiting tight spaces.

Brush body (322) includes a plurality of bristles (not shown). Such bristles may have any suitable degree of stiffness. Brush body (322) may have sufficient abrasive qualities to remove surgical debris caked onto the outer diameters of blade (190) and waveguide (192), as well as surgical debris caked onto the inner diameters of distally projecting tongues (152, 172) and inner tube (170). Brush body (322) may be made of any suitable material known to one having ordinary skill in the art in view of the teachings herein.

As mentioned above, cap (302) may be selectively removed from luer fitting (315). Luer fitting (315) may also couple to a fluid source. FIG. 8 shows cap (302) removed from handle assembly (310) while luer fitting (315) is coupled to a fluid source (30) via a conduit (32) and a luer attachment (36). Fluid source (30) may be a fluid filled syringe, a pump, or any other suitable fluid source as will be apparent to one having ordinary skill in the art in view of the teachings herein. Luer attachment (36) may provide a fluid tight seal with luer fitting (315). Fluid may thus travel from fluid source (30), through conduit (32) and lumen (311) to exit the end of lumen (311) defined by flexible shaft (312). As will be described in greater detail below, cleaning device (300) may be inserted within a distal portion of shaft assembly (150) in order for brush body (322) to remove excess debris. If cleaning device (300) is inserted within shaft assembly (150), fluid may be delivered within shaft assembly (150) to flush out excess debris removed from the outer diameters of blade (190) and waveguide (192), as well as excess debris removed from the inner diameters of distally projecting tongues (152, 172) and inner tube (170).

Figure 9A:
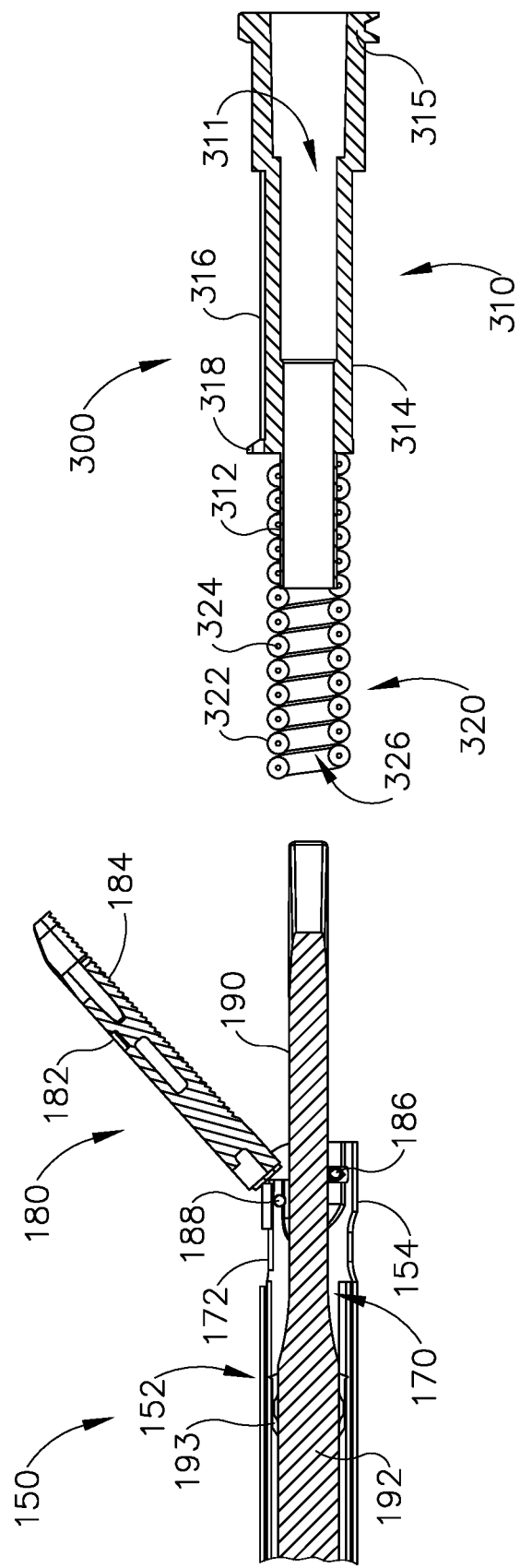
FIG. 9A depicts a side cross-sectional view of the cleaning device of FIG. 5 separated from the end effector and shaft assembly of FIG. 2, with the end effector in the open configuration.
Figure 9B:
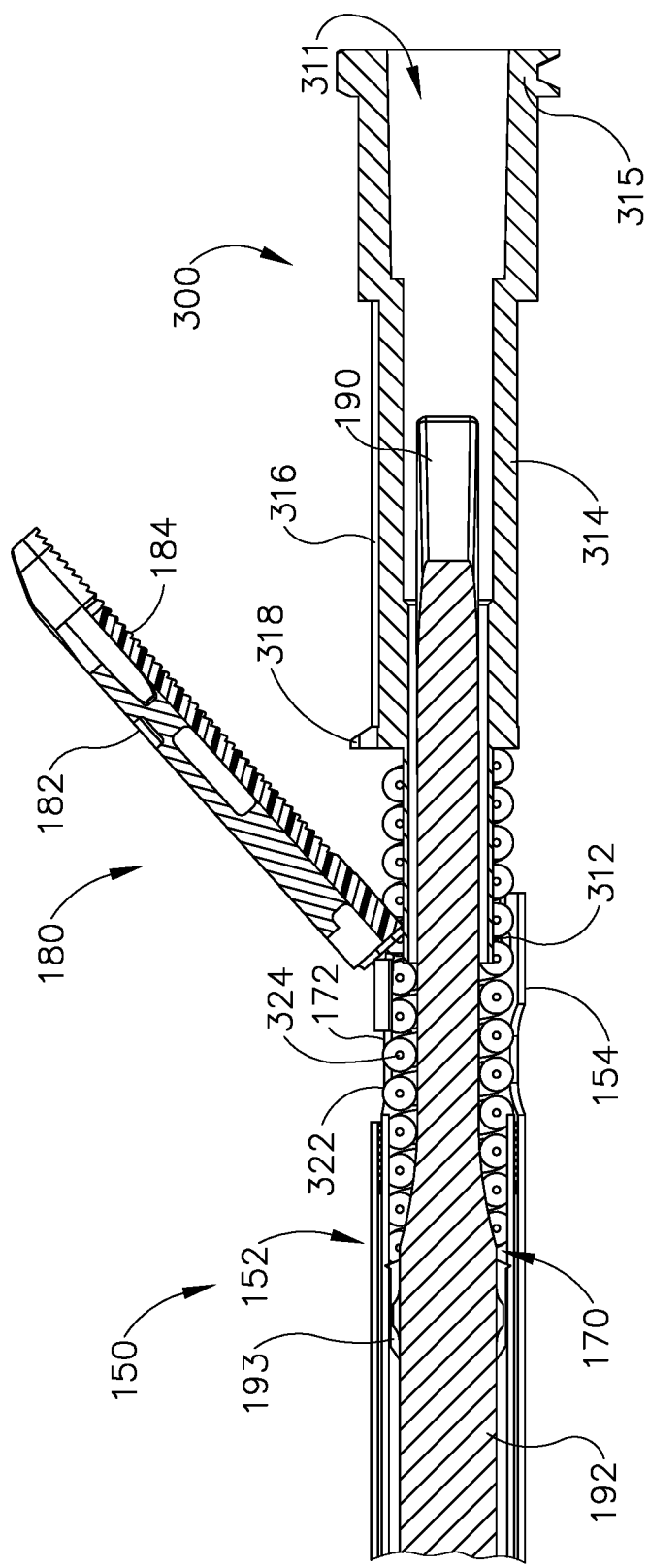
FIG. 9B depicts a side cross-sectional view of the cleaning device of FIG. 5 inserted within the end effector and shaft assembly of FIG. 2, with the end effector in the open configuration.

FIGS. 9A-9B show cleaning device (300) being inserted over the outer diameters of ultrasonic blade (190) and acoustic waveguide (192) and within the inner diameters of distally projecting tongues (154, 172) and inner tube (170). As mentioned above, brush assembly (320), flexible handle (314), and flexible shaft (312) all have sufficient flexibility and rigidity in order to conform to the contours of ultrasonic blade (190) in versions where blade (190) has a curved longitudinal profile. Therefore, while blade (190) is shown as having a straight longitudinal profile, cleaning device (300) is also capable of working with a curved ultrasonic blade (190).

With flexible shaft (312) and brush assembly (320) inserted within shaft assembly (150), as shown in FIG. 9B, an operator may twist cleaning device (300) about its longitudinal axis by gripping flexible handle (314) and protrusions (316). An operator may also actuate cleaning device (300) toward and away from proximal seal (193) in a longitudinally reciprocating motion to encourage contact between brush body (322) and surrounding components. Due to brush body (322) being sufficiently resilient to compress within tight spaces and later return to its original shape out of tight spaces, brush body (322) may make contact with the outer diameters of blade (190) and waveguide (192) while also making contact with the inner diameters of distally projecting tongues (152, 172) and inner tube (170). Additionally, due to brush body (322) having abrasive qualities, contact made by brush body (322) may remove debris caked onto the outer diameters of blade (190) and waveguide (192); and remove debris caked onto the inner diameters of distally projecting tongues (152, 172) and inner tube (170). An operator may then attach fluid source (30) to cleaning device (300) via luer attachment (36) and luer fitting (315), as shown in FIG. 8, to deliver fluid to wash out removed debris.

As best shown in FIGS. 10A-10B, rotation knob (112) includes a plurality of recesses (114) designed to removably house multiple cleaning devices (300), providing a convenient location for the operator to access cleaning devices (300). While the current example shows knob (112) housing cleaning devices (300), it is envisioned that knob (112) may have recesses (114) dimensioned to house any of the detachable cleaning devices described below. While three cleaning devices (300) and three recesses (114) are shown in the current example, any number of cleaning devices (300) may be housed within rotation knob (112) with any number of corresponding recesses (114) as would be apparent to one having ordinary skill in the art. While recesses (114) are located on rotation knob (112) in the present example, it should be understood that recesses (114) may be located at any other suitable location on instrument (10) that would be apparent to a person having ordinary skill in the art.

Because there are multiple cleaning devices (300) located on knob (112), an operator may be encouraged to discard a specific cleaning device (300) after one use. Additionally, cleaning device (300) may have a feature on flexible handle (310) to prevent or discourage reassembly of a removed cleaning device (300) back into recess (114). As mentioned above, cleaning devices (300) may be used during a surgical procedure or between surgical procedures. If cleaning devices (300) are primarily to be used in between surgical procedures, the number of cleaning devices on knob (112) may indicate the number of surgical procedures that disposable assembly (100) may be used.

2. Exemplary Cleaning Device with Brush Woven into Shaft

Figure 11:
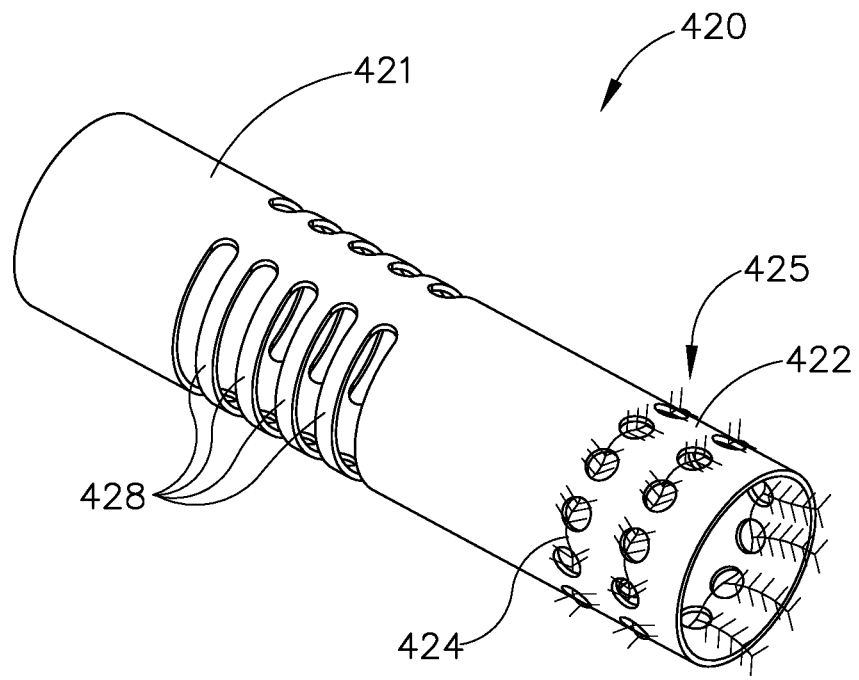
FIG. 11 depicts a perspective view of an alternative cleaning device that may be used to clean the end effector and shaft assembly of FIG. 2.

FIG. 11 shows an alternative brush assembly (400) that may be incorporated at the end of flexible shaft (312). Brush assembly (400) of this example includes a hollow shaft (421) having flexible ribs (428). Flexible ribs (428) allow hollow shaft (421) to have sufficient resilient flexibility such that hollow shaft (421) may conform to the contours of ultrasonic blade (190) in versions where blade (190) has a curved longitudinal profile. Hollow shaft (421) may extend from flexible shaft (312) in such a way as to continue to define lumen (311). Hollow shaft (421) is thus dimensioned to receive ultrasonic blade (190) and waveguide (192). Additionally, and similar to flexible shaft (312), hollow shaft (421) is dimensioned to fit within distally projecting tongues (154, 172) and inner tube (170). Hollow shaft (421) may also partially define lumen (311) for providing fluid communication from a fluid source to selected portions of end effector (180) and shaft assembly (150) as described above.

Hollow shaft (421) also defines a plurality of apertures (425). Apertures (425) house a wire (424) weaving in and out of apertures (425). Wire (424) has a plurality of bristles (422) extending radially outwardly from wire (424). Bristles (422) are exposed within the inner diameter and outer diameter of hollow shaft (421). Bristles (422) are sufficiently resilient to compress within tight spaces and later return to its original shape when exiting tight spaces. Additionally, bristles (422) may have sufficient abrasive qualities to remove surgical debris caked onto the outer diameters of blade (190) and waveguide (192), as well as surgical debris caked onto the inner diameters of distally projecting tongues (152, 172) and inner tube (170). Bristles (422) may be made of any suitable material known to one having ordinary skill in the art in view of the teachings herein.

As mentioned above, bristles (422) are exposed to the inner diameter and the outer diameter of hollow shaft (421). Additionally, hollow shaft (421) is dimensioned to fit around the outer diameters of blade (190) and waveguide (192); and to fit within the inner diameters of distally projecting tongues (154, 172) and inner tube (170). Therefore, an operator may insert hollow shaft (421) over blade (190) and waveguide (192), and within distally projecting tongues (154, 172) and inner tube (170), while the abrasive qualities of bristles (422) may help remove surgical debris caked onto blade (190), waveguide (192), distally projecting tongues (152, 172), and inner tube (170).

Hollow shaft (421) may be unitarily fixed to flexible shaft (312). Alternatively, hollow shaft (421) may be dimensioned for an interference fit with flexible shaft (312). Hollow shaft (421) may be fixed relative to flexible shaft (312) in any suitable manner apparent to one having ordinary skill in the art in view of the teachings herein.

3. Exemplary Cleaning Device with Brush Wrapping Around and into Shaft

Figure 12:
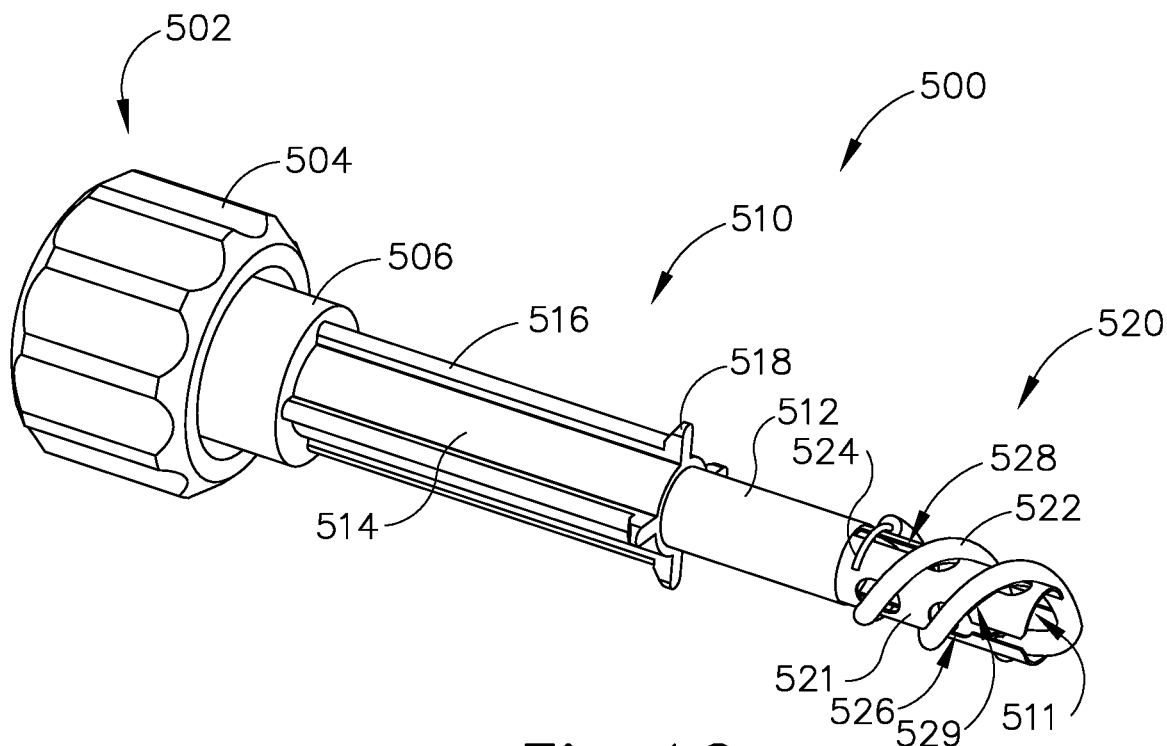
FIG. 12 depicts a perspective view of another alternative cleaning device that may be used to clean the end effector and shaft assembly of FIG. 2.
Figure 13:
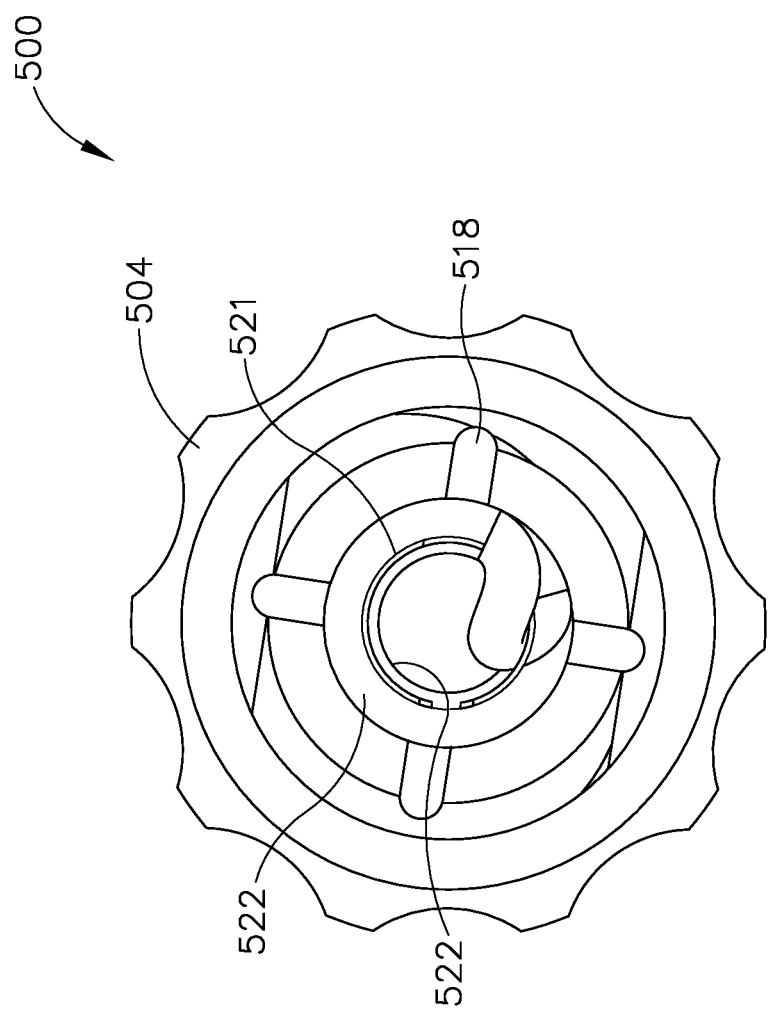
FIG. 13 depicts a front elevational view of the cleaning device of FIG. 12.
Figure 14:
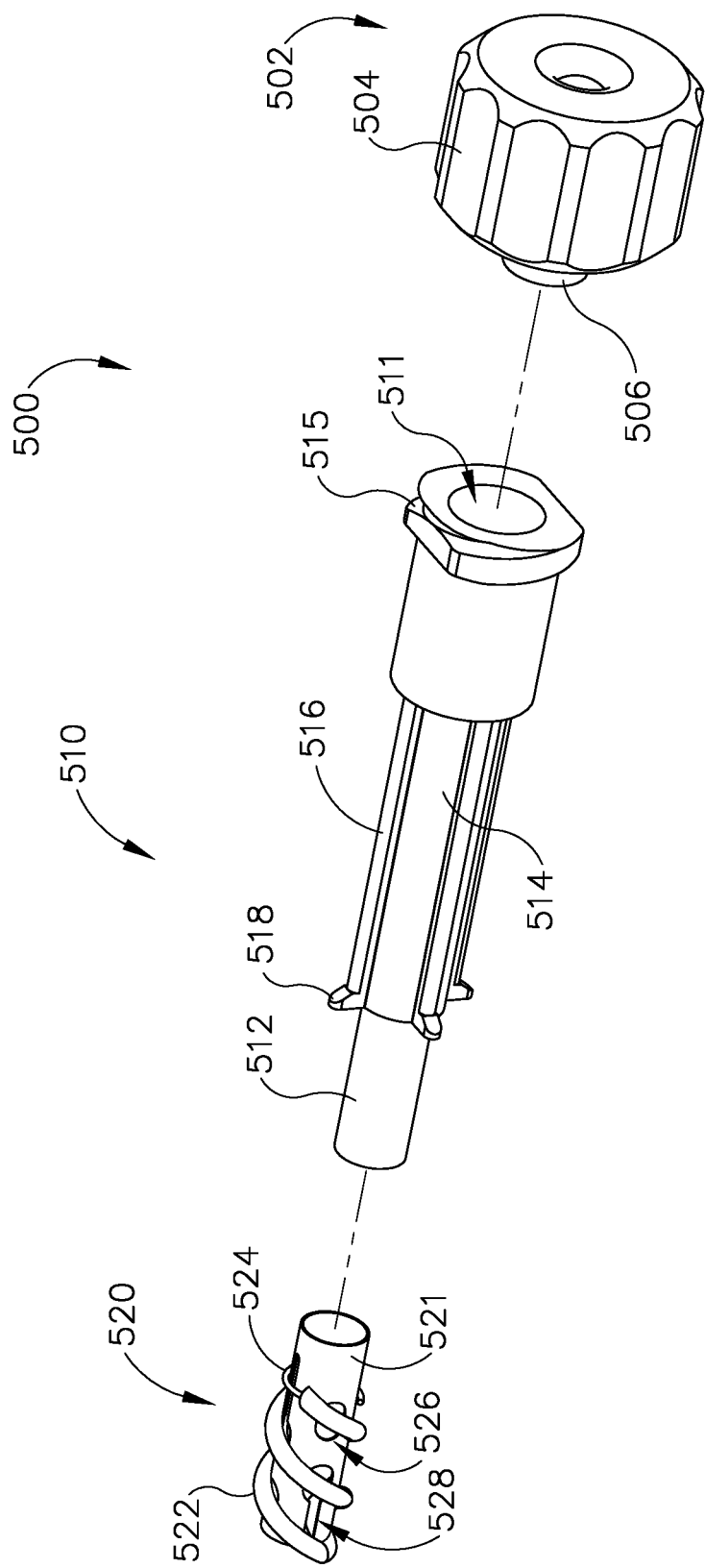
FIG. 14 depicts an exploded perspective view of the cleaning device of FIG. 12.

FIGS. 12-18 show another exemplary cleaning device that may be used and stored within instrument (10). As best seen in FIGS. 12 and 14, cleaning device (500) includes a handle assembly (510), a brush assembly (520), and a removable cap (502). Handle assembly (510) is substantially similar to handle assembly (310) mentioned above. Handle assembly (510) thus includes a flexible shaft (512), flexible handle (514), a plurality of projections (516), a plurality of stops (518), and a luer fitting (515). These components are all substantially similar to flexible shaft (312), flexible handle (314), plurality of projections (316), plurality of stops (318), and luer fitting (315) described above, respectively. Handle assembly (510) defines a lumen (511) that may provide fluid communication from a fluid source to selected portions of end effector (180) and shaft assembly (150) as described above.

Flexible shaft (512) is dimensioned to receive the outer diameters of ultrasonic blade (190) and waveguide (192). However, flexible shaft (512) is also dimensioned to fit within the inner diameters of distally projecting tongues (154, 172) and inner tube (170).

Removable cap (502) is substantially similar to removable cap (302) described above. Therefore, removable cap (502) includes grips (504) and plug (506), which are substantially similar to grips (304) and plug (306) described above, respectively.

Figure 15:
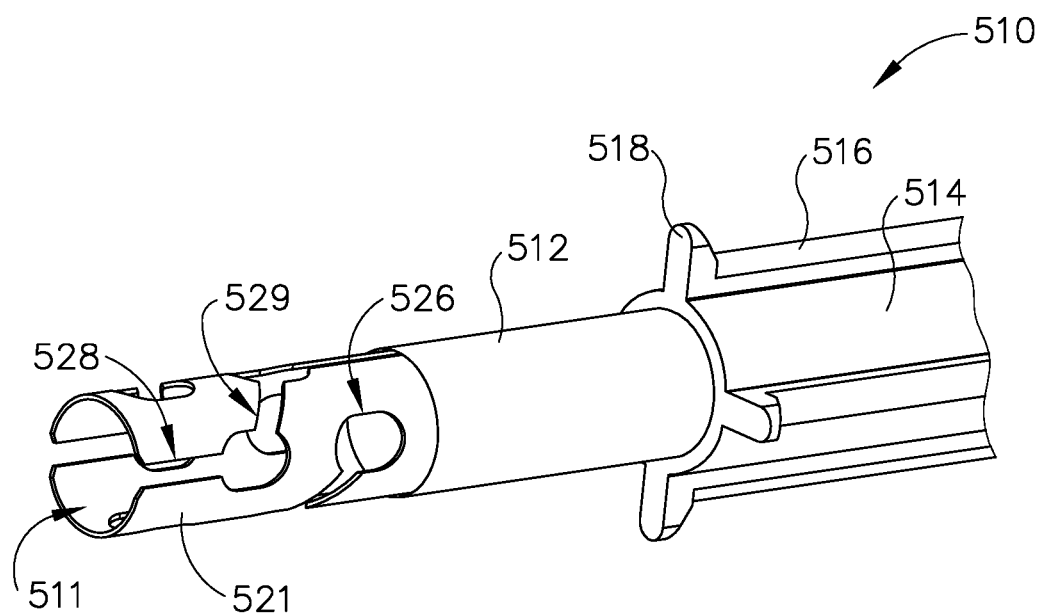
FIG. 15 depicts a perspective view of the cleaning device of FIG. 12, with a bristle section omitted.
Figure 16:
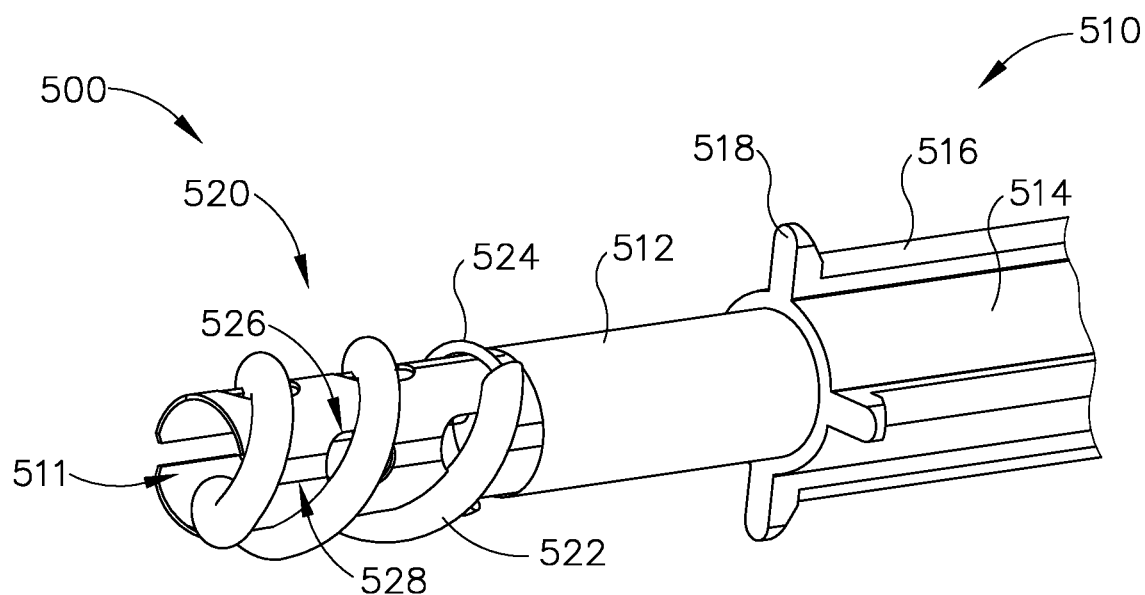
FIG. 16 depicts a perspective view of the cleaning device of FIG. 12, with the bristle section included.

Brush assembly (520) includes a brush body (522) wrapped around a wire (524) and a hollow shaft (521). As best seen in FIG. 15, hollow shaft (521) defines a plurality of recesses (526), a plurality of axial slots (528), and a plurality of diagonal slots (529). Recesses (526), axial slots (528) and diagonal slots (529) may help hollow shaft (521) provide sufficient resilient flexibility such that hollow shaft (521) may conform to the contours of ultrasonic blade (190) in versions where blade (190) has a curved longitudinal profile.

Hollow shaft (521) extends from flexible shaft (512) in such a way as to continue to define lumen (511). Hollow shaft (521) is thus dimensioned to receive ultrasonic blade (190) and waveguide (192). Additionally, and similar to flexible shaft (512), hollow shaft (521) is dimensioned to fit within distally projecting tongues (154, 172) and inner tube (170). Hollow shaft (521) also partially defines lumen (511) for providing fluid communication from a fluid source to selected portions of end effector (180) and shaft assembly (150) as described above. Hollow shaft (521) may be unitarily fixed to flexible shaft (512). Alternatively, hollow shaft (521) may be dimensioned for an interference fit with flexible shaft (512). Hollow shaft (521) may be fixed relative to flexible shaft (512) in any suitable manner apparent to one having ordinary skill in the art in view of the teachings herein.

Brush body (522) includes a plurality of bristles (not shown). Such bristles may have any suitable degree of stiffness. Brush body (522) is sufficiently resilient to compress within tight spaces and later return to its original shape when exiting tight spaces. Brush body (522) may have sufficient abrasive qualities to remove surgical debris caked onto the outer diameters of blade (190) and waveguide (192), as well as surgical debris caked onto the inner diameters of distally projecting tongues (152, 172) and inner tube (170). Brush body (522) may be made of any suitable material known to one having ordinary skill in the art in view of the teachings herein.

Figure 17:
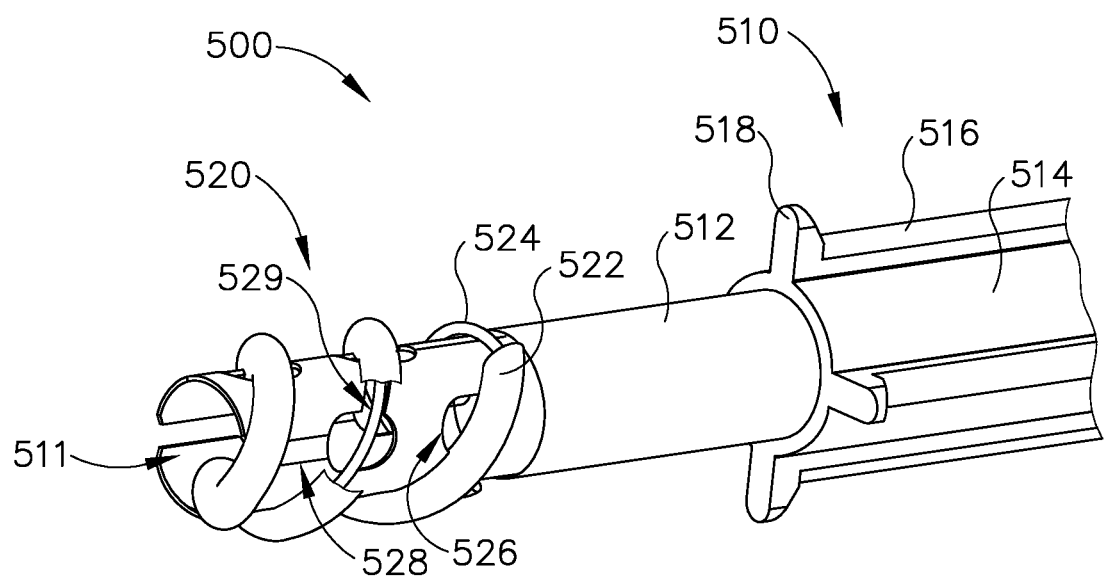
FIG. 17 depicts a perspective view of the cleaning device of FIG. 12, with the bristle section shown in transparency for further detail.
Figure 18:
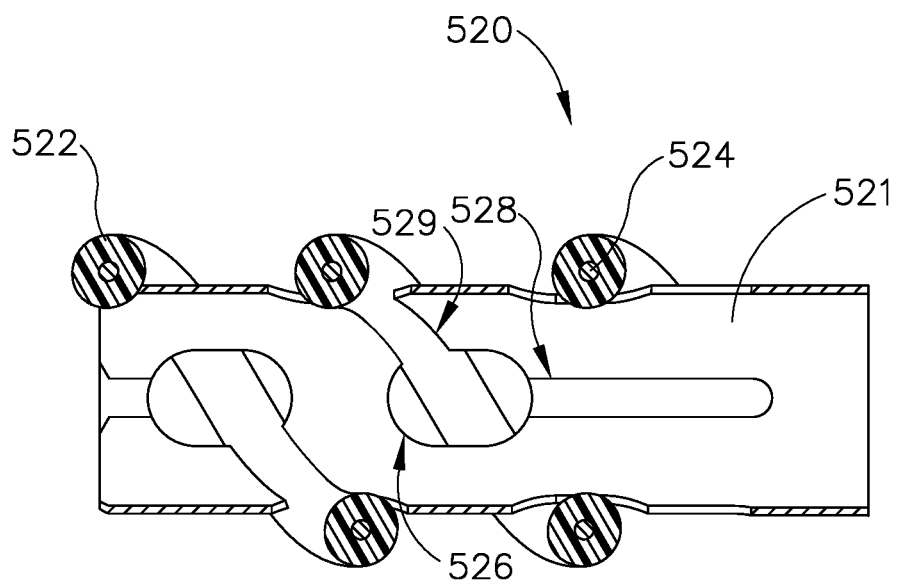
FIG. 18 depicts a cross-sectional side view of the proximal end of the cleaning device of FIG. 12.

As best seen in FIGS. 17-18, brush body (522) and wire (524) wrap around the outer diameter of hollow shaft (521) in such a way that brush body (522) and wire (524) partially rest within both apertures (526) and diagonal slots (529). Brush body (522) is wrapped around aperture (526) and diagonal slots (529) with sufficient force to compress portions of brush body (522) within aperture (526) and diagonal slots (529). Thus, as best seen in FIGS. 13 and 18, a portion of brush body (522) is exposed adjacent to the inner diameter of hollow shaft (521) as well as the outer diameter of hollow shaft (521). As mentioned above, hollow shaft (521) is dimensioned to fit around the outer diameters of blade (190) and waveguide (192); and to fit within the inner diameters of distally projecting tongues (154, 172) and inner tube (170). An operator may thus insert hollow shaft (421) over blade (190) and waveguide (192) and within distally projecting tongues (153, 172) and inner tube (170), and the abrasive qualities of brush body (522) may help remove surgical debris caked onto blade (190), waveguide (192), distally projecting tongues (152, 172) and inner tube (170).

Figure 19:
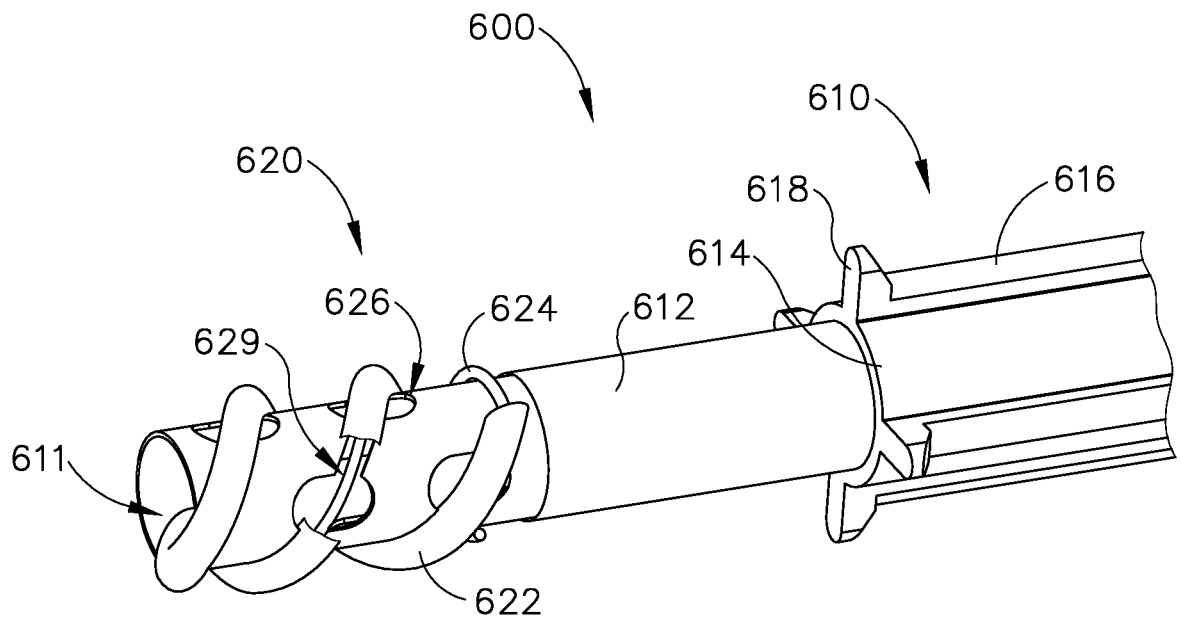
FIG. 19 depicts a perspective view of a portion of another alternative cleaning device that may be used to clean the end effector and shaft assembly of FIG. 2.

FIG. 19 shows another exemplary cleaning device (600) that may be used and stored within instrument (10). Cleaning device (600) includes a handle assembly (610) and a brush assembly (620). Cleaning device (600) may also include a cap (not shown) that is substantially similar to cap (302, 502) described above. Handle assembly (610) includes a flexible shaft (612), flexible handle (614), a plurality of protrusions (616), a plurality of stops (618) and a luer fitting (not shown) substantially similar to flexible shaft (512), flexible handle (514), plurality of protrusions (516), plurality of stops (518) and luer fitting (515) described above. Handle assembly (610) defines a lumen (611) that is substantially similar to lumen (511) described above.

Flexible shaft (612) is dimensioned to receive the outer diameters of ultrasonic blade (190) and waveguide (192). Flexible shaft (612) is also dimensioned to fit within the inner diameters of distally projecting tongues (154, 172) and inner tube (170).

Brush assembly (620) includes a brush body (622), a wire (624), a plurality of recesses (626) and a plurality of diagonal slots (629), all substantially similar to brush body (522), wire (524), plurality of recesses (526) and plurality of diagonal slots (529) mentioned above. However, the only difference between brush assembly (620) and brush assembly (520) described above is that brush assembly (620) does not have a plurality of axial slots (528).

4. Exemplary Cleaning Device with Axially Extending Brushes

Figure 20:
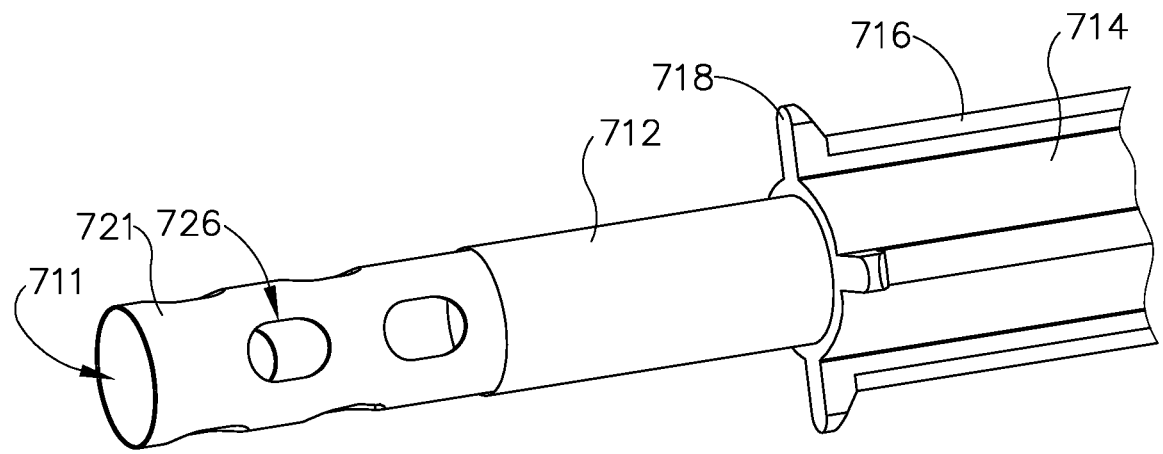
FIG. 20 depicts perspective view of a portion of another alternative cleaning device that may be used to clean the end effector and shaft assembly of FIG. 2, with a bristle section omitted.
Figure 21:
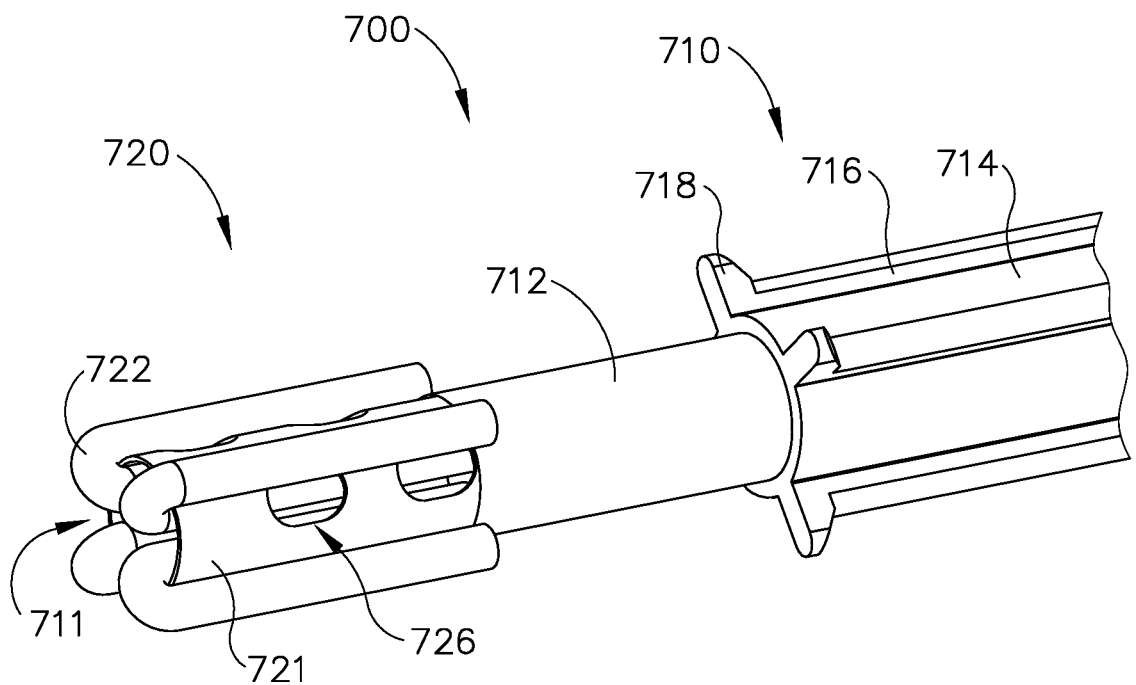
FIG. 21 depicts a perspective view of the cleaning device of FIG. 20, with the bristle section included.
Figure 22:
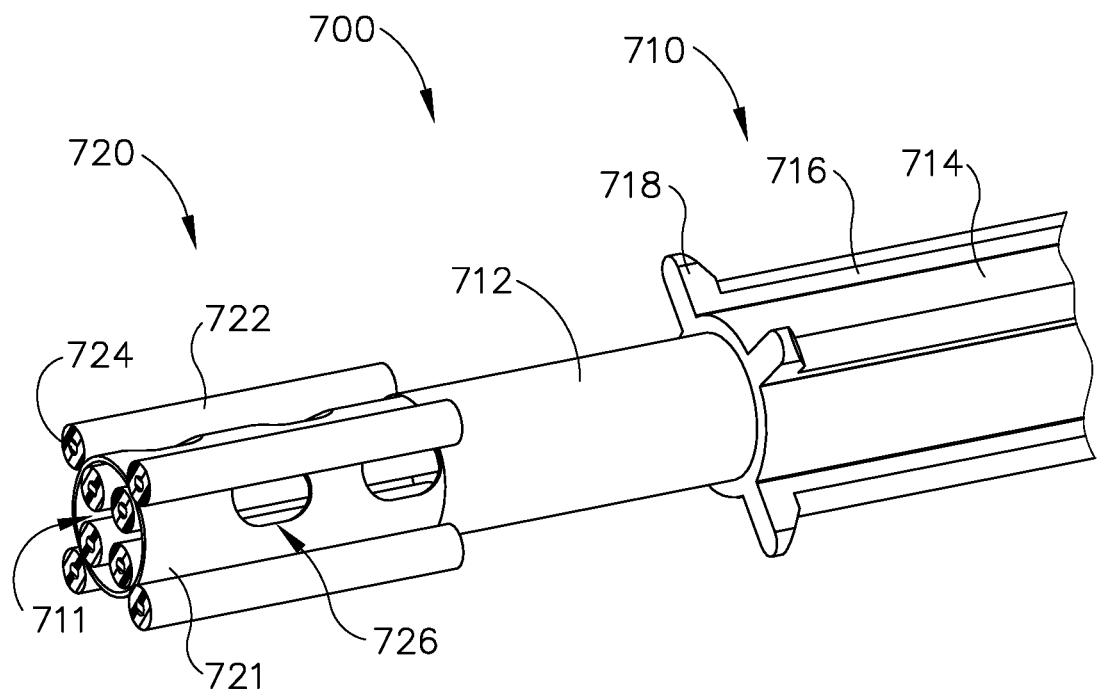
FIG. 22 depicts a perspective cross-sectional view of the cleaning device of FIG. 20.

FIGS. 20-22 show another exemplary cleaning device (700) that may be used and stored within instrument (10). As best seen in FIGS. 21-22, cleaning device (700) includes a handle assembly (710), a brush assembly (720), and a removable cap (not shown). Handle assembly (710) is substantially similar to handle assembly (310, 510) mentioned above. Handle assembly (710) thus includes a flexible shaft (712), flexible handle (714), a plurality of projections (716), a plurality of stops (718), and a luer fitting (not shown). These components are all substantially similar to flexible shaft (312, 512), flexible handle (314, 514), plurality of projections (316, 516), plurality of stops (318, 518), and luer fitting (315, 515) described above, respectively. Handle assembly (710) defines a lumen (711) that may provide fluid communication from a fluid source to selected portions of end effector (180) and shaft assembly (150) as described above.

Flexible shaft (712) is dimensioned to receive the outer diameters of ultrasonic blade (190) and waveguide (192). However, flexible shaft (712) is also dimensioned to fit within the inner diameters of distally projecting tongues (154, 172) and inner tube (170).

Brush assembly (720) includes four brush bodies (722) wrapped around four respective wires (724) and a hollow shaft (721). Each wire (724) extends longitudinally adjacent to the inner diameter and the outer diameter of hollow shaft (721) and wraps around the distal end of hollow shaft (721). Thus, a first portion of each brush body (722) is located within the inner diameter of hollow shaft (721) and a second portion of each brush body (722) is located adjacent to the outer diameter of hollow shaft (721). Brush bodies (722) and wires (724) may be fixed to the inner diameter of hollow shaft (721) or any other suitable location apparent to one having ordinary skill in the art. Hollow shaft (721) defines a plurality of recesses (726). Recesses (726) may help hollow shaft (721) provide sufficient resilient flexibility such that hollow shaft (721) may conform to the contours of ultrasonic blade (190) in versions where blade (190) has a curved longitudinal profile.

Hollow shaft (721) extends from flexible shaft (712) in such a way as to continue to define lumen (711). Hollow shaft (721) is thus dimensioned to receive ultrasonic blade (190) and waveguide (192). Additionally, and similar to flexible shaft (312, 512, 712), hollow shaft (721) is dimensioned to fit within distally projecting tongues (154, 172) and inner tube (170). Hollow shaft (721) also partially defines lumen (711) for providing fluid communication from a fluid source to selected portions of end effector (180) and shaft assembly (150) as described above. Hollow shaft (721) may be unitarily fixed to flexible shaft (712). Alternatively, hollow shaft (721) may be dimensioned for an interference fit with flexible shaft (712). Hollow shaft (721) may be fixed relative to flexible shaft (712) in any suitable manner apparent to one having ordinary skill in the art in view of the teachings herein.

Brush body (722) includes a plurality of bristles (not shown). Such bristles may have any suitable degree of stiffness. Brush body (722) is sufficiently resilient to compress within tight spaces and later return to its original shape when exiting tight spaces. Brush body (722) may have sufficient abrasive qualities to remove surgical debris caked onto the outer diameters of blade (190) and waveguide (192), as well as surgical debris caked onto the inner diameters of distally projecting tongues (152, 172) and inner tube (170). Brush body (722) may be made of any suitable material known to one having ordinary skill in the art in view of the teachings herein.

As mentioned above, brush bodies (722) and wires (724) are exposed both within the inner diameter of hollow shaft (721) and adjacent to the outer diameter of hollow shaft (721). As mentioned above, hollow shaft (721) is dimensioned to fit around the outer diameters of blade (190) and waveguide (192); and to fit within the inner diameters of distally projecting tongues (154, 172) and inner tube (170). Therefore, an operator may insert hollow shaft (721) over blade (190) and waveguide (192) and within distally projecting tongues (153, 172) and inner tube (170), and the abrasive qualities of brush body (722) may help remove surgical debris caked onto blade (190), waveguide (192), distally projecting tongues (152, 172) and inner tube (170).

Figure 23:
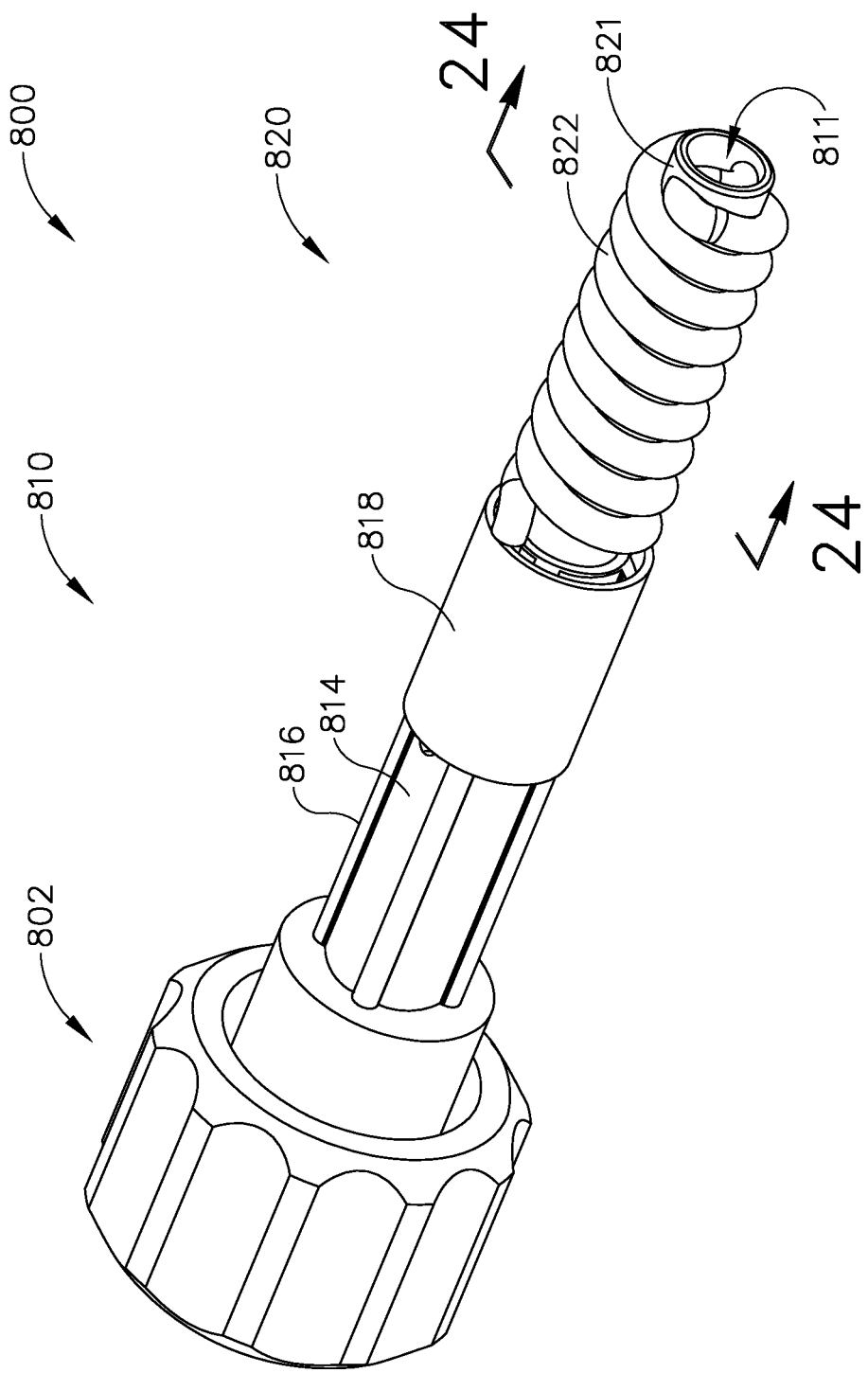
FIG. 23 depicts a perspective view of another alternative cleaning device that may be used to clean the end effector and shaft assembly of FIG. 2.
Figure 24:
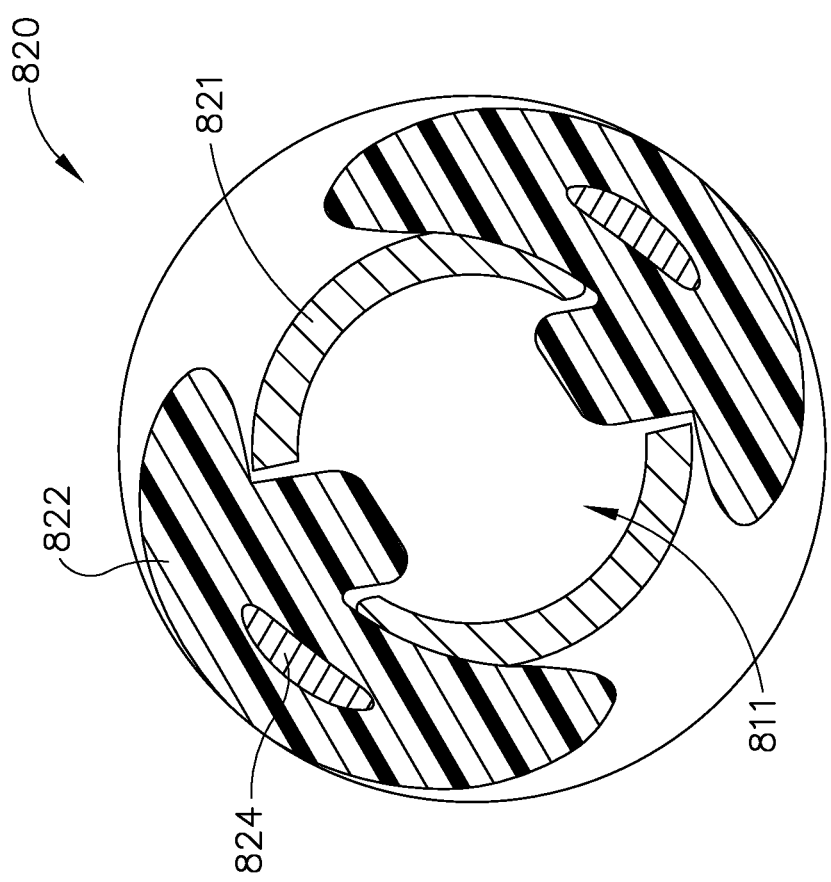
FIG. 24 depicts a cross-sectional view of the cleaning device of FIG. 23, taken along line 24-24 of FIG. 23.

5. Exemplary Cleaning Device with Double Helix Brush and Slidable Brush Retention Sheath FIGS. 23-25C show another exemplary cleaning device (800) that may be used and stored within instrument (10). As best seen in FIGS. 23 and 25C, cleaning device (800) includes a handle assembly (810), a brush assembly (820), and a removable cap (802). Removable cap (802) is substantially similar to removable cap (302) described above.

Figure 25A:
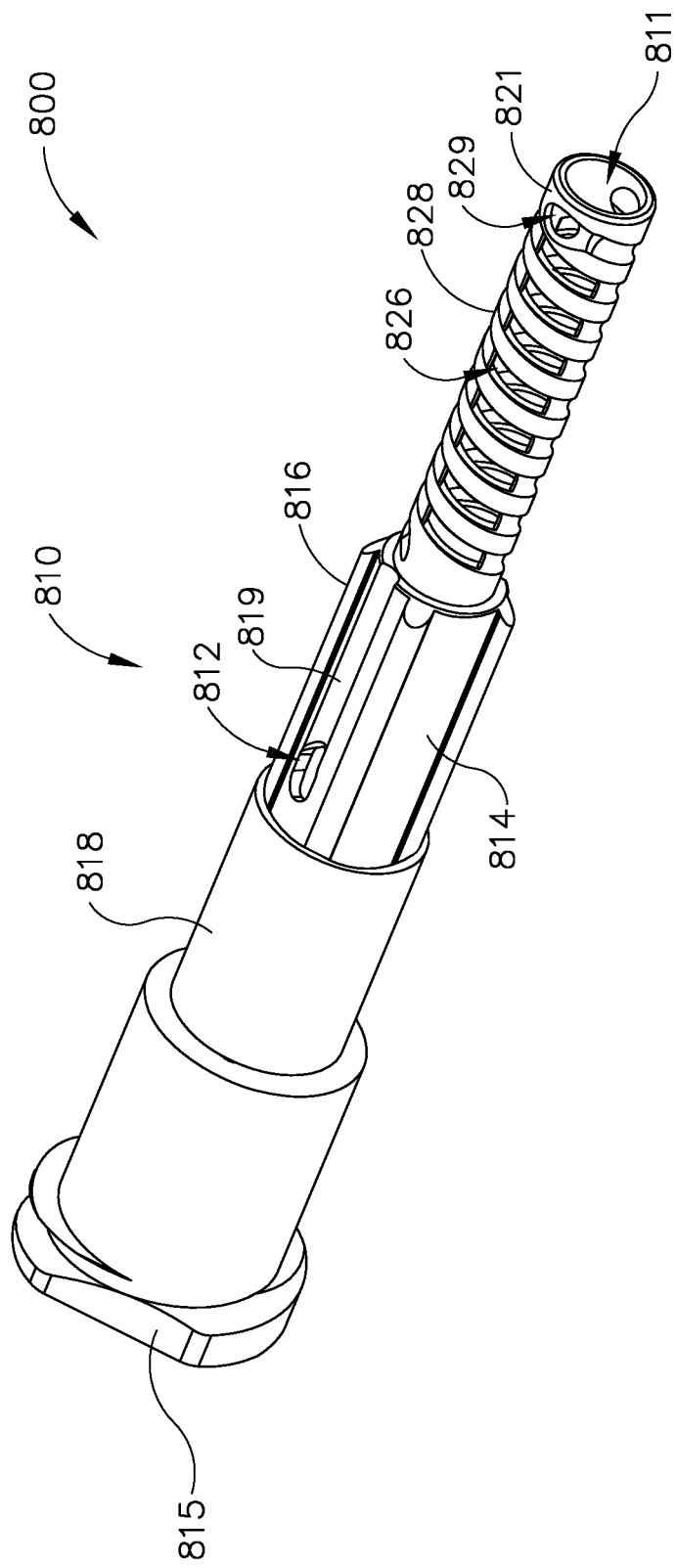
FIG. 25A depicts a perspective view of the cleaning device of FIG. 23, with the bristle section omitted and a slidable sleeve in a non-retaining position.

As best seen in FIG. 25A, handle assembly (810) includes a flexible handle (814) defining pair of anchor holes (812) and axial grooves (819). It should be understood that one anchor hole (812) and one axial groove (819) are obscured in FIG. 25A, as they are positioned diametrically opposite to the shown anchor hole (812) and axial groove (819). Anchor holes (812) are spaced 180 degrees apart on flexible handle (814). Similarly, axial grooves (819) are spaced 180 degrees apart on flexible handle (814). While anchor holes (812) and axial grooves (819) are spaced 180 degrees apart, this is not necessary. Any other suitable spacing may be used as would be apparent to one having ordinary skill in the art.

Flexible handle (814) further includes a plurality of protrusions (816), a retention sleeve (818) slidably disposed around flexible handle (814), and a luer fitting (815). Luer fitting (815) is substantially similar to Luer fitting (315) mentioned above. Protrusions (816) are substantially similar to protrusions (316) mentioned above. Flexible handle (814) is substantially similar to flexible handle (314) mentioned above with the differences noted herein.

Brush assembly (820) includes a hollow shaft (821) and a wire (824) surrounded by a brush body (822). Hollow shaft (821) defines a plurality of recesses (826), a helical groove (828), and a return hole (829). Hollow shaft (821) may possess sufficient resilient flexibility such that hollow shaft (821) may conform to the contours of ultrasonic blade (190) in versions where blade (190) has a curved longitudinal profile. Handle assembly (810) and brush assembly (820) define lumen (811). Lumen (811) may provide fluid communication from a fluid source to selected portions of end effector (180) and shaft assembly (150) as described above. Hollow shaft (821) is dimensioned to receive ultrasonic blade (190) and waveguide (192). Additionally, and similar to flexible shaft (312, 512, 712), hollow shaft (821) is dimensioned to fit within distally projecting tongues (154, 172) and inner tube (170).

Brush body (822) includes a plurality of bristles (not shown). Such bristles may have any suitable degree of stiffness. Brush body (822) is sufficiently resilient to compress within tight spaces and later return to its original shape when exiting tight spaces. Brush body (822) may have sufficient abrasive qualities to remove surgical debris caked onto the outer diameters of blade (190) and waveguide (192), as well as surgical debris caked onto the inner diameters of distally projecting tongues (152, 172) and inner tube (170). Brush body (822) may be made of any suitable material known to one having ordinary skill in the art in view of the teachings herein.

Figure 25B:
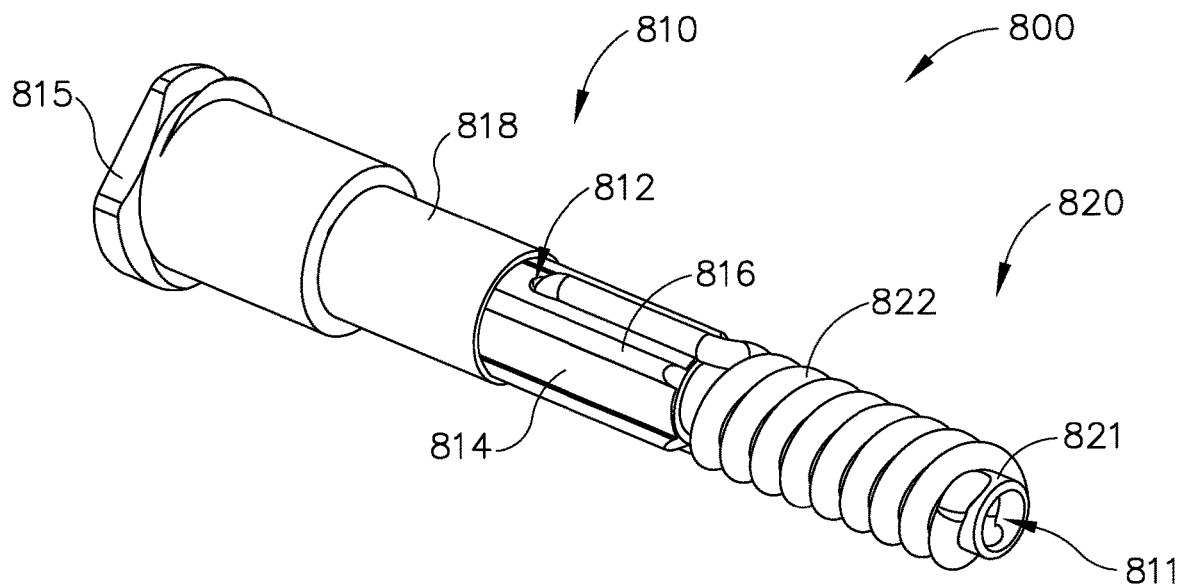
FIG. 25B depicts a perspective view of the cleaning device of FIG. 23, with the bristle section included and the slidable sleeve in the non-retaining position.
Figure 25C:
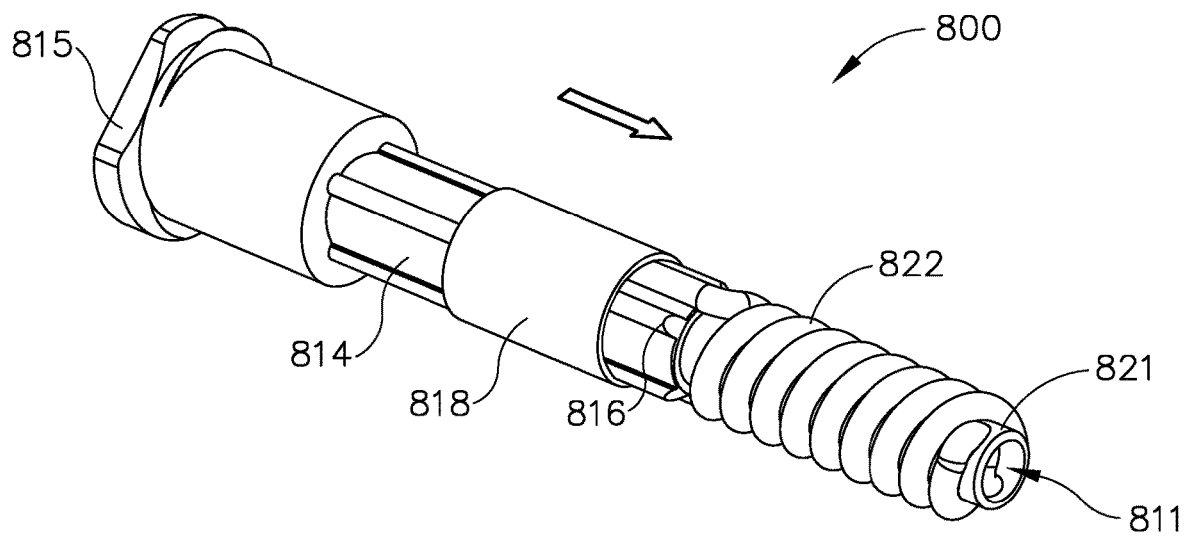
FIG. 25C depicts a perspective view of the cleaning device of FIG. 23, with the bristle section included and the slidable sleeve in a retaining position.

As best seen in FIG. 25B, brush body (822) and wire (824) extend inside anchor hole (812) and along axial groove (819) of flexible handle (814). Brush body (822) and wire (824) then wrap around every other helical groove (828) of hollow shaft (821) until brush body (822) and wire (824) extend through return holes (829). Brush body (822) and wire (824) then wrap around every other helical groove (828) back toward handle assembly (810), extend along the opposite axial groove (819), and then extend inside the opposite anchor hole (812). Brush body (822) and wire (824) thus form a dual helix configuration.

And shown in FIG. 25C, retention sleeve (818) is the moved into a retaining position to cover the portion of brush body (822) and wire (824) extending inside anchor hole (812). Retention sleeve (818) thus retains brush body (822) and wire (824) in place when retention sleeve is in the distal position shown in FIG. 25C. Other suitable ways in which brush body (822) and wire (824) may be selectively retained relative to shaft (821) will be apparent to those of ordinary skill in the art in view of the teachings herein.

Brush body (822) and wire (824) wrap around the outer diameter of hollow shaft (821) in such a way that brush body (822) and wire (824) partially rest within recesses (826). Brush body (822) is wrapped around recesses (826) with sufficient force to compress portions of brush body (822) within recesses (826). Thus, as best seen in FIG. 24, a portion of brush body (822) is exposed to the inner diameter of hollow shaft (821) as well as the outer diameter of hollow shaft (821). As mentioned above, hollow shaft (821) is dimensioned to fit around the outer diameters of blade (190) and waveguide (192); and to fit within the inner diameters of distally projecting tongues (154, 172) and inner tube (170). An operator may thus insert hollow shaft (821) over blade (190) and waveguide (192) and within distally projecting tongues (153, 172) and inner tube (170), and the abrasive qualities of brush body (822) may help remove surgical debris caked onto blade (190), waveguide (192), distally projecting tongues (152, 172) and inner tube (170).

6. Exemplary Cleaning Device with Single Helix Brush

FIGS. 26-28 show another exemplary cleaning device (900) that may be used and stored within instrument (10). As best seen in FIGS. 26-27, cleaning device (900) includes a luer fitting (915), a flexible handle (914), a hollow shaft (921), and a brush body (922). Luer fitting (915) may be substantially similar to luer fitting (315) described above. Cleaning device (900) defines a lumen (911). Therefore, lumen (911) may provide fluid communication from a fluid source to selected portions of end effector (180) and shaft assembly (150) as described above.

Hollow shaft (921) defines a helical groove (928) and a plurality of recesses (926). Hollow shaft (921) and flexible handle (914) may possess sufficient resilient flexibility such that hollow shaft (921) may conform to the contours of ultrasonic blade (190) in versions where blade (190) has a curved longitudinal profile. Hollow shaft (921) is dimensioned to receive ultrasonic blade (190) and waveguide (192). Additionally, and similar to flexible shaft (312, 512, 712), hollow shaft (921) is dimensioned to fit within distally projecting tongues (154, 172) and inner tube (170).

Brush body (922) includes a plurality of bristles (not shown). Such bristles may have any suitable degree of stiffness. Brush body (922) is sufficiently resilient to compress within tight spaces and later return to its original shape when exiting tight spaces. Brush body (922) may have sufficient abrasive qualities to remove surgical debris caked onto the outer diameters of blade (190) and waveguide (192), as well as surgical debris caked onto the inner diameters of distally projecting tongues (152, 172) and inner tube (170). Brush body (922) may be made of any suitable material known to one having ordinary skill in the art in view of the teachings herein.

Brush body (922) may be wrapped around a wire (not shown), similar to brush body (322, 522, 622, 722, 822). Similar to cleaning device (800), brush body (922) wraps around helical groove (928). While cleaning device (800) had a double helix configuration, helical groove (928) has a single helix configuration in this example, such that brush body (922) does not wrap back around hollow shaft (921). It should be understood that cleaning device (900) may include a retention sleeve similar to retention sleeve (818); or some other component that is configured to removably retain brush body (922) relative to shaft (921).

Brush body (922) wraps around the outer diameter of hollow shaft (921) in such a way that brush body (922) partially rests within recesses (926). Brush body (922) is wrapped around recesses (926) with sufficient force to compress portions of brush body (922) within recesses (926). Thus, as best seen in FIG. 28, a portion of brush body (922) is exposed to the inner diameter of hollow shaft (921) as well as the outer diameter of hollow shaft (921). As mentioned above, hollow shaft (921) is dimensioned to fit around the outer diameters of blade (190) and waveguide (192); and to fit within the inner diameters of distally projecting tongues (154, 172) and inner tube (170). An operator may thus insert hollow shaft (921) over blade (190) and waveguide (192) and within distally projecting tongues (153, 172) and inner tube (170), and the abrasive qualities of brush body (922) may help remove surgical debris caked onto blade (190), waveguide (192), distally projecting tongues (152, 172) and inner tube (170).

7. Exemplary Cleaning Device with Multi-Helical Brushes

Figure 29:
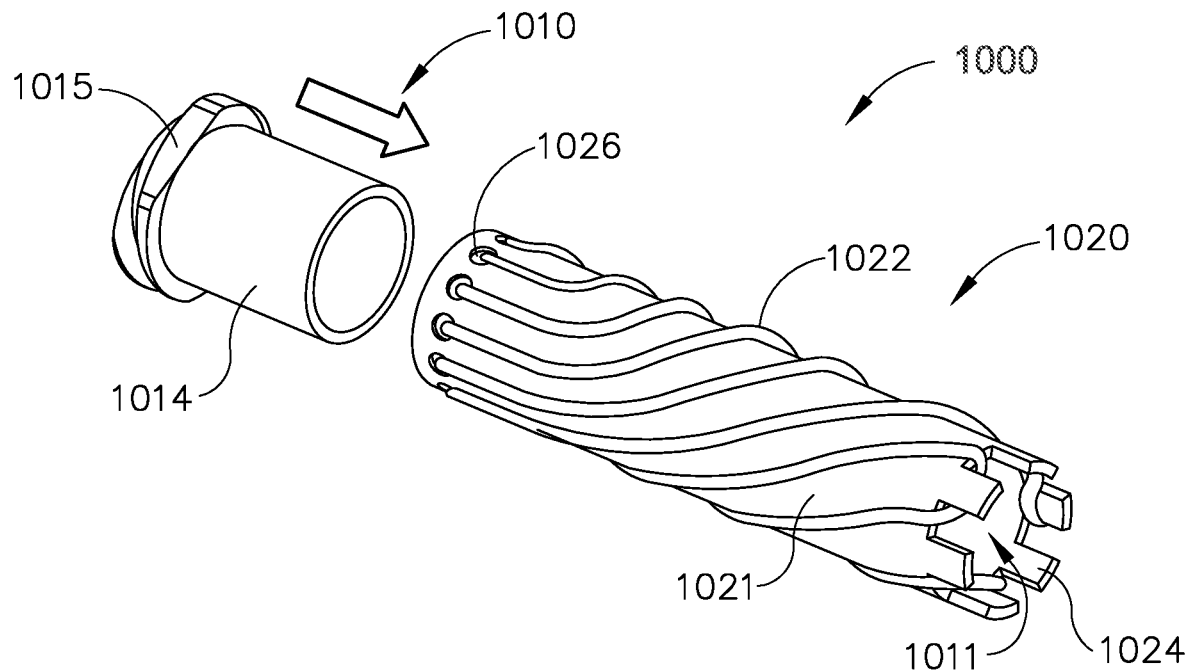
FIG. 29 depicts a perspective view of another alternative cleaning device that may be used to clean the end effector and the shaft assembly of FIG. 2, with a sleeve is in the unlocked position.

FIG. 29 shows another exemplary cleaning device (1000) that may be used and stored within instrument (10). Cleaning device (1000) includes a handle assembly (1010) and a brush assembly (1020). Handle assembly (1010) is removable from brush assembly (1020). However, handle assembly (1010) may have an interference fit with brush assembly (1020) such that when handle assembly (1010) slides onto brush assembly (1010), a sufficient frictional force is provided to prevent handle assembly (1010) from sliding off of brush assembly (1020).

Handle assembly (1010) includes a luer fitting (1015) and a flexible handle (1014). Luer fitting (1015) and flexible handle (1014) may be substantially similar to luer fitting (315) and flexible handle (314) described above.

Brush assembly (1020) includes a plurality of brush bodies (1022) and a hollow shaft (1021) with a plurality of apertures (1026) on one end and a plurality of protrusions (1024) on the other end. Hollow shaft (1021) may possess sufficient resilient flexibility such that hollow shaft (1021) may conform to the contours of ultrasonic blade (190) in versions where blade (190) has a curved longitudinal profile. Handle assembly (1010) and brush assembly (1020) define lumen (1011). Lumen (1011) may provide fluid communication from a fluid source to selected portions of end effector (180) and shaft assembly (150) as described above. Hollow shaft (1021) is dimensioned to receive ultrasonic blade (190) and waveguide (192). Additionally, and similar to flexible shaft (312, 512, 712), hollow shaft (1021) is dimensioned to fit within distally projecting tongues (154, 172) and inner tube (170).

Brush body (1022) includes a plurality of bristles (not shown). Such bristles may have any suitable degree of stiffness. Brush body (1022) is sufficiently resilient to compress within tight spaces and later return to its original shape when exiting tight spaces. Brush body (822) may have sufficient abrasive qualities to remove surgical debris caked onto the outer diameters of blade (190) and waveguide (192), as well as surgical debris caked onto the inner diameters of distally projecting tongues (152, 172) and inner tube (170). Brush body (822) may be made of any suitable material known to one having ordinary skill in the art in view of the teachings herein.

Each brush body (1022) extends through one aperture (1026), along hollow shaft (1021) along a respective helical path, and wraps around a protrusion (1024) in order to travel back along hollow shaft (1021). Thus, the portion of brush body (1022) wrapped around protrusion (1024) is located adjacent to the inner diameter of hollow shaft (1021); while the portion of brush body (1022) extending helically along hollow shaft (1021) is located adjacent to the outer diameter of hollow shaft (1021). An operator may therefore insert hollow shaft (1021) over blade (190) and waveguide (192) and within distally projecting tongues (153, 172) and inner tube (170). The abrasive qualities of brush body (1022) may help remove surgical debris caked onto blade (190), waveguide (192), distally projecting tongues (152, 172) and inner tube (170).

8. Exemplary Cleaning Device with Abrasive Material and Circular Shaft

Figure 30:
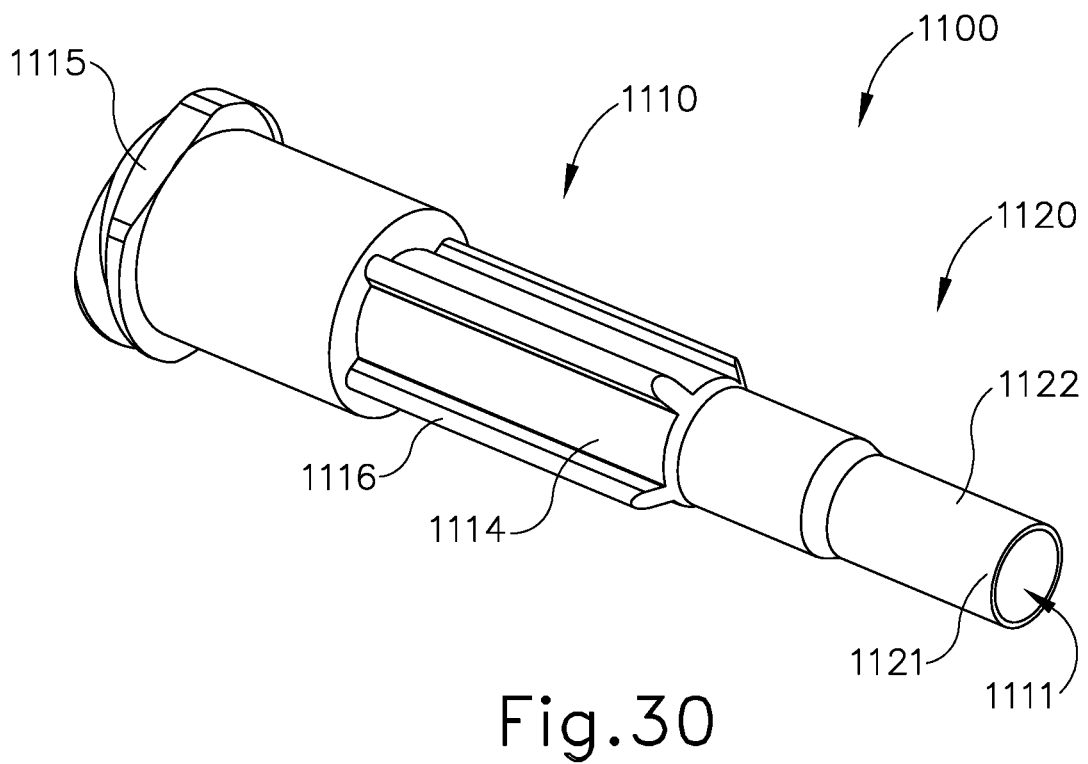
FIG. 30 depicts a perspective view of another alternative cleaning device that may be used to clean the end effector and the shaft assembly of FIG. 2.

FIG. 30 shows another exemplary cleaning device (1100) that may be used and stored within instrument (10). Cleaning device (1100) includes a handle assembly (1110) and a brush assembly (1120). Handle assembly includes a luer fitting (1115), a flexible handle (1114), and a plurality of protrusions (1116); which may be substantially similar to luer fitting (315), flexible handle (314), and plurality of protrusions (316) mentioned above.

Brush assembly (1120) includes a hollow shaft (1121) covered with abrasive material (1122) on the inner diameter and the outer diameter of hollow shaft (1121). Handle assembly (1110) and brush assembly (1120) define lumen (1111). Lumen (1111) may provide fluid communication from a fluid source to selected portions of end effector (180) and shaft assembly (150) as described above. Hollow shaft (1121) is dimensioned to receive ultrasonic blade (190) and waveguide (192). Additionally, and similar to flexible shaft (312, 512, 712), hollow shaft (1121) is dimensioned to fit within distally projecting tongues (154, 172) and inner tube (170).

By way of example only, abrasive material (1122) may comprise grit, knurling, ridges, and/or any other suitable kinds of abrasive surface features. Abrasive material (1122) may have sufficient abrasive qualities to remove surgical debris caked onto the outer diameters of blade (190) and waveguide (192), as well as surgical debris caked onto the inner diameters of distally projecting tongues (152, 172) and inner tube (170). Abrasive material (1122) may be made of any suitable material known to one having ordinary skill in the art in view of the teachings herein.

It should be understood that an operator may insert hollow shaft (1121) over blade (190) and waveguide (192) and within distally projecting tongues (153, 172) and inner tube (170), and the abrasive qualities of abrasive material (1122) may help remove surgical debris caked onto blade (190), waveguide (192), distally projecting tongues (152, 172) and inner tube (170).

9. Exemplary Cleaning Device with Abrasive Material and Semi-Circular Shaft

Figure 31:
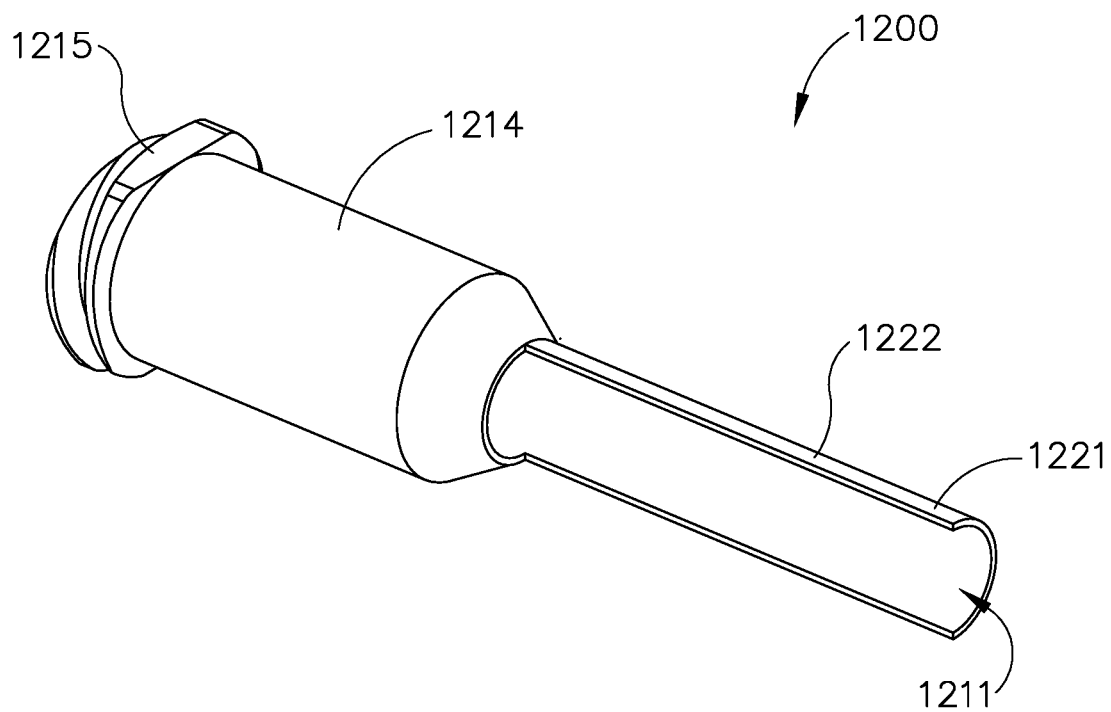
FIG. 31 depicts a perspective view of another alternative cleaning device that may be used to clean the end effector and the shaft assembly of FIG. 2.

FIG. 31 shows another exemplary cleaning device (1200) that may be used and stored within instrument (10). Cleaning device (1200) includes a handle assembly (1210) and a brush assembly (1220). Handle assembly includes a luer fitting (1215), and a flexible handle (1214), which may be substantially similar to luer fitting (315), and flexible handle (314), mentioned above.

Brush assembly (1220) includes a semicircular hollow shaft (1221) covered with abrasive material (1222) on the inner diameter and the outer diameter of semicircular hollow shaft (1221). Handle assembly (1210) and brush assembly (1220) define a partial lumen (1211). Partial lumen (1211) may provide fluid communication from a fluid source to selected portions of end effector (180) and shaft assembly (150) as described above. Semicircular hollow shaft (1121) is dimensioned to receive ultrasonic blade (190) and waveguide (192). Additionally, and similar to flexible shaft (312, 512, 712), semicircular hollow shaft (1221) is dimensioned to fit within distally projecting tongues (154, 172) and inner tube (170).

By way of example only, abrasive material (1222) may comprise grit, knurling, ridges, and/or any other suitable kinds of abrasive surface features. Abrasive material (1222) may have sufficient abrasive qualities to remove surgical debris caked onto the outer diameters of blade (190) and waveguide (192), as well as surgical debris caked onto the inner diameters of distally projecting tongues (152, 172) and inner tube (170). Abrasive material (1222) may be made of any suitable material known to one having ordinary skill in the art in view of the teachings herein.

It should be understood that an operator may insert hollow shaft (1221) over blade (190) and waveguide (192) and within distally projecting tongues (153, 172) and inner tube (170), and the abrasive qualities of abrasive material (1122) may help remove surgical debris caked onto blade (190), waveguide (192), distally projecting tongues (152, 172) and inner tube (170).

10. Exemplary Cleaning Device with Flexible Scraping Edge

Figure 32:
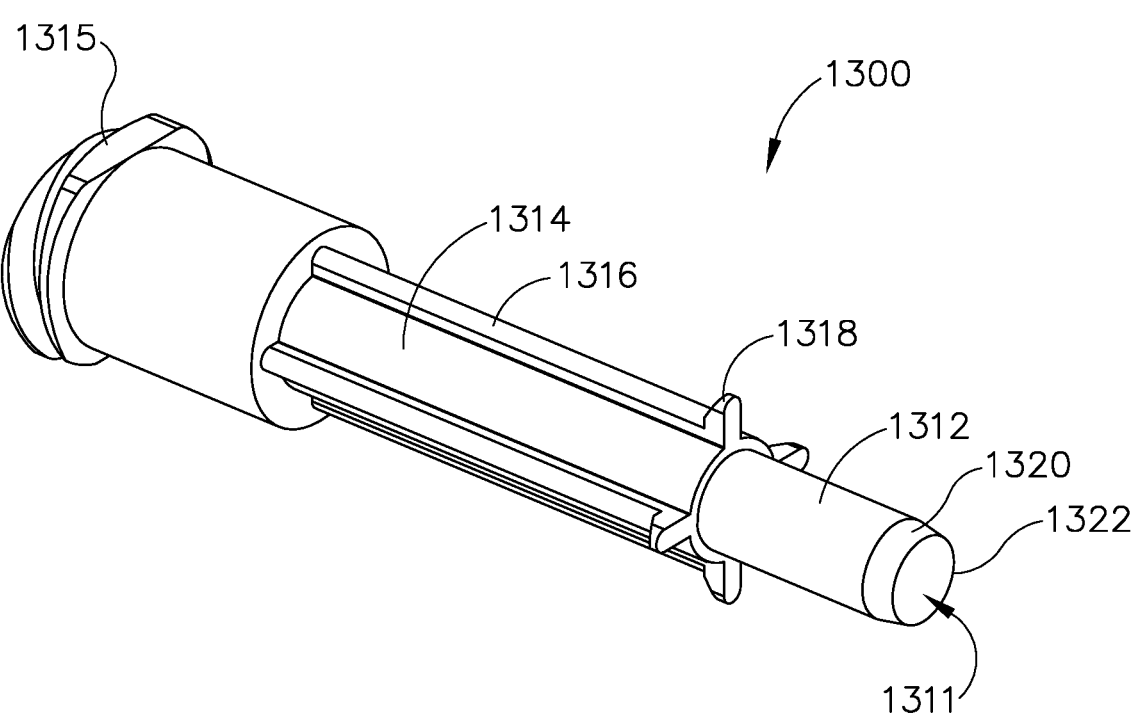
FIG. 32 depicts a perspective view of an another alternative cleaning device that may be used to clean the end effector and the shaft assembly of FIG. 2.
Figure 33:
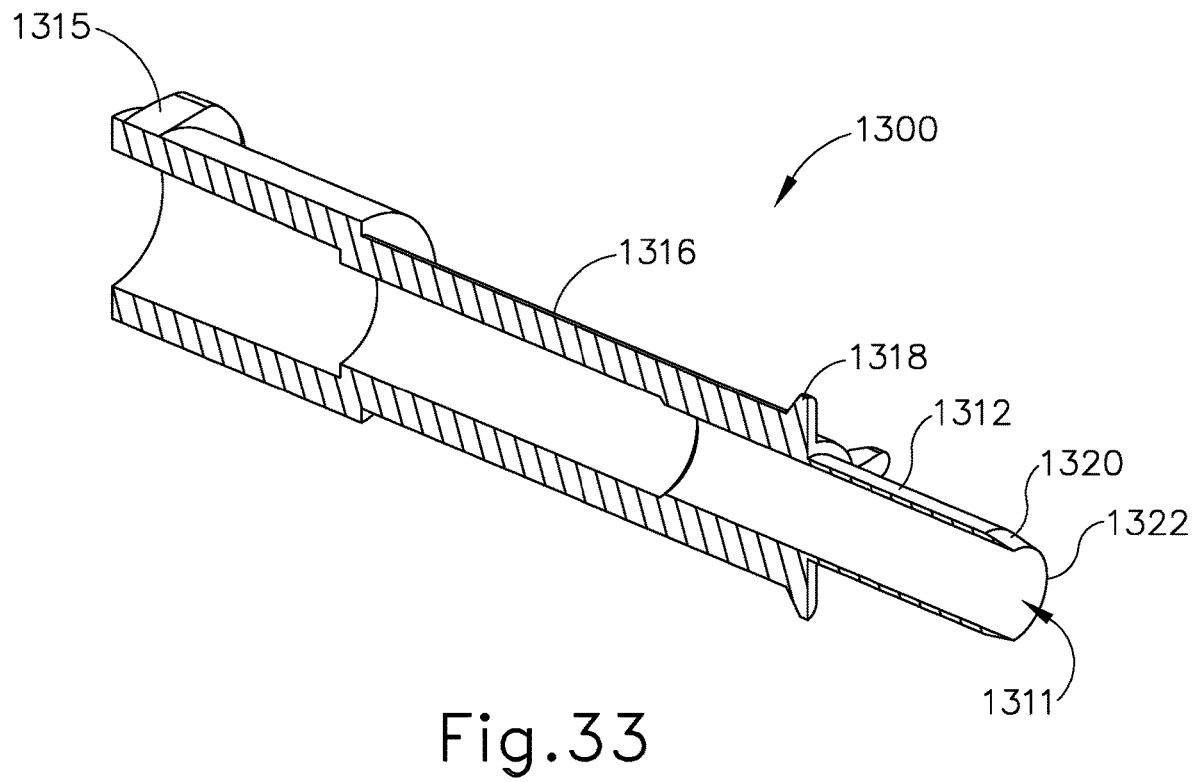
FIG. 33 depicts a perspective cross-sectional view of the cleaning device of FIG. 32.
Figure 34:
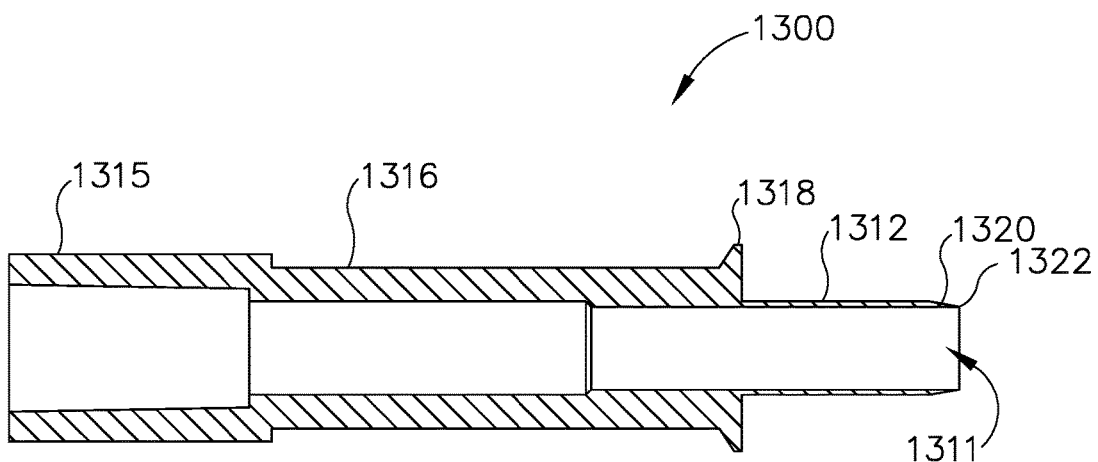
FIG. 34 depicts a side cross-sectional view of the cleaning device of FIG. 32.

FIGS. 32-34 show another exemplary cleaning device (1300) that may be used and stored within instrument (10). As best seen in FIG. 32, cleaning device (1300) includes a flexible shaft (1312), a flexible handle (1314), a plurality of projections (1316), a plurality of stops (1318), and a luer fitting (1315); all substantially similar to flexible shaft (312), flexible handle (314), plurality of projections (316), plurality of stops (318), and luer fitting (315) described above respectively, with differences described below. Handle assembly (510) thus defines a lumen (1311) that may provide fluid communication from a fluid source to selected portions of end effector (180) and shaft assembly (150) as described above.

Flexible shaft (1312) is dimensioned to receive ultrasonic blade (190) and waveguide (192). Additionally, flexible shaft (1312) is dimensioned to fit within distally projecting tongues (152, 172) and inner tube (170). An operator may thus insert flexible shaft (1312) within distally projecting tongues (152, 172) and inner tube (171) up to distal seal (193). Flexible shaft (1312) also includes a tapered edge (1320) terminating into an edge (1322). Edge (1322) is dimensioned to hug the outer diameter of ultrasonic blade (190) and waveguide (192) as flexible shaft (1312) is inserted up to distal seal (193). Tapered edge (1320) may expand around blade (190) or waveguide (192) to accommodate the change in diameter along the longitudinal profile of blade (190) or waveguide (192). Edge (1322) may thus scrape off excess debris caked onto blade (190) and waveguide (192) as flexible shaft (1312) is inserted toward distal seal (193).

B. Exemplary Integral Cleaning Devices

In some instances, it may be desirable to provide an end effector and/or shaft assembly cleaning device that is fully integrated into instrument (10). This may reduce the number of components that an operator must manipulate and track. Several merely illustrative examples of end effector and/or shaft assembly cleaning devices that are fully integrated into instrument (10) are described in greater detail below.

1. Exemplary Shaft Assembly with Integral Translating Scraper

Figure 35A:
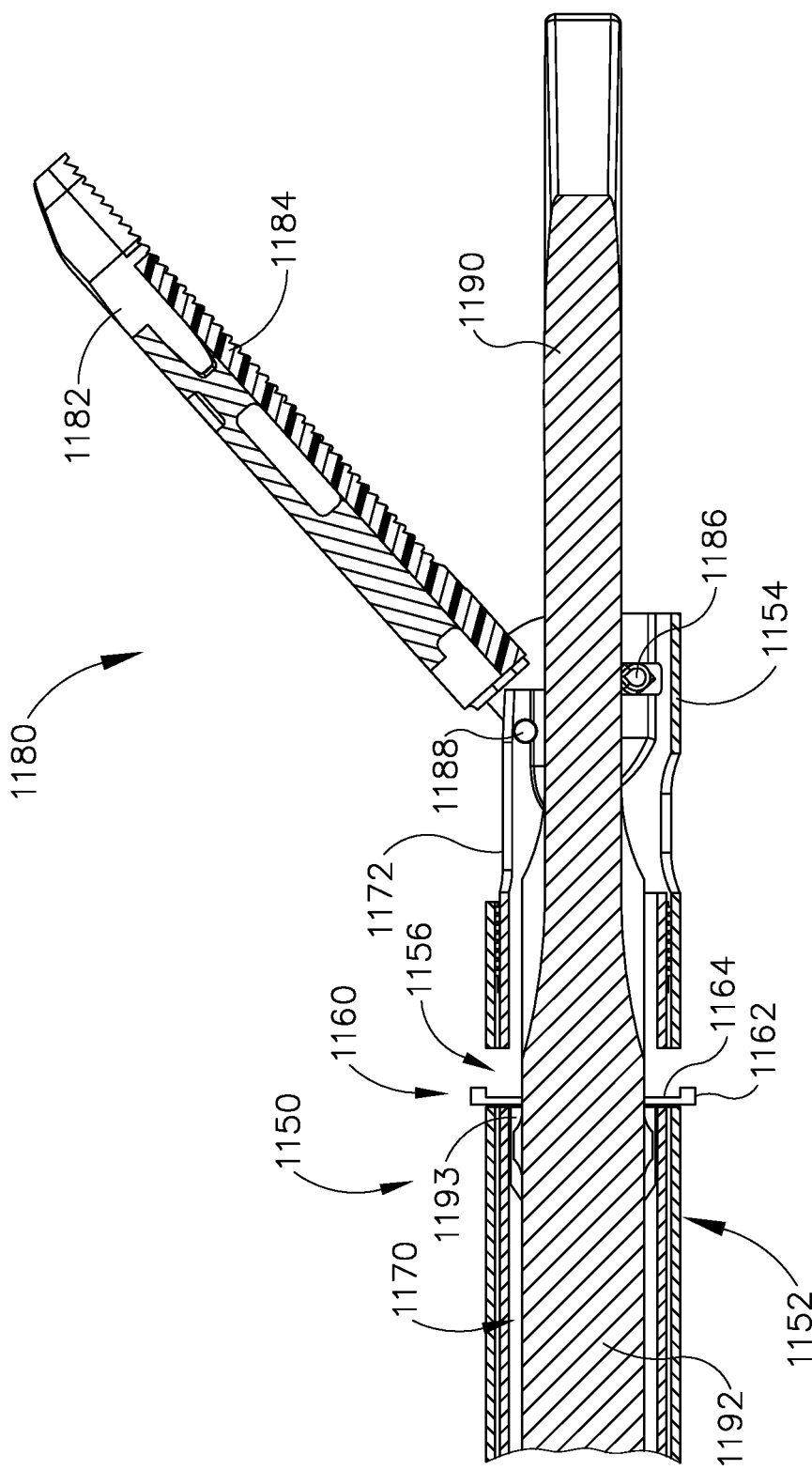
FIG. 35A depicts a side cross-sectional view of an alternative shaft assembly and alternative end effector that may be incorporated into the instrument of FIG. 1, where the shaft assembly includes a slidably attached cleaning device, where the slidably attached cleaning device is in a first position.
Figure 35B:
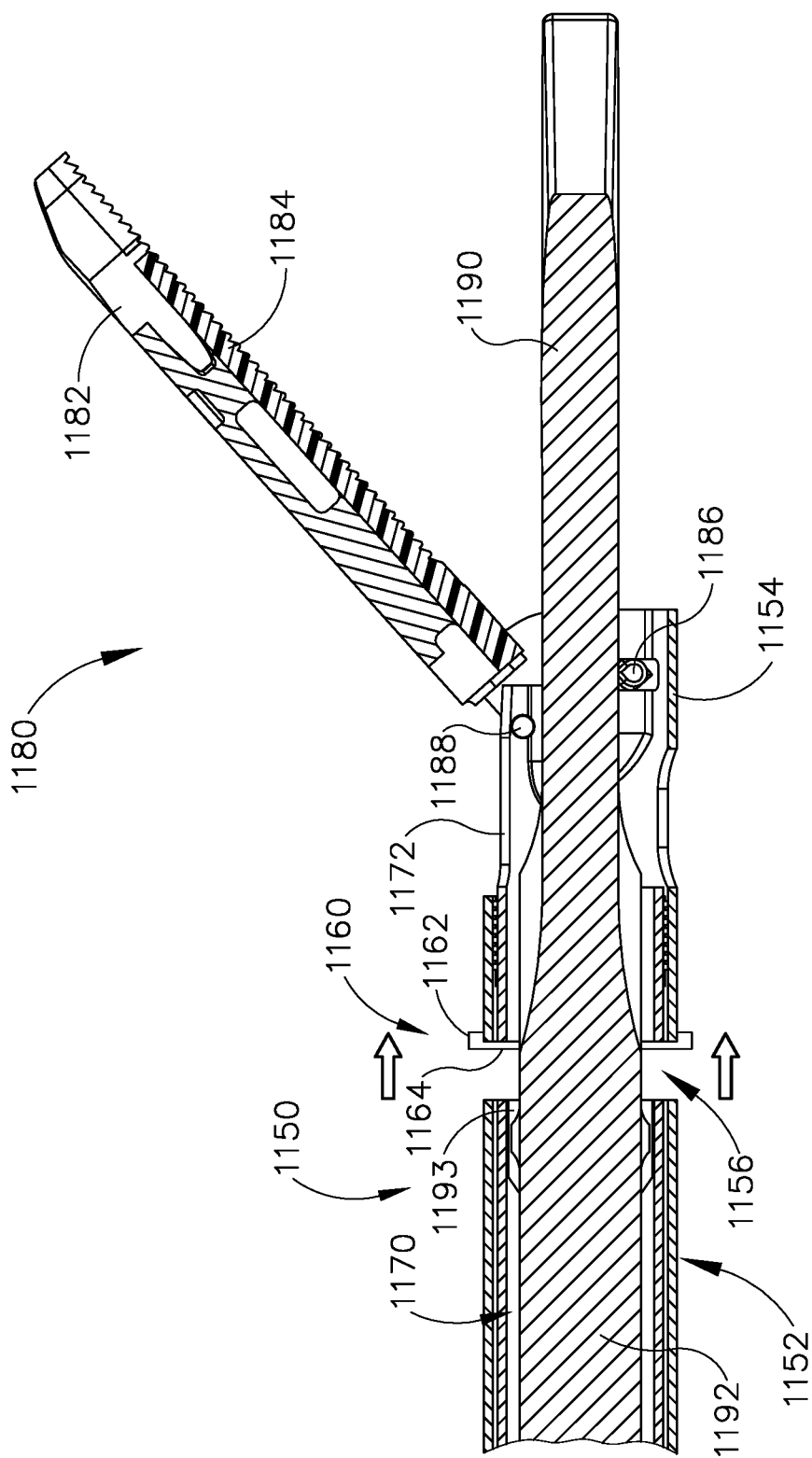
FIG. 35B depicts a side cross-sectional view of the shaft assembly and end effector of FIG. 35A, where the slidably attached cleaning device is in a second position.
Figure 36:
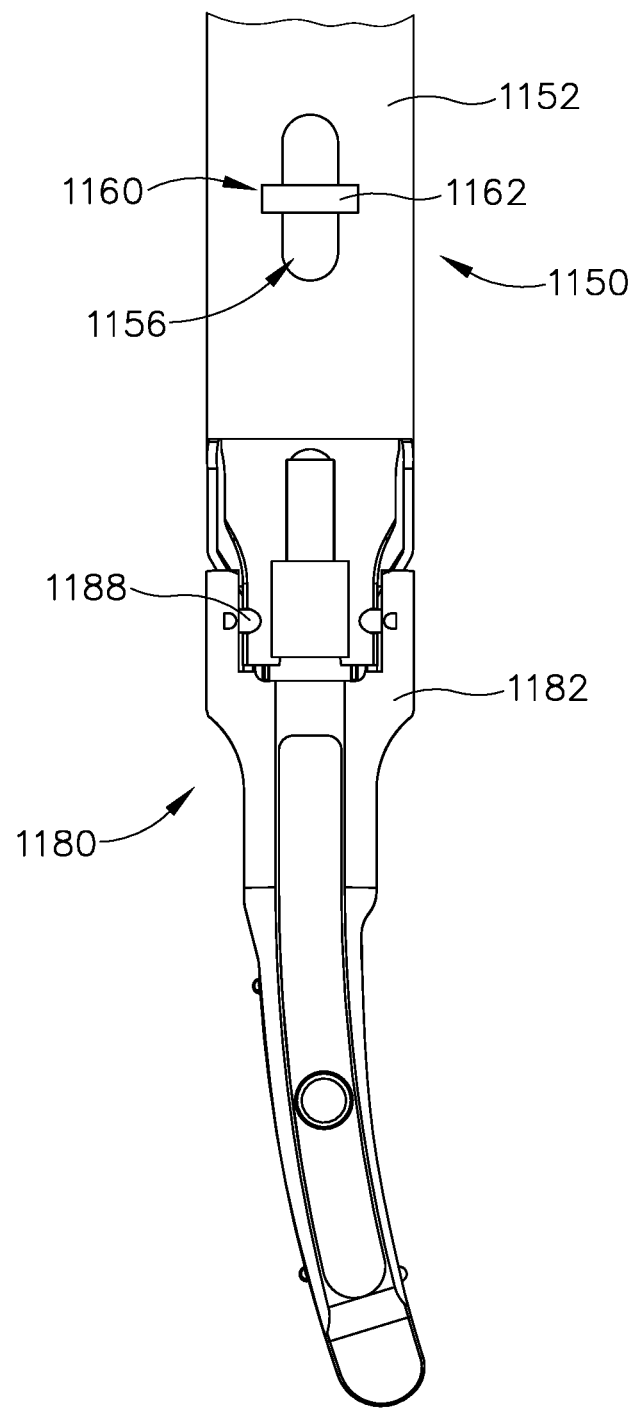
FIG. 36 depicts a top plan view of the shaft assembly and end effector of FIG. 35A.

FIGS. 35A-36 show an alternative shaft assembly (1150) and end effector (1180) that may be incorporated into instrument (10) in place of shaft assembly (150) and end effector (180). Shaft assembly (1150) and end effector (1180) may be configured and operable just like shaft assembly (150) and end effector (180) except for the differences described below. End effector (1180) includes a clamp arm (1182), clamp pad (1184), and blade (1190), that are substantially similar to clamp arm (182), clamp pad (184) and blade (190) mentioned above. Shaft assembly (1150) includes a distal seal (1193), an acoustic waveguide (1192), an outer tube (1152), and an inner tube (1170) that are substantially similar to distal seal (193), acoustic waveguide (192), outer tube (152) and inner tube (170) mentioned above, with differences described below. Inner tube (1170) includes a distally projecting tongue (1172) that is substantially similar to distally projecting tongue (172) mentioned above. Outer tube (1152) includes a distally projecting tongue (1154) that is substantially similar to distally projecting tongue (154) mentioned above. Clamp arm (1182) is pivotally connected to pin (1188) and integral pin feature (1186) such that translation of outer tube (1152) pivots clamp arm (1182) toward and away from ultrasonic blade (1190).

Outer tube (1152) and inner tube (1170) together define a pair of slots (1156) in which a cleaning feature (1160) is housed. Slots (1156) are sized and arranged to accommodate relative movement between tubes (1152, 170) during actuation of clamp arm (1182), without interference from cleaning feature (1160). Cleaning feature (1160) includes a pair of grips (1162) housed adjacent to outer tube (1152). Cleaning feature (1160) further includes a scraper (1164) extending from grips (1162) toward acoustic waveguide (1192). Scraper (1164) may be configured to encompass acoustic waveguide (1192).

As best seen in FIGS. 35A-35B, cleaning feature (1162) is capable of traveling longitudinally from a first position to a second position. While cleaning feature (1160) is in the first position, as shown in FIG. 35A, scraper (1164) is adjacent to distal seal (1193). An operator may then actuate cleaning feature (1160) in the distal direction to the second position, as shown in FIG. 35B, by sliding grips (1162) in the distal direction. Because scraper (1164) encompasses acoustic waveguide (1192), scraper (1164) may dislodge any excess surgical debris that caked onto the portion of acoustic waveguide (1192) in contact with scraper (1164).

2. Exemplary Shaft Assembly with Integral Translating and Rotating Scraper

Figure 37:
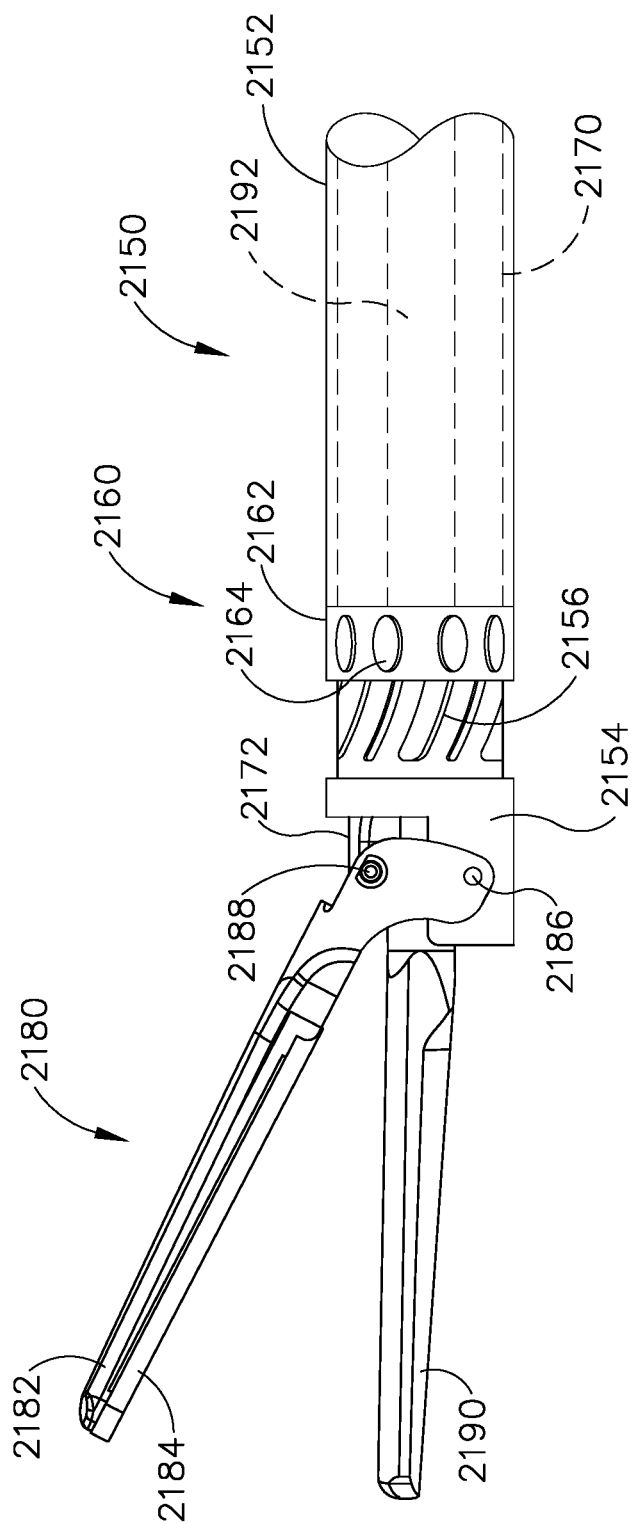
FIG. 37 depicts a side elevational view of another alternative shaft assembly and alternative end effector that may be incorporated in the instrument of FIG. 1, where the shaft assembly includes a cleaning device that is slidable and rotatable.
Figure 38:
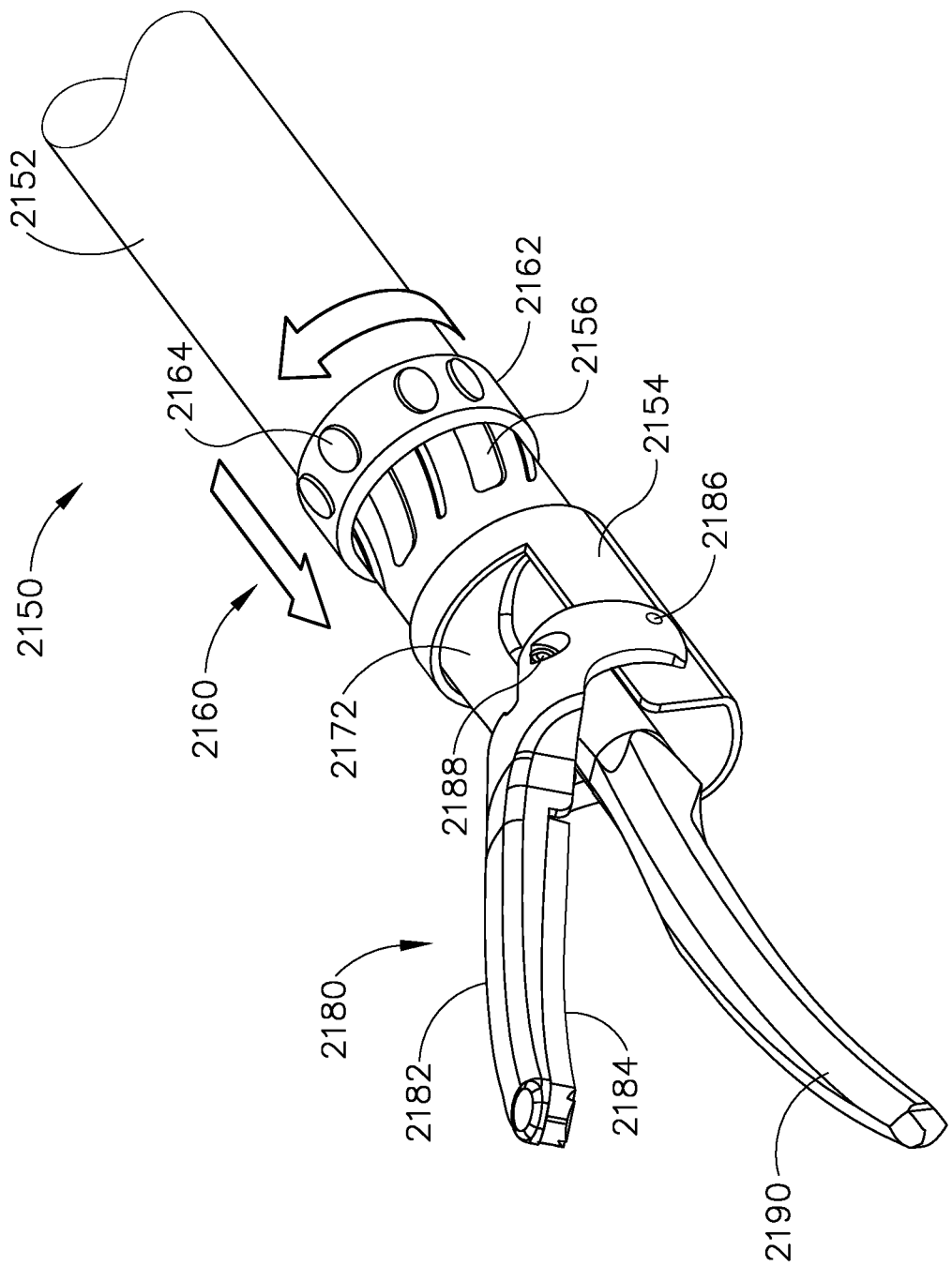
FIG. 38 depicts a perspective view of the shaft assembly and end effector of FIG. 37.

FIGS. 37-38 show another alternative shaft assembly (2150) and end effector (2180) that may be incorporated into instrument (10) in place of shaft assembly (150) and end effector (180). Shaft assembly (2150) and end effector (2180) may be configured and operable just like shaft assembly (150) and end effector (180) except for the differences described below. End effector (2180) includes a clamp arm (2182), clamp pad (2184) and blade (2190) that are substantially similar to clamp arm (182), clamp pad (184) and blade (190) mentioned above. Shaft assembly (2150) includes a distal seal (2193), an acoustic waveguide (2192), an outer tube (2152), and an inner tube (2170) that are substantially similar to distal seal (193), acoustic waveguide (192), outer tube (152) and inner tube (170) mentioned above, with differences described below. Inner tube (2170) includes a distally projecting tongue (2172) that is substantially similar to distally projecting tongue (172) mentioned above. Outer tube (2152) includes a distally projecting tongue (2154) that is substantially similar to distally projecting tongue (154) mentioned above. Clamp arm (2182) is pivotally connected to pin (2188) and integral pin feature (2186) such that translation of outer tube (2152) pivots clamp arm (2182) toward and away from ultrasonic blade (2190).

Outer tube (1152) and inner tube (1170) together define a plurality of arched slots (2156) in which a cleaning feature (2160) is housed. Cleaning feature (2160) includes an annular grip (2162) located outside outer tube (2152) and a plurality of scrapers (2164) extending within arched slots (2156) towards acoustic waveguide (2192). Scrapers (2164) are dimensioned to make contact with acoustic waveguide (2192). As best seen in FIG. 38, cleaning feature (2160) may travel along the path provided by arched slots (2156) if an operator rotates annular grip (2162). In particular, cleaning feature (2160) will travel angularly about the longitudinal axis while simultaneously translating along the longitudinal axis while the operator rotates annular grip (2162). While cleaning feature (2160) travels along the path defined by arched slots (2156), scrapers (2164) travel helically along waveguide (2192) and dislodge any excess surgical debris that caked onto the portion of acoustic waveguide (2192) in contact with scraper (2164).

3. Exemplary Scraping Ring

FIGS. 39-42B show a cleaning device (160) that may be readily incorporated into shaft assembly (150) and end effector (180) described above. Cleaning feature (160) includes a body (162) fixed to a pair of legs (168). Body (162) defines a channel (166) that is dimensioned to house a portion of acoustic waveguide (192). Body (162) also includes an angular array of scrapers (164) pointing toward acoustic waveguide (192). The points of scrapers (164) are intended to make contact with the outer diameter of acoustic waveguide (192). As will be described in greater detail below, cleaning device (160) is configured to translate along a portion of acoustic waveguide (192) in response to translation of outer tube (2152), where scrapers (164) may dislodge surgical debris caked onto acoustic waveguide (192).

Figure 42A:
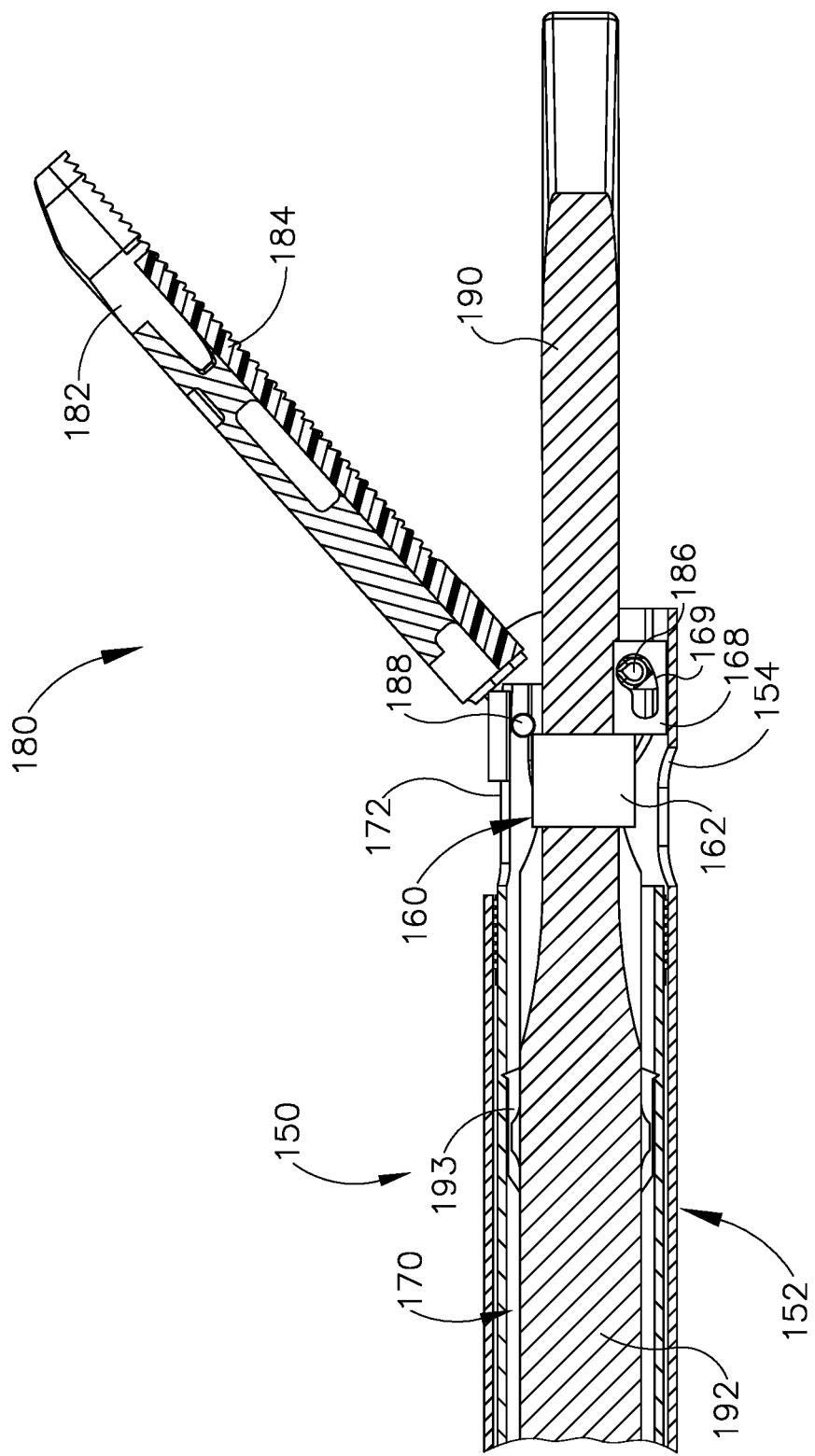
FIG. 42A depicts a cross-sectional side view of the slidable cleaning device of FIG. 39 attached to the end effector and the shaft assembly of FIG. 2, where the end effector and the shaft assembly are in the open configuration.
Figure 42B:
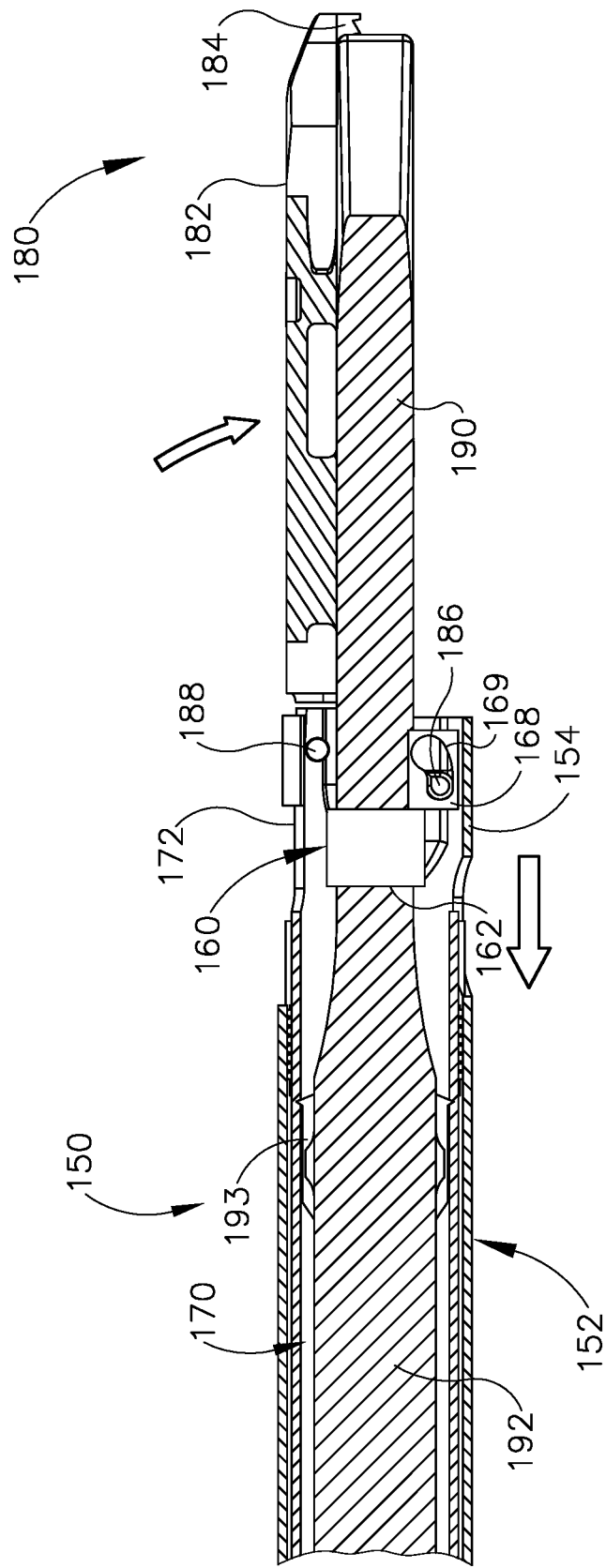
FIG. 42B depicts a cross-sectional side view of the slidable cleaning device of FIG. 39 attached to the end effector and the shaft assembly of FIG. 2, where the end effector and the shaft assembly are in the closed configuration.

Each leg (168) includes a kidney slot (169). As can be seen in FIGS. 42A-42B, each kidney slot (169) is dimensioned to house integral pin feature (186). Kidney slot (169) is dimensioned to make contact with integral pin feature (186) as distally projecting tongue (154) translates. In other words, cleaning device (160) will translate longitudinally along waveguide (192) in response to the action of pivoting clamp arm (182) toward and away from blade (190). Integral pin feature (186) cams against kidney slot (169) to translate cleaning device (160) in the proximal or distal direction relative to acoustic waveguide (192). However, the shape of kidney slot (169) is dimensioned such that legs (168) do not make contact with integral pin feature (186) as integral pin feature (186) travels in the vertical direction relative to distally projecting tongue (154). Therefore, movement of cleaning device (160) is limited in the proximal and distal directions.

When cleaning device (160) translates relative to waveguide (192), scrapers (164) make contact with the outer diameter of acoustic waveguide (192), thereby dislodging surgical debris caked onto waveguide (192). In some versions, scrapers (164) are rigid. In some other examples, scrapers are flexible (e.g., elastomeric). Various suitable materials that may be used to form scrapers (164) will be apparent to those of ordinary skill in the art in view of the teachings herein. Similarly, various suitable properties that scrapers (164) may have will be apparent to those of ordinary skill in the art in view of the teachings herein.

4. Exemplary Scrapers on Outer Tube

Figure 44:
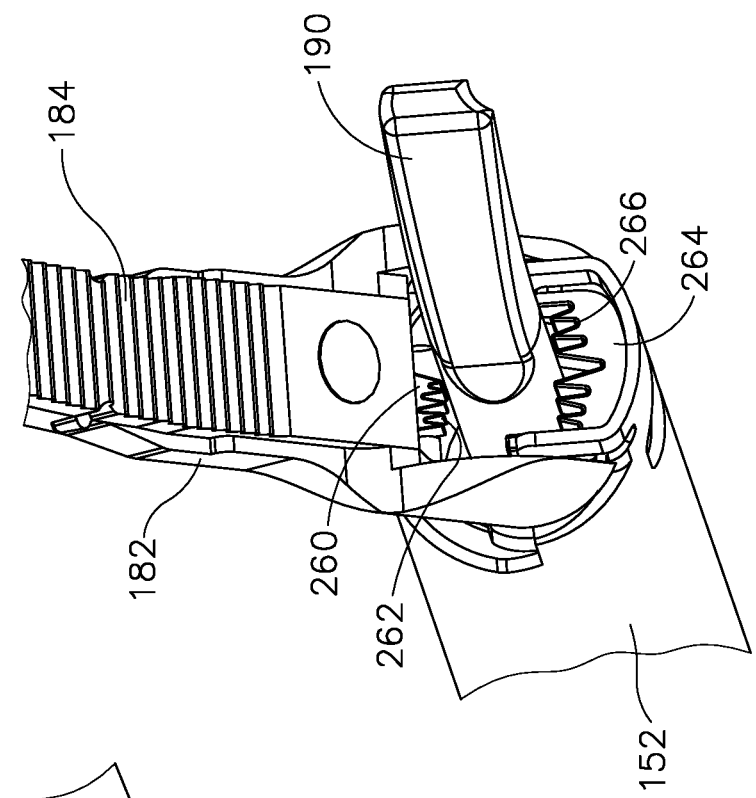
FIG. 44 depicts a perspective view of the cleaning device of FIG. 43 attached to the shaft assembly of FIG. 2, where the end effector and shaft assembly of FIG. 2 are in the open configuration.
Figure 43:
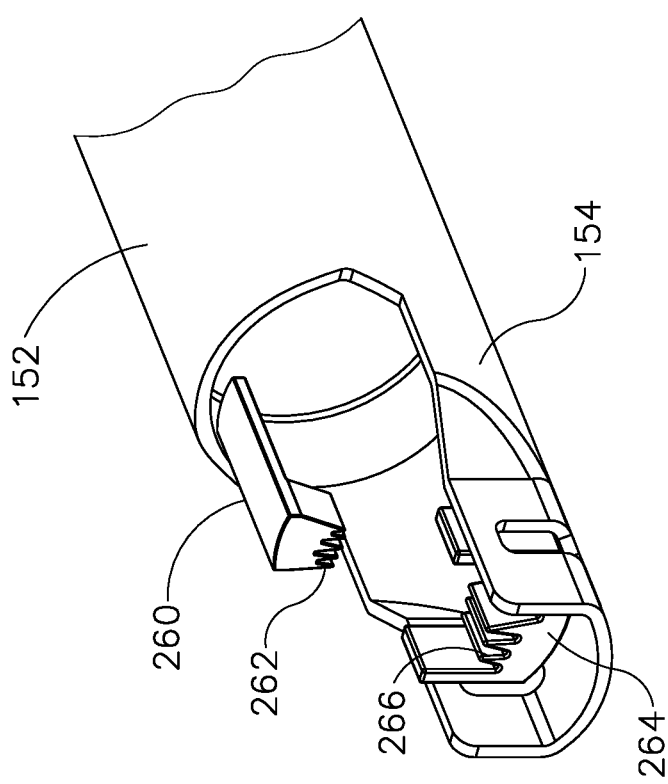
FIG. 43 depicts a perspective view of another cleaning device attached to an outer tube of the shaft assembly of FIG. 2.

FIGS. 43-44 show a pair of alternative cleaning devices (260, 264) that may also be readily incorporated into shaft assembly (150) and end effector (180) described above. As best shown in FIG. 43, top cleaning device (260) and bottom cleaning device (264) may be fixed to distally projecting tongue (154). Top cleaning device (260) and bottom cleaning device (264) each include a plurality of scrapers (262, 266) respectively. As can be seen in FIG. 44, scrapers (262, 266) are positioned to make contact with acoustic waveguide (192) or blade (190). Therefore, as outer tube (152) translates in order to pivot clamp arm (182) relative to blade (190), scrapers (262, 264) also translate relative to waveguide (192) and blade (190) to dislodge surgical debris caked onto waveguide (192) and/or blade (190).

In some versions, scrapers (262, 266) are rigid. In some other examples, scrapers are flexible (e.g., elastomeric). Various suitable materials that may be used to form scrapers (262, 266) will be apparent to those of ordinary skill in the art in view of the teachings herein. Similarly, various suitable properties that scrapers (262, 266) may have will be apparent to those of ordinary skill in the art in view of the teachings herein.

5. Exemplary Shaft Assembly with Flush Port

FIGS. 45A-47 show an alternative shaft assembly (3150) and end effector (3180) that may be incorporated into instrument (10) in place of shaft assembly (150) and end effector (180). Shaft assembly (3150) and end effector (3180) may be configured and operable just like shaft assembly (150) and end effector (180) except for the differences described below. End effector (3180) includes a clamp arm (3182), clamp pad (3184) and blade (3190) that are substantially similar to clamp arm (182), clamp pad (184) and blade (190) mentioned above, with the differences described below. Shaft assembly (3150) includes a distal seal (3193), an acoustic waveguide (3192), an outer tube (3152), and an inner tube (3170) that are substantially similar to distal seal (193), acoustic waveguide (192), outer tube (152) and inner tube (170) mentioned above, with differences described below. Inner tube (3170) includes a distally projecting tongue (3172) that is substantially similar to distally projecting tongue (172) mentioned above. Outer tube (3152) includes a distally projecting tongue (3154) that is substantially similar to distally projecting tongue (154) mentioned above. Clamp arm (3182) is pivotally connected to pin (3188) and integral pin feature (3186) such that translation of outer tube (3152) pivots clamp arm (3182) toward and away from ultrasonic blade (3190).

Figure 45B:
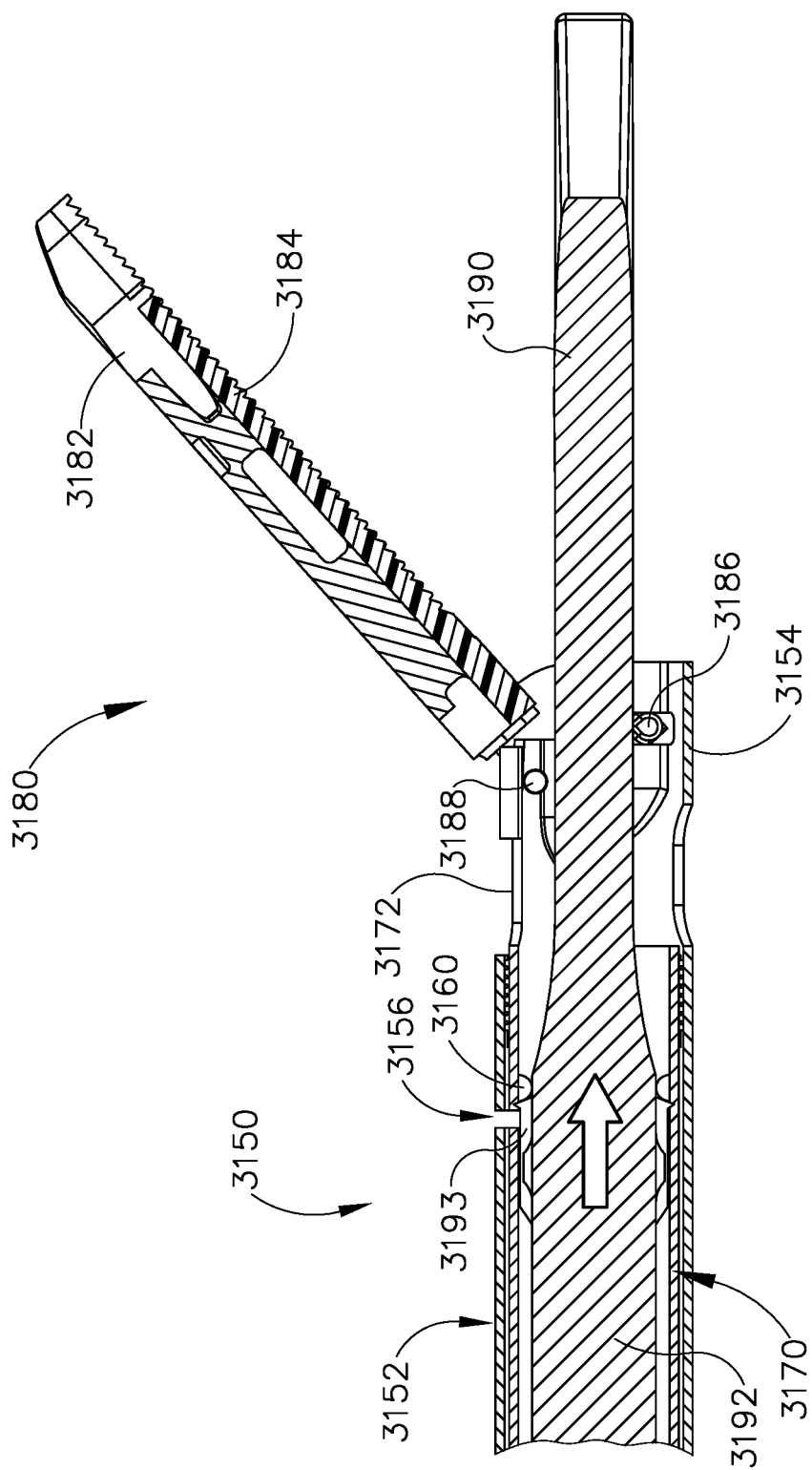
FIG. 45B depicts a cross-sectional side view of the shaft assembly and end effector of FIG. 45A, where the waveguide of the shaft assembly is in a second, distal position.

As best seen in FIGS. 45A-45B, outer tube (3152) and inner tube (3170) together define a flush port (3156). A cleaning feature (3160) extends from the inner diameter of inner tube (3170) toward waveguide (3192). In between surgical procedures, acoustic waveguide (3192) and blade (3190) may be advanced distally such that distal seal (3192) makes contact with cleaning feature (3160). Cleaning feature (3160) is dimensioned to make contact with acoustic waveguide (3192) when waveguide (3192) and blade (3190) are advanced distally. Cleaning feature (3160) may dislodge any excess surgical debris that caked onto the portion of waveguide (3192) in contact with cleaning feature (3160). Waveguide (3192) and blade (3190) may be advanced proximally back to the position shown in FIG. 45A, and an operator may inject fluid into flush port (3156) to wash away any debris remaining on waveguide (3192).

Figure 47:
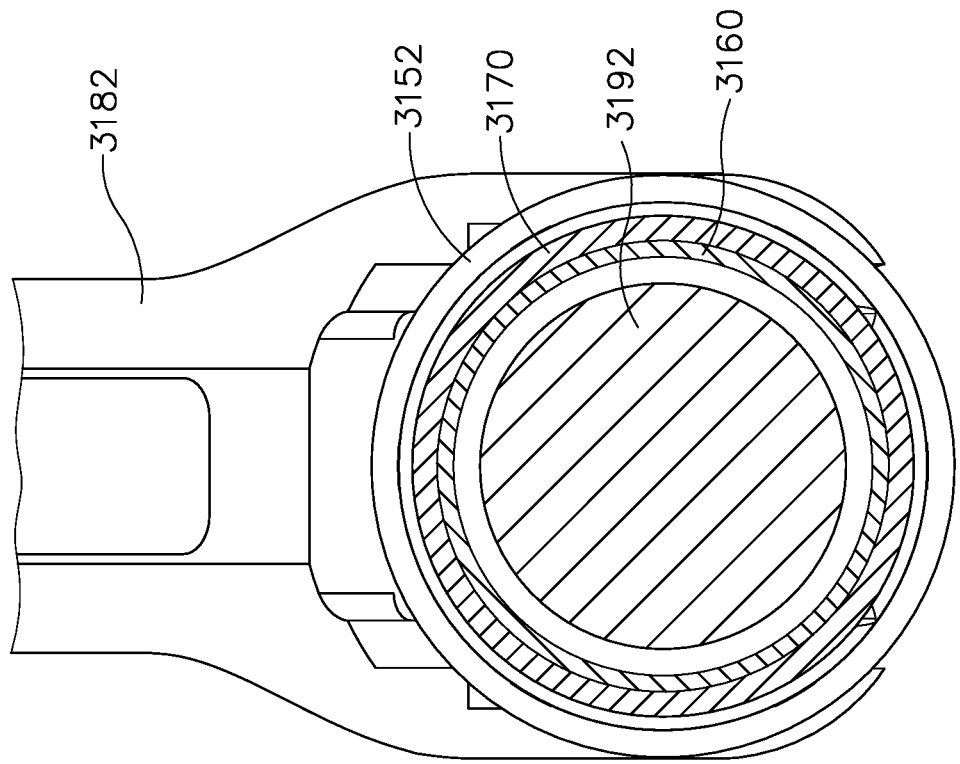
FIG. 47 depicts a cross-section view of the shaft assembly and the end effector of FIG. 45A, taken along line 46-46 of FIG. 45A, with a second alternative embodiment of the cleaning feature.
Figure 46:
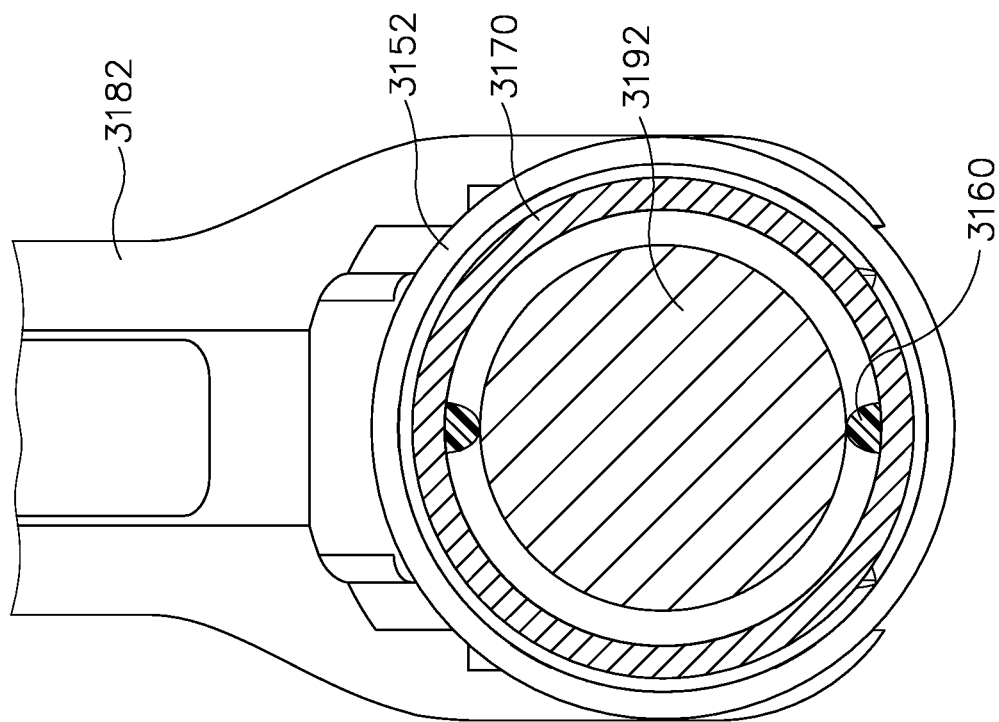
FIG. 46 depicts a cross-sectional view of the shaft assembly and end effector of FIG. 45A, taken along line 46-46 of FIG. 45A, with a first alternative embodiment of a cleaning feature.

FIGS. 46-47 show different geometric shapes that cleaning feature (3160) may have. FIG. 46 shows cleaning feature (3160) as a pair of nubs making contact with the top and bottom of waveguide (3192). Alternatively, FIG. 47 shows cleaning feature (3160) as a ring encompassing waveguide (3192). Any other geometric shape may be used as would be apparent to one having ordinary skill in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a shaft assembly defining a longitudinal axis, wherein the shaft assembly comprises: (i) a first tube having an first inner diameter and a distal end, and (ii) an acoustic waveguide having a first outer diameter, wherein the acoustic waveguide extends within the first tube, wherein the first outer diameter of the acoustic waveguide and the first inner diameter of the first tube together define a gap; (b) an ultrasonic blade coupled with the acoustic waveguide, wherein the ultrasonic blade extends distally from the distal end of the first tube, wherein the acoustic waveguide is configured to communicate ultrasonic energy to the ultrasonic blade; and (c) a cleaning device configured to actuate within the gap to thereby clean at least a portion of the shaft assembly and/or at least a portion of the ultrasonic blade.

Example 2

The surgical instrument of Example 1, wherein the cleaning device comprises a brush assembly configured to actuate within the gap.

Example 3

The surgical instrument of Example 2, wherein the brush assembly further comprises a wire and a brush.

Example 4

The surgical instrument of Example 3, wherein the wire and the brush extend along a helical path.

Example 5

The surgical instrument of Example 4, wherein the helical path defines a second inner diameter and a second outer diameter, wherein the second inner diameter is configured to contact the first outer diameter, wherein the second outer diameter is configured to contact the first inner diameter.

Example 6

The surgical instrument of any one of Examples 1 through 5, wherein the cleaning device further defines a lumen configured to deliver fluid within the first tube.

Example 7

The surgical instrument of any one of Examples 1 through 6, wherein the ultrasonic blade has a curved longitudinal profile.

Example 8

The surgical instrument of any one of Examples 1 through 7, wherein the surgical instrument further comprises a body, wherein the cleaning device is housed within the body, wherein the cleaning device is configured to be removed from the body in order to actuate within the gap.

Example 9

The surgical instrument of any one of Examples 1 through 8, wherein the cleaning device comprises a hollow shaft, wherein the hollow shaft is configured to actuate within the gap.

Example 10

The surgical instrument of Example 9, wherein the cleaning device further comprises a brush, wherein the brush wraps around the hollow shaft, wherein the brush is configured to contact the first inner diameter and the first outer diameter when the hollow shaft actuates within the gap.

Example 11

The surgical instrument of Example 10, wherein the hollow shaft further comprises a plurality of recesses.

Example 12

The surgical instrument of Example 11, wherein the cleaning device further comprises a retention sleeve configured to retain the brush relative to the hollow shaft.

Example 13

The surgical instrument of any one of Examples 11 through 12, wherein the brush at least partially extends through the plurality of recesses.

Example 14

The surgical instrument of any one of Examples 9 through 13, wherein the cleaning device further comprises a plurality of brushes traveling along the length of the hollow shaft on an exterior of the hollow shaft and an interior of the hollow shaft.

Example 15

The surgical instrument of any one of Examples 10 through 14, wherein the hollow shaft further comprise a radial array of protrusions, wherein the brush wraps around at least one protrusion of the radial array of protrusions.

Example 16

The surgical instrument of any one of Examples 9 through 15, wherein the hollow shaft is layered in an abrasive material.

Example 17

The surgical instrument of any one of Examples 9 through 16, wherein the hollow shaft comprises a scraper edge configured to wrap around the first outer diameter when the cleaning device actuates within the gap.

Example 18

A surgical instrument comprising: (a) a shaft assembly defining a longitudinal axis, wherein the shaft assembly comprises: (i) a first tube having an first inner diameter and distal end, wherein the first tube defines a slot, and (ii) an acoustic waveguide having a first outer diameter, wherein the acoustic waveguide extends within the first tube, wherein the first outer diameter of the acoustic waveguide and the first inner diameter of the first tube together define a gap; (b) an ultrasonic blade coupled with the acoustic waveguide, wherein the ultrasonic blade extends distally from the distal end of the first tube, wherein the acoustic waveguide is configured to communicate ultrasonic energy to the ultrasonic blade; and (c) a cleaning device configured to actuate within the gap and along the slot to thereby clean at least a portion of the shaft assembly and/or at least a portion of the ultrasonic blade.

Example 19

The surgical instrument of Example 18, wherein the slot forms an arced path, wherein the cleaning device is configure to actuate within the gap by rotating within the slot.

Example 20

A surgical instrument comprising: (a) a shaft assembly defining a longitudinal axis, wherein the shaft assembly comprises: (i) a first tube having an first inner diameter and a distal end, and (ii) an acoustic waveguide having a first outer diameter, wherein the acoustic waveguide extends within the first tube, wherein the first outer diameter of the acoustic waveguide and the first inner diameter of the first tube define a gap; (b) an end effector comprising: (i) an ultrasonic blade coupled with the acoustic waveguide, wherein the ultrasonic blade extends distally from the distal end of the first tube, wherein the acoustic waveguide is configured to communicate ultrasonic energy to the ultrasonic blade, and (ii) a clamp arm configured to pivot toward and away from the ultrasonic blade; and (c) a cleaning device configured to actuate within the gap in response to the clamp arm pivoting toward and away from the ultrasonic blade to thereby clean at least a portion of the shaft assembly and/or at least a portion of the ultrasonic blade.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument comprising:
(a) a shaft assembly defining a longitudinal axis, wherein the shaft assembly comprises:
(i) a first tube having a first inner diameter, an outer surface, and a distal end, wherein the first tube defines a slot extending between the first diameter and the outer surface, and

(ii) an acoustic waveguide having a first outer diameter, wherein the acoustic waveguide extends within the first tube, wherein the first outer diameter of the acoustic waveguide and the first inner diameter of the first tube together define a gap;

(b) an ultrasonic blade coupled with the acoustic waveguide, wherein the ultrasonic blade extends distally from the distal end of the first tube, wherein the acoustic waveguide is configured to communicate an ultrasonic energy to the ultrasonic blade; and (c) a cleaning device configured to actuate within the gap and along the slot to thereby clean at least one of at least a portion of the shaft assembly or at least a portion of the ultrasonic blade.

2. The surgical instrument of claim 1, wherein the slot forms an arced path, wherein the cleaning device is configured to actuate within the gap by rotating within the slot.

3. The surgical instrument of claim 2, wherein the cleaning device comprises an annular grip slidably coupled with the first tube.

4. The surgical instrument of claim 3, wherein the cleaning device further comprises a plurality of scrapers disposed around the annular grip.

5. The surgical instrument of claim 4, wherein the plurality of scrapers are dimensioned to contact the acoustic waveguide.

6. A surgical instrument comprising:
(a) a shaft assembly defining a longitudinal axis, wherein the shaft assembly comprises:
  (i) a first tube having a first inner diameter and a distal end, and
  (ii) an acoustic waveguide having a first outer diameter, wherein the acoustic waveguide extends within the first tube, wherein the first outer diameter of the acoustic waveguide and the first inner diameter of the first tube defines a gap;
(b) an end effector comprising:
  (i) an ultrasonic blade coupled with the acoustic waveguide, wherein the ultrasonic blade extends distally from the distal end of the first tube, wherein the acoustic waveguide is configured to communicate an ultrasonic energy to the ultrasonic blade, and
  (ii) a clamp arm configured to pivot toward and away from the ultrasonic blade; and
(c) a cleaning device comprising a body and a pair of legs, wherein the body comprises an array of scrapers in contact with the first outer diameter of the acoustic waveguide, wherein the cleaning device is configured to actuate within the gap in response to the clamp arm pivoting toward and away from the ultrasonic blade to thereby clean at least one of at least a portion of the shaft assembly or at least a portion of the ultrasonic blade.

7. The surgical instrument of claim 6, wherein the pair of legs are coupled with the end effector.

8. The surgical instrument of claim 7, wherein each of the pair of legs defines a kidney slot, wherein each of the kidney slots houses an integral pin feature of the shaft assembly.

9. A surgical instrument comprising:
(a) a shaft assembly defining a longitudinal axis, wherein the shaft assembly comprises:
  (i) a first tube having a first inner diameter and a distal end, and
  (ii) an acoustic waveguide having a first outer diameter, wherein the acoustic waveguide extends within the first tube, wherein the first outer diameter of the acoustic waveguide and the first inner diameter of the first tube together define a gap;
(b) an ultrasonic blade coupled with the acoustic waveguide, wherein the ultrasonic blade extends distally from the distal end of the first tube, wherein the acoustic waveguide is configured to communicate an ultrasonic energy to the ultrasonic blade; and
(c) a cleaning device defining a lumen, wherein a portion of the cleaning device defining the lumen is configured to actuate within the gap to thereby clean at least one of at least a portion of the shaft assembly or at least a portion of the ultrasonic blade, wherein the portion of the cleaning device defining the lumen comprises an open distal tip and a hollow shaft, wherein the hollow shaft comprises an abrasive material.

10. The surgical instrument of claim 9, wherein the cleaning device further comprises a plurality of brushes traveling along the length of the hollow shaft on an exterior of the hollow shaft and an interior of the hollow shaft.

11. The surgical instrument of claim 9, wherein the hollow shaft comprises a scraper edge configured to wrap around the first outer diameter when the cleaning device actuates within the gap.

12. The surgical instrument of claim 9, wherein the cleaning device further comprises a brush, wherein the brush wraps around the hollow shaft.

13. The surgical instrument of claim 12, wherein the hollow shaft comprises a plurality of recesses.

14. The surgical instrument of claim 13, wherein the cleaning device further comprises a retention sleeve configured to retain the brush relative to the hollow shaft.

15. The surgical instrument of claim 13, wherein the brush at least partially extends through the plurality of recesses.

16. The surgical instrument of claim 12, wherein the hollow shaft further comprises a radial array of protrusions, wherein the brush wraps around at least one protrusion of the radial array of protrusions.

17. The surgical instrument of claim 9, wherein the hollow shaft further comprises a plurality of flexible ribs.

* * * * *